(12) United States Patent
Stoessel et al.

(10) Patent No.: US 10,135,003 B2
(45) Date of Patent: *Nov. 20, 2018

US010135003B2

(54) MATERIALS FOR ELECTRONIC DEVICES

(71) Applicant: Merck Patent GmbH, Darmstadt (DE)

(72) Inventors: Philipp Stoessel, Frankfurt am Main (DE); Arne Buesing, Frankfurt am Main (DE); Dominik Joosten, Frankfurt am Main (DE)

(73) Assignee: Merck Patent GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,051

(22) Filed: Jun. 26, 2017

(65) Prior Publication Data

US 2017/0309834 A1 Oct. 26, 2017

Related U.S. Application Data

(63) Continuation of application No. 15/153,185, filed on May 12, 2016, which is a continuation of application No. 13/805,927, filed as application No. PCT/EP2011/002668 on May 30, 2011, now Pat. No. 9,379,330.

(30) Foreign Application Priority Data

Jun. 22, 2010 (DE) ........................ 10 2010 024 542

(51) Int. Cl.
*H01L 51/00* (2006.01)
*C07D 487/04* (2006.01)
*H01L 51/50* (2006.01)

(52) U.S. Cl.
CPC ........ *H01L 51/0072* (2013.01); *C07D 487/04* (2013.01); *H01L 51/0061* (2013.01); *H01L 51/0067* (2013.01); *B32B 2457/202* (2013.01); *H01L 51/006* (2013.01); *H01L 51/0037* (2013.01); *H01L 51/0056* (2013.01); *H01L 51/0058* (2013.01); *H01L 51/0081* (2013.01); *H01L 51/0085* (2013.01); *H01L 51/0094* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5096* (2013.01)

(58) Field of Classification Search
None
See application file for complete search history.

(56) References Cited

U.S. PATENT DOCUMENTS

| 3,669,969 A | 6/1972 | Lunn |
| 6,551,723 B1 * | 4/2003 | Okada ................ H01L 51/004 313/504 |
| 9,379,330 B2 * | 6/2016 | Stoessel ............... C07D 235/00 |

FOREIGN PATENT DOCUMENTS

| DE | 2058185 A1 | 6/1971 |
| JP | 59-042385 A | 3/1984 |
| JP | 5-107705 B2 | 4/1993 |
| JP | 2001-076878 A | 3/2001 |
| JP | 2001-160488 A | 6/2001 |
| SU | 1669913 A1 | 8/1991 |
| WO | WO-2008142635 A2 | 11/2008 |

OTHER PUBLICATIONS

Via, Lisa Dalla, et al., "Synthesis, in Vitro Antiproliferative Activity and DNA-Interaction of Benzimidazoquinazoline Derivatives as Potential Anti-Tumor Agents". Il Farmaco, vol. 56, (2001), pp. 159-167.
International Search Report for PCT/EP2011/0026668 dated Sep. 23, 2011.

* cited by examiner

*Primary Examiner* — Anthony J Frost
(74) *Attorney, Agent, or Firm* — Drinker Biddle & Reath LLP

(57) ABSTRACT

The present invention relates to an electronic device comprising anode, cathode and at least one organic layer which comprises a compound of the formula (I) to (IV). The invention furthermore encompasses the use of compounds of the formula (I) to (IV) in an electronic device and to a compound of the formula (Ic) to (IVc).

18 Claims, No Drawings

MATERIALS FOR ELECTRONIC DEVICES

CROSS-REFERENCE TO RELATED APPLICATIONS

This application is a continuation application of U.S. application Ser. No. 15/153,185 filed May 12, 2016 which is a continuation application of U.S. application Ser. No. 13/805,927 filed Dec. 20, 2012. U.S. application Ser. Nos. 15/153,185 and 13/805,927 are incorporated by reference in their entirety. U.S. application Ser. No. 13/805,927 is a national stage application (under 35 U.S.C. § 371) of PCT/EP2011/002668, filed May 30, 2011, which claims benefit of German application 10 2010 024 542.9, filed Jun. 22, 2010 which are both incorporated by reference.

The present invention relates to an electronic device comprising at least one compound of the formula (I) to (IV), to the use of compounds of the formula (I) to (IV) in an electronic device and to a compound of the formula (Ic) to (IVc).

Electronic devices in the sense of the present invention are preferably organic electroluminescent devices, but may also represent other electronic devices, as described in greater detail later.

The general structure of an organic electroluminescent device (OLED) is revealed, inter alia, by U.S. Pat. No. 4,539,507, U.S. Pat. No. 5,151,629, EP 0676461 and WO 1998/27136.

With respect to the performance data and lifetime of organic electroluminescent devices, considerable advances have been achieved in recent years. However, there is a further need for improvement, in particular in the following points:
1. An increase in the power efficiency of the devices is desirable.
2. There is still a need for improvement in the operating lifetime of the devices, in particular in the case of blue emission.
3. A reduction in the operating voltage of the devices is desirable. This is of major importance, in particular, for mobile applications.

Thus, there continues to be a demand for novel functional materials for organic electroluminescent devices which have a positive influence on the performance data of the devices, in particular in the points mentioned above.

Furthermore, generally in the area of materials for organic electroluminescent devices, there is interest in the provision of novel, alternative compounds which are suitable for use in the said devices and with which comparably good performance data as with compounds which are already known can be achieved.

Inter alia, arylamine compounds are known in the prior art as hole-transport and -injection materials for organic electroluminescent devices. Materials of this type based on an indenofluorene skeleton are disclosed, for example, in WO 2006/100896 and WO 2006/122630.

However, the hole-transporting materials known in the prior art frequently have low electron stability, which reduces the lifetime of electronic devices comprising these compounds.

There is therefore, in particular, a demand for novel compounds for use as hole-transport and/or hole-injection materials in the above-mentioned devices.

Inter alia, carbazole derivatives, for example bis(carbazolyl)biphenyl, are known in the prior art as matrix materials for phosphorescent dopants. Also known is the use of ketones (WO 2004/093207), phosphine oxides and sulfones (WO 2005/003253) as matrix materials for phosphorescent dopants. Metal complexes, for example BAlq or zinc(II) bis[2-(2-benzothiazole)phenolate], are also used as matrix materials for phosphorescent dopants.

However, there continues to be a demand for alternative matrix materials for phosphorescent dopants, in particular those which effect an improvement in the performance data of the electronic devices.

Also of particular interest is the provision of alternative materials as matrix components of mixed-matrix systems. A mixed-matrix system in the sense of this application is taken to mean a system in which two or more different compounds are used in an emitting layer mixed together with an (alternatively also several) dopant compounds. These systems are, in particular, of interest in the case of phosphorescent organic electroluminescent devices. For more detailed information, reference is made to the application WO 2010/108579.

Compounds known in the prior art which may be mentioned for use as matrix components in mixed-matrix systems are, inter alia, CBP (biscarbazolylbiphenyl) and TCTA (triscarbazolyltriphenylamine) (first component). Suitable as second component are compounds such as, for example, benzophenone derivatives, diazaphospholes (WO 2010/054730) and triazines. However, there continues to be a demand for alternative compounds for use as matrix components in mixed-matrix systems. In particular, there is a demand for compounds which effect an improvement in the operating voltage and lifetime of the electronic devices.

Overall, further improvements are desirable with respect to the efficiency and lifetime of fluorescent and/or phosphorescent organic electroluminescent devices. Potential for improvement furthermore exists in the case of the operating voltage of the electronic devices.

The present invention provides novel organic electroluminescent devices in order to achieve the technical object described above.

The invention thus relates to an electronic device comprising anode, cathode and at least one organic layer, characterised in that the organic layer comprises at least one compound of the following formulae (I) to (IV)

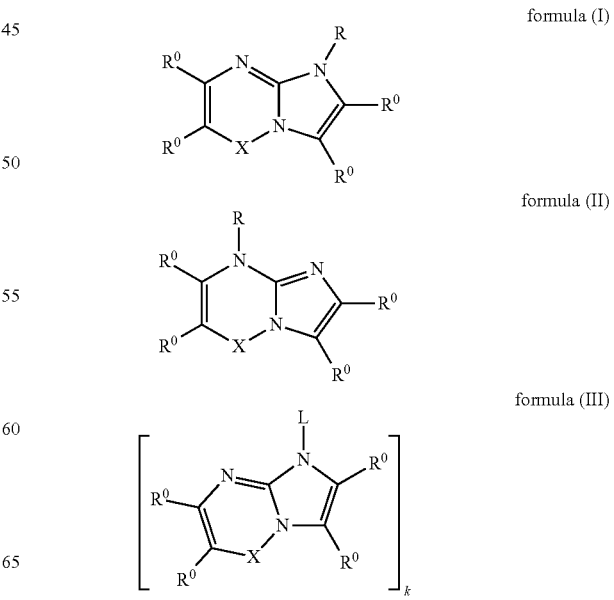

-continued

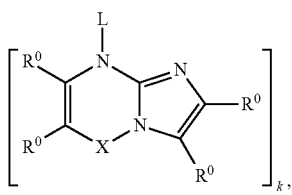

formula (IV)

where the following applies to the symbols occurring:

X is on each occurrence, identically or differently, a single bond, C=O, C=S, C=NR$^1$, C(R$^1$)$_2$, C(R$^1$)$_2$—C(R$^1$)$_2$, CR$^1$=CR$^1$, Si(R$^1$)$_2$, NR$^1$, PR$^1$, P(=O)R$^1$, O, S, SO or SO$_2$;

L is a divalent, or in the case of k=3, 4, 5 or 6 a tri-, tetra-, penta- or hexavalent group respectively, selected from C=O, C=NR$^1$, Si(R$^1$)$_2$, P(=O)(R$^1$), SO, SO$_2$, alkylene groups having 1 to 20 C atoms, alkenylene or alkynylene groups having 2 to 20 C atoms, where, in the case of the groups mentioned, one or more CH$_2$ groups may be replaced by Si(R$^1$)$_2$, O, S, C=O, C=NR$^1$, C=O—O, C=O—NR$^1$, NR$^1$, P(=O)(R$^1$), SO or SO$_2$ and where one or more H atoms in the above-mentioned groups may be replaced by D, F, Cl, Br, I, CN or NO$_2$, aromatic or heteroaromatic ring systems having 5 to 60 aromatic ring atoms, each of which may be substituted by one or more radicals R$^1$, and any desired combinations of 1, 2, 3, 4 or 5 identical or different groups selected from the above-mentioned groups; or L is a single bond, where k in this case must be equal to 2;

R$^0$ is on each occurrence, identically or differently, H, D, F, Cl, Br, I, C(=O)R$^1$, OSO$_2$R$^1$, COOR$^1$, CON(R$^1$)$_2$, a straight-chain alkyl group having 1 to 40 C atoms or a branched or cyclic alkyl group having 3 to 40 C atoms or an alkenyl or alkynyl group having 2 to 40 C atoms, where the above-mentioned groups may each be substituted by one or more radicals R$^1$ and where one or more CH$_2$ groups in the above-mentioned groups may be replaced by Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, —O—, —S—, —COO— or —CONR$^1$— and where one or more H atoms in the above-mentioned groups may be replaced by D, F, Cl, Br, I, CN or NO$_2$, or an aromatic or heteroaromatic ring system having 5 to 60 aromatic ring atoms, which may in each case be substituted by one or more radicals R$^1$, or an aralkyl or heteroaralkyl group having 5 to 60 aromatic ring atoms, which may be substituted by one or more radicals R$^1$, or a combination of these systems, furthermore two or more adjacent radicals R$^0$ may be linked to one another here and form an aliphatic or aromatic ring, or a radical R$^0$ may be linked to an adjacent radical R via a single bond or a divalent group Y and form an aliphatic or aromatic ring;

R is equal to C(=O)R$^1$, OSO$_2$R$^1$, COOR$^1$, CON(R$^1$)$_2$, a straight-chain alkyl group having 1 to 40 C atoms or a branched or cyclic alkyl group having 3 to 40 C atoms or an alkenyl or alkynyl group having 2 to 40 C atoms, where the above-mentioned groups may each be substituted by one or more radicals R$^1$ and where one or more CH$_2$ groups in the above-mentioned groups may be replaced by Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, —O—, —S—, —COO— or —CONR$^1$— and where one or more H atoms in the above-mentioned groups may be replaced by D, F, Cl, Br, I, CN or NO$_2$, or an aromatic or heteroaromatic ring system having 5 to 60 aromatic ring atoms, which may in each case be substituted by one or more radicals R$^1$, or an aralkyl or heteroaralkyl group having 5 to 60 aromatic ring atoms, which may be substituted by one or more radicals R$^1$, or a combination of these systems, where furthermore the radical R may be linked to one or more adjacent radicals R$^0$ via a single bond or a divalent group Y;

Y is on each occurrence, identically or differently, a divalent group selected from C=O, C=S, C=NR$^1$, C(R$^1$)$_2$, Si(R$^1$)$_2$, NR$^1$, PR$^1$, P(=O)R$^1$, O, S, SO and SO$_2$;

R$^1$ is on each occurrence, identically or differently, H, D, F, Cl, Br, I, CHO, N(R$^2$)$_2$, C(=O)R$^2$, P(=O)(R$^2$)$_2$, S(=O)R$^2$, S(=O)$_2$R$^2$, CN, NO$_2$, Si(R$^2$)$_3$, B(OR$^2$)$_2$, OSO$_2$R$^2$, OH, COOR$^2$, CON(R$^2$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals R$^2$ and where one or more CH$_2$ groups in the above-mentioned groups may be replaced by Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, —O—, —S—, —COO— or —CONR$^2$— and where one or more H atoms in the above-mentioned groups may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which may be substituted by one or more radicals R$^2$, or a combination of these systems, where two or more radicals R$^1$ may be linked to one another and may form an aliphatic or aromatic ring;

R$^2$ is, identically or differently on each occurrence, H, D, F or an aliphatic, aromatic and/or heteroaromatic organic radical having 1 to 20 C atoms, in which, in addition, one or more H atoms may be replaced by D or F; two or more substituents R$^2$ here may also be linked to one another and form an aliphatic or aromatic ring; and k is equal to 2, 3, 4, 5 or 6.

Preferred embodiments of compounds of the formula (I), (II), (III) and (IV) are the following compounds of the formula (Ia), (Ib), (IIa), (IIb), (IIIa), (IIIb), (IVa) and (IVb)

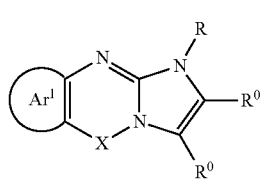

formula (Ia)

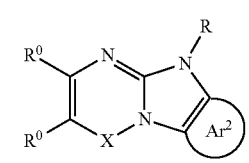

formula (Ib)

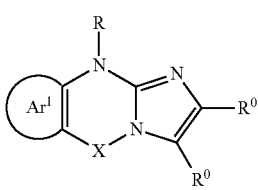

formula (IIa)

formula (IIb)

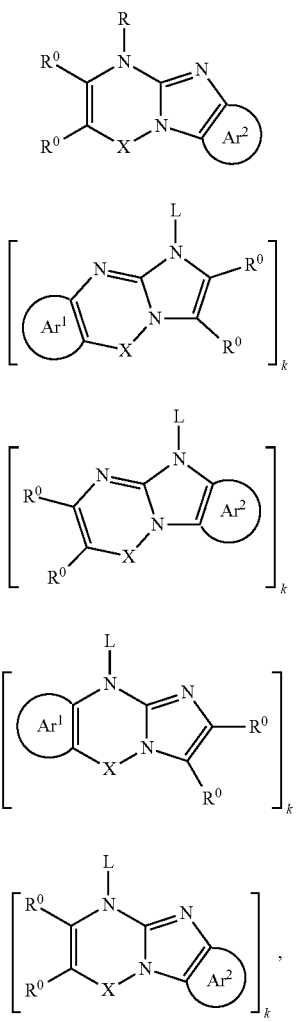

formula (IIIa)

formula (IIIb)

formula (IVa)

formula (IVb)

where the symbols occurring are as defined above and furthermore:

Ar¹, Ar² are, identically or differently, an aryl group containing 6 to 60 aromatic ring atoms or a heteroaryl group containing 5 to 60 aromatic ring atoms, each of which may be substituted by one or more radicals $R^1$; and R may be linked, analogously to the above-mentioned definition, to one or more radicals $R^0$ and/or an adjacent group Ar¹ or Ar² via a single bond or via a divalent group Y.

Particularly preferred embodiments of compounds of the formulae (I), (II), (III) and (IV) are the compounds of the formulae (Ic), (IIc), (IIIc) and (IVc) shown below formula (Ic)

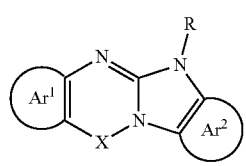

formula (IIc)

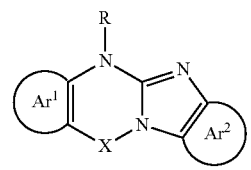

formula (IIIc)

formula (IVc)

where the symbols occurring are as defined above and furthermore:

Ar², Ar² are, identically or differently, an aryl group containing 6 to 60 aromatic ring atoms or a heteroaryl group containing 5 to 60 aromatic ring atoms, each of which may be substituted by one or more radicals $R^1$; and R may be linked, analogously to the above-mentioned definition, to one or more adjacent groups Ar¹ and Ar² via a single bond or via a divalent group Y.

The groups

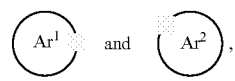

drawn adjacent to the heterocycles in the above-mentioned formulae denote that a group Ar¹ or Ar², as defined above, is condensed onto the heterocycle in question, so that it forms a common condensed heteroaryl group with the heterocycle. The preferred embodiments of the compounds of the formula (I) to (IV) mentioned in later sections illustrate this principle.

It is preferred in accordance with the invention for the groups Ar¹ and Ar² to be selected, identically or differently, from aryl groups having 6 to 20 aromatic ring atoms, which may be substituted by one or more radicals $R^1$, and heteroaryl groups having 5 to 20 aromatic ring atoms, which may be substituted by one or more radicals $R^1$. The groups Ar¹ and Ar² are particularly preferably selected on each occurrence, identically or differently, from aryl groups having 6 to 14 aromatic ring atoms, which may be substituted by one or more radicals $R^1$, and heteroaryl groups having 5 to 14 aromatic ring atoms, which may be substituted by one or more radicals $R^1$.

In the sense of this invention, condensed aromatic or heteroaromatic rings are generally taken to mean rings which have at least two adjacent aromatic ring atoms in common with one another. A corresponding definition also applies analogously to aliphatic rings.

Furthermore, the formulation that a ring is condensed onto another ring is in the sense of this invention taken to mean that the condensed-on ring has at least two adjacent ring atoms in common with the first ring.

An aryl group in the sense of this invention contains 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, P, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

An aryl or heteroaryl group, which may in each case be substituted by the above-mentioned radicals $R^1$ or $R^2$ and which may be linked to the aromatic or heteroaromatic ring system via any desired positions, is taken to mean, in particular, groups derived from benzene, naphthalene, anthracane, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aralkyl group in the sense of this invention is an alkyl group which is substituted by an aryl group, where the term aryl group is to be understood as defined above and alkyl group is defined as a non-aromatic organic radical having 1-40 atoms, in which, in addition, individual H atoms or $CH_2$ groups may be substituted by the groups mentioned above in the definition of R and $R^1$.

A heteroaralkyl group in the sense of this invention is an alkyl group which is substituted by a heteroaryl group, where the term heteroaryl group is to be understood as defined above and alkyl group is defined as a non-aromatic organic radical having 1-40 atoms, in which, in addition, individual H atoms or $CH_2$ groups may be substituted by the groups mentioned above in the definition of R and $R^1$.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, a C, Si, N or O atom or a carbonyl group. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds, such as, for example, biphenyl, terphenyl or bipyridine, are also intended to be taken to be aromatic or heteroaromatic ring systems in the sense of this invention.

An aromatic or heteroaromatic ring system having 5-60 aromatic ring atoms, which may also in each case be substituted by radicals as defined above and which may be linked via any desired positions on the aromatic or heteroaromatic group, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, where, in addition, individual H atoms or $CH_2$ groups in the above-mentioned groups may be substituted by the groups mentioned above in the case of the definition of the radicals R and $R^1$, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

Preferred embodiments of the compounds of the formula (Ic) to (IVc) are illustrated by the following formulae (V) to (X)

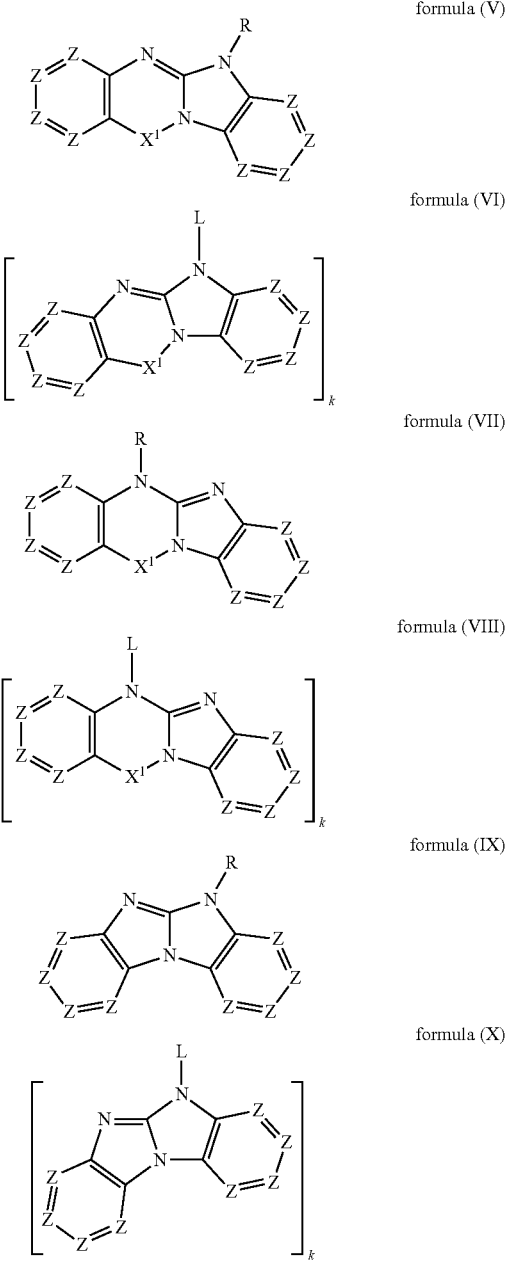

formula (V)

formula (VI)

formula (VII)

formula (VIII)

formula (IX)

formula (X)

where furthermore:

$X^1$ is selected from C=O, C=S, C=NR$^1$, C(R$^1$)$_2$, C(R$^1$)$_2$—C(R$^1$)$_2$, NR$^1$, PR$^1$, P(=O)R$^1$, O, S, SO and SO$_2$;

Z is on each occurrence, identically or differently, CR$^1$ or N, where not more than two adjacent groups Z may simultaneously be equal to N;

and the other symbols occurring are as defined above.

In a preferred embodiment of the invention, not more than three groups Z in a formula are equal to N, and the remaining groups Z are equal to CR$^1$. In a particularly preferred embodiment, all groups Z in a formula are equal to CR$^1$.

In a further preferred embodiment of the invention, the group X is selected from a single bond, C=O, C=NR$^1$, C(R$^1$)$_2$, CR$^1$=CR$^1$, NR$^1$, O and S. X is particularly preferably selected from a single bond, C=O and C(R$^1$)$_2$.

If the group X represents a group of the formula C(R$^1$)$_2$, it is a preferred embodiment that the two radicals R$^1$ which are bonded to the same C atom are linked to one another and form an aliphatic or aromatic ring.

In a further preferred embodiment of the invention, the group $X^1$ is selected from C=O, C=NR$^1$, C(R$^1$)$_2$, CR$^1$=CR$^1$, NR$^1$, O and S. $X^1$ is particularly preferably selected from C=O and C(R$^1$)$_2$.

If the group $X^1$ represents a group of the formula C(R$^1$)$_2$, it is a preferred embodiment that the two radicals R$^1$ which are bonded to the same C atom are linked to one another and form an aliphatic or aromatic ring.

In a further preferred embodiment of the invention, R$^0$ is on each occurrence, identically or differently, H, D, F, Cl, Br, I, N(R$^1$)$_2$, C(=O)R$^1$, CN, Si(R$^1$)$_3$, COOR$^1$, CON(R$^1$)$_2$, a straight-chain alkyl, alkoxy or thioalkyl group having 1 to 10 C atoms or a branched or cyclic alkyl, alkoxy or thioalkyl group having 3 to 10 C atoms or an alkenyl or alkynyl group having 2 to 10 C atoms, where the above-mentioned groups may each be substituted by one or more radicals R$^1$ and where one or more non-adjacent CH$_2$ groups in the above-mentioned groups may be replaced by Si(R$^1$)$_2$, C=O, C=NR$^1$, SO, SO$_2$, NR$^1$, —O—, —S—, —COO— or —CONR$^1$— and where one or more H atoms in the above-mentioned groups may be replaced by D, F, Cl, Br, I or CN, or an aromatic or heteroaromatic ring system having 5 to 20 aromatic ring atoms, which may in each case be substituted by one or more radicals R$^1$, or an aryloxy or heteroaryloxy group having 5 to 20 aromatic ring atoms, which may be substituted by one or more radicals R$^1$, or a combination of these systems, furthermore, two or more adjacent radicals R$^0$ may be linked to one another and form an aliphatic or aromatic ring or a radical R$^0$ may be linked to an adjacent radical R via a single bond or a divalent group Y and form an aliphatic or aromatic ring.

In a further preferred embodiment of the invention, the radical R is a straight-chain alkyl group having 1 to 10 C atoms or a branched or cyclic alkyl group having 3 to 10 C atoms or an alkenyl or alkynyl group having 2 to 10 C atoms, where the above-mentioned groups may each be substituted by one or more radicals R$^1$ and where one or more non-adjacent CH$_2$ groups in the above-mentioned groups may be replaced by C=O, C=NR$^1$, P(=O)(R$^1$), SO, SO$_2$, NR$^1$, —O—, —S—, —COO— or —CONR$^1$— and where one or more H atoms in the above-mentioned groups may be replaced by D, F, Cl, Br, I or CN, or an aromatic or heteroaromatic ring system having 5 to 20 aromatic ring atoms, which may in each case be substituted by one or more radicals R$^1$, or an aralkyl or heteroaralkyl group having 5 to 20 aromatic ring atoms, which may be substituted by one or more radicals R$^1$, or a combination of these systems, and where the radical R may furthermore be linked to one of the groups Ar$^1$ and Ar$^2$ via a single bond or via a divalent group Y.

The radical R is particularly preferably an aryl or heteroaryl group having 5 to 20 aromatic ring atoms, which may in each case be substituted by one or more radicals $R^1$, or an aralkyl or heteroalkyl group having 5 to 20 aromatic ring atoms, which may be substituted by one or more radicals $R^1$, where the radical R may furthermore be linked to one of the groups $Ar^1$ and $Ar^2$ via a single bond or via a divalent group Y.

The radical R is again more preferably selected from benzene, pyridine, pyrimidine, pyridazine, pyrazine and triazine, where the said groups may be substituted by one or more radicals $R^1$ and where the radical R may be linked to one of the groups $Ar^1$ and $Ar^2$ via a single bond or via a divalent group Y.

In a preferred embodiment, the divalent group Y is selected, identically or differently, from C=O, C=$NR^1$, $C(R^1)_2$, $NR^1$, O, S and $SO_2$.

In a further preferred embodiment, $R^1$ is on each occurrence, identically or differently, H, D, F, Cl, Br, I, $N(R^2)_2$, $C(=O)R^2$, CN, $Si(R^2)_3$, $COOR^2$, $CON(R^2)_2$, a straight-chain alkyl, alkoxy or thioalkyl group having 1 to 10 C atoms or a branched or cyclic alkyl, alkoxy or thioalkyl group having 3 to 10 C atoms or an alkenyl or alkynyl group having 2 to 10 C atoms, where the above-mentioned groups may each be substituted by one or more radicals $R^2$ and where one or more non-adjacent $CH_2$ groups in the above-mentioned groups may be replaced by $Si(R^2)_2$, C=O, C=$NR^2$, SO, $SO_2$, $NR^2$, —O—, —S—, —COO— or —$CONR^2$— and where one or more H atoms in the above-mentioned groups may be replaced by D, F, Cl, Br, I or CN, or an aromatic or heteroaromatic ring system having 5 to 20 aromatic ring atoms, which may in each case be substituted by one or more radicals $R^2$, or an aryloxy or heteroaryloxy group having 5 to 20 aromatic ring atoms, which may be substituted by one or more radicals $R^2$, or a combination of these systems, where two or more radicals $R^1$ may be linked to one another and may form an aliphatic or aromatic ring.

L is preferably a divalent, or for k=3, 4, 5 or 6 a tri-, tetra-, penta- or hexavalent group respectively, selected from C=O, $NR^1$, P(=O)($R^1$), O, S, alkylene groups having 1 to 10 C atoms, alkenylene groups having 2 to 10 C atoms, where, in the groups mentioned, one or more $CH_2$ groups may be replaced by C=O, $NR^1$, P(=O)($R^1$), O or S, aryl or heteroaryl groups having 5 to 20 aromatic ring atoms and aromatic or heteroaromatic ring systems of the formulae (L-1) or (L-2),

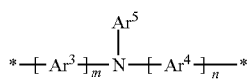

formula (L-1)

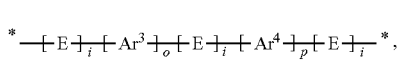

formula (L-2)

where:
$Ar^3$, $Ar^4$ and $Ar^5$ is, identically or differently, an aryl or heteroaryl group having 5 to 20 aromatic ring atoms, which may in each case be substituted by one or more radicals $R^1$;
E is C=O, P(=O)($R^1$), SO or $SO_2$;
i is on each occurrence, identically or differently, 0 or 1;
m, n are, identically or differently, 1, 2 or 3, preferably 1 or 2;
o, p are, identically or differently, 0, 1, 2 or 3, preferably 0, 1 or 2, where both indices o and p cannot simultaneously be zero; and
the symbols * mark the bonds from the group L to the remainder of the compound.

In a preferred embodiment of the invention, k is equal to 2, 3 or 4. k is very particularly preferably equal to 2 or 3.

Particularly preferred embodiments of compounds of the formula (V) to (X) are represented by the formulae (V-1) to (V-6), (VI-1) to (VI-2), (VII-1) to (VII-6), (VIII-1) to (VIII-2), (IX-1) to (IX-3) and (X-1):

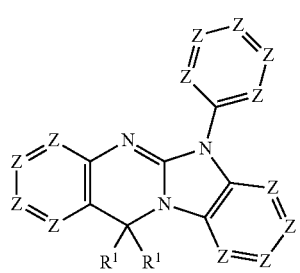

formula (V-1)

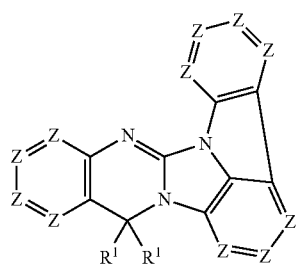

formula (V-2)

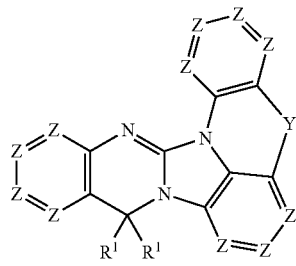

formula (V-3)

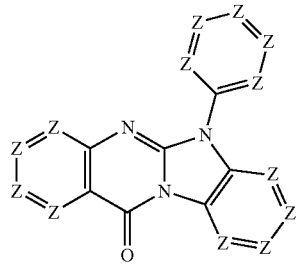

formula (V-4)

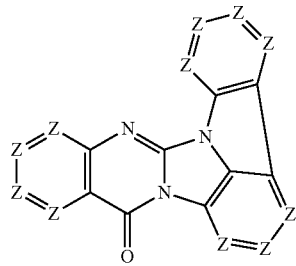

formula (V-5)

formula (V-6)
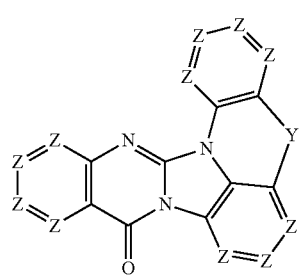
formula (VI-1)
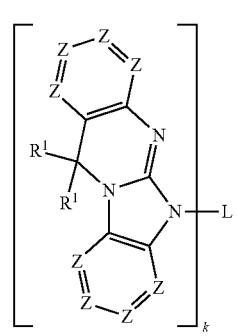
formula (VI-2)
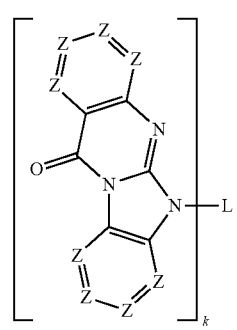
formula (VII-1)
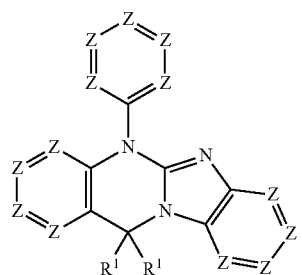
formula (VII-2)
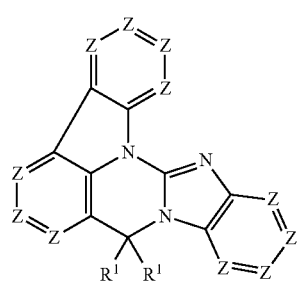
formula (VII-3)
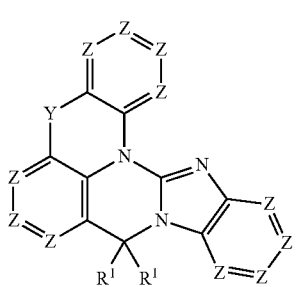
formula (VII-4)
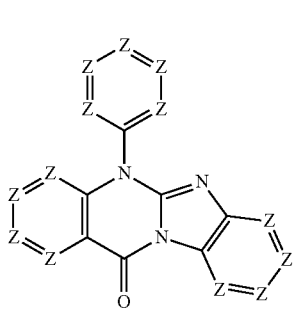
formula (VII-5)
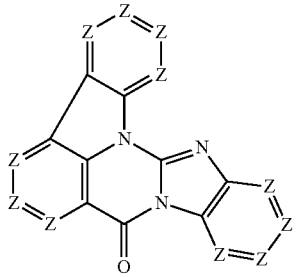
formula (VII-6)
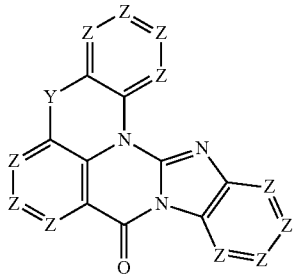
formula (VIII-1)
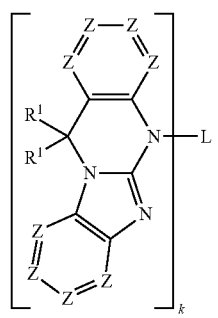

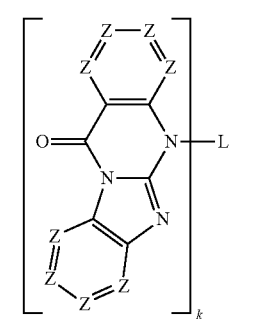

formula (VIII-2)

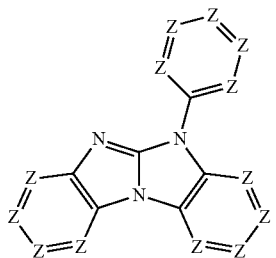

formula (IX-1)

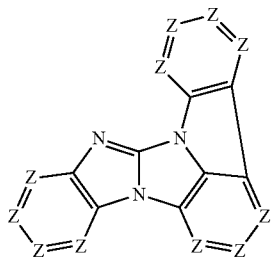

formula (IX-2)

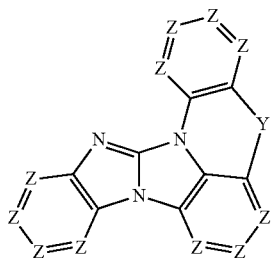

formula (IX-3)

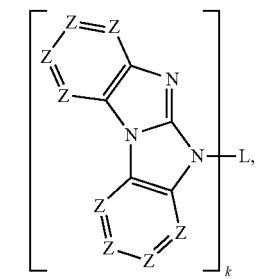

formula (X-1)

where the symbols occurring are as defined above and furthermore

Z is on each occurrence, identically or differently, $CR^1$ or N, where not more than two adjacent groups Z may simultaneously be equal to N.

The above-mentioned preferred embodiments of the groups Z, Y, L, $R^1$, $R^2$ and of the index k also apply to the compounds of the formulae (V-1) to (V-6), (VI-1) to (VI-2), (VII-1) to (VII-6), (VIII-1) to (VIII-2), (IX-1) to (IX-3) and (X-1).

Two or more radicals $R^1$ as constituents of groups $Z=CR^1$ in aromatic or heteroaromatic rings in the above-mentioned formulae may be connected to one another and form a ring which is condensed onto the aromatic or heteroaromatic ring.

It is furthermore preferred for the compounds for use in the electroluminescent devices according to the invention to carry as substituent R, $R^1$ or $R^2$ at least one group which is selected from electron-deficient heteroaryl groups, aromatic or heteroaromatic ring systems and from arylamine groups, where the above-mentioned electron-deficient heteroaryl groups are preferably selected from pyridine, pyrimidine, pyridazine, pyrazine, triazine and benzimidazole, each of which may be substituted by one or more of the radicals defined above, and where the above-mentioned aromatic or heteroaromatic ring systems are preferably selected from naphthyl, anthracenyl, phenanthrenyl, benzanthracenyl, pyrenyl, biphenyl, terphenyl and quaterphenyl, each of which may be substituted by one or more of the radicals defined above, and where the above-mentioned arylamine compounds preferably represent compounds of the following formula (A)

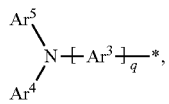

formula (A)

where the symbol * marks the bond to the remainder of the compound and furthermore $Ar^3$, $Ar^4$, $Ar^5$ are as defined above, $Ar^4$ and $Ar^5$ may be linked to one another by a single bond or by a divalent group Y, and q can be equal to 0, 1, 2, 3, 4 or 5.

Examples of compounds for use in the electronic devices according to the invention are shown in the following table:

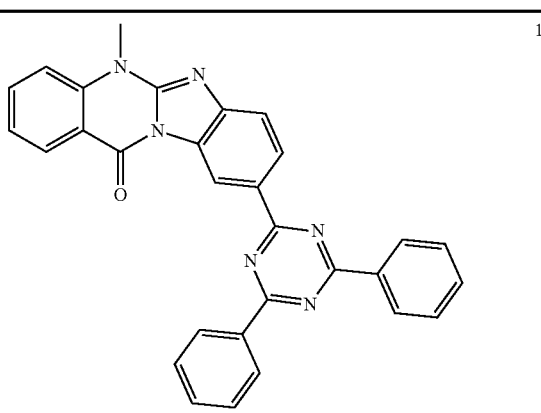

1

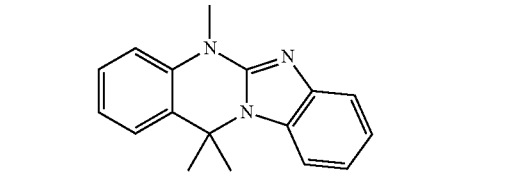 [SMILES: CN1c2ccccc2C(C)(C)n2c1nc1ccccc12]

2

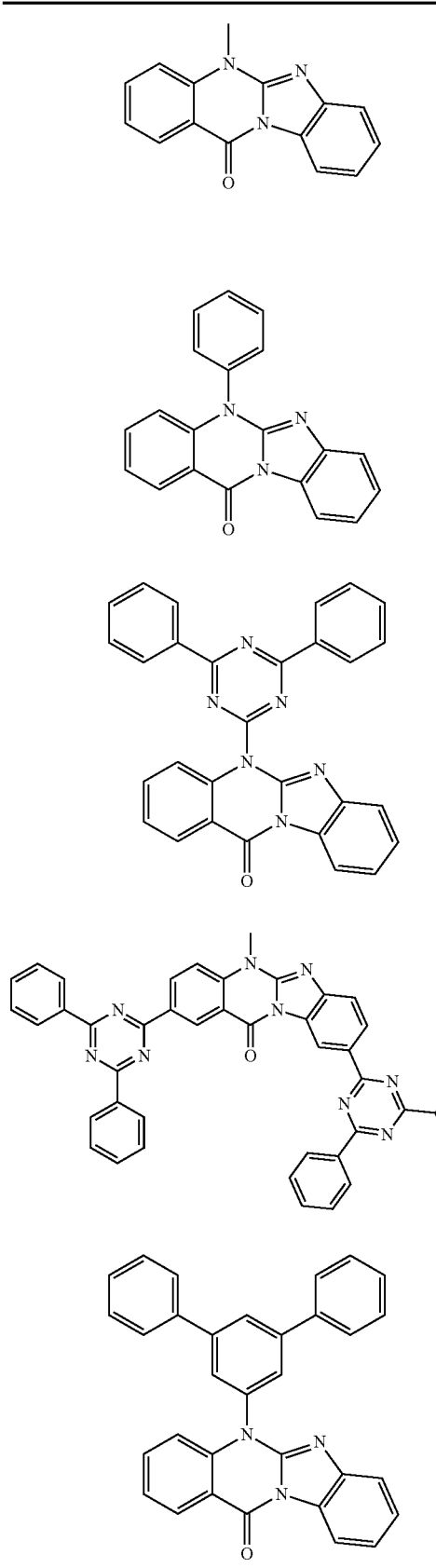
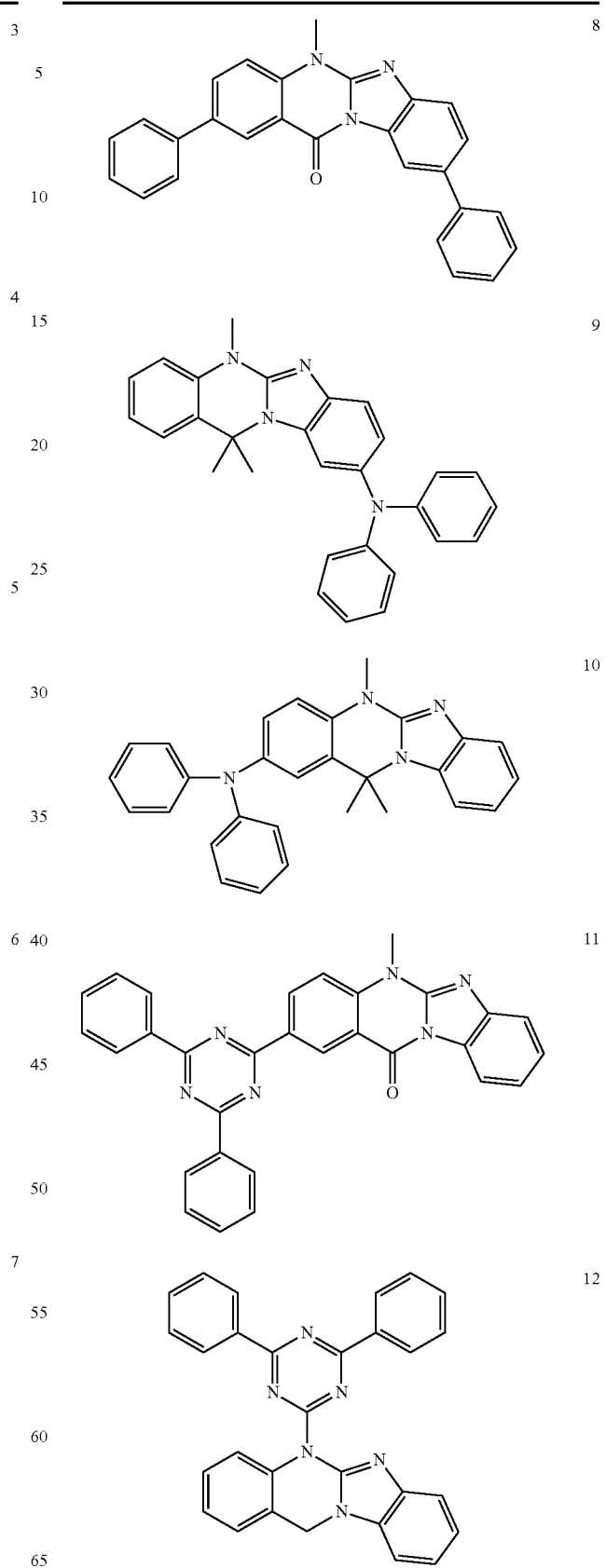

-continued
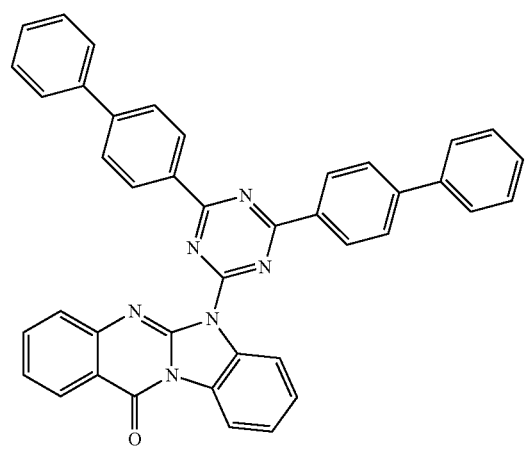 [SMILES: O=c1c2ccccc2nc2n(-c3nc(-c4ccc(-c5ccccc5)cc4)nc(-c4ccc(-c5ccccc5)cc4)n3)c3ccccc3n12]
13
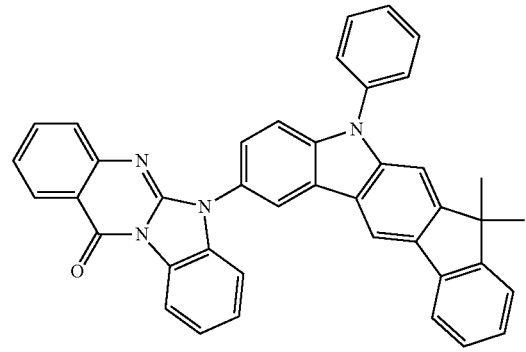 [SMILES: CC1(C)c2ccccc2-c2cc3c4cc(-n5c6ccccc6n6c(=O)c7ccccc7nc56)ccc4n(-c4ccccc4)c3cc21]
14
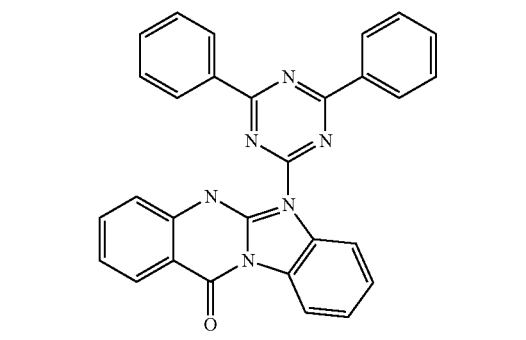
15
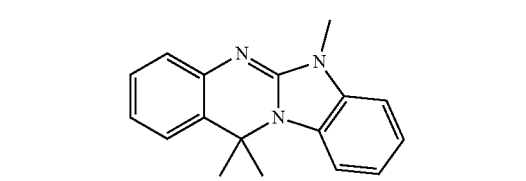 [SMILES: CN1C2=Nc3ccccc3C(C)(C)N2c2ccccc21]
16
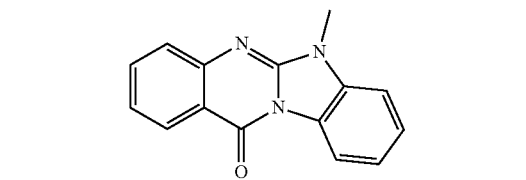 [SMILES: Cn1c2ccccc2n2c(=O)c3ccccc3nc12]
17
-continued
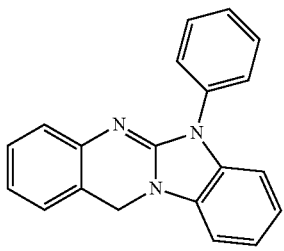 [SMILES: c1ccc(N2C3=Nc4ccccc4CN3c3ccccc32)cc1]
18
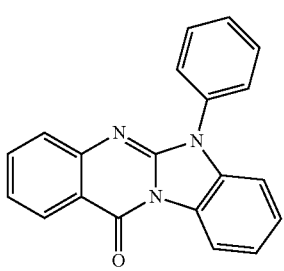 [SMILES: O=c1c2ccccc2nc2n(-c3ccccc3)c3ccccc3n12]
19
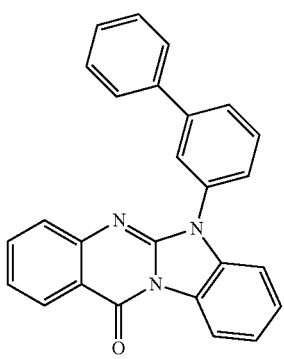 [SMILES: O=c1c2ccccc2nc2n(-c3cccc(-c4ccccc4)c3)c3ccccc3n12]
20
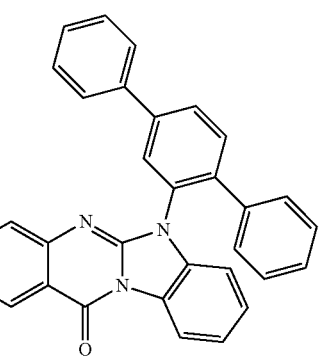
21

22
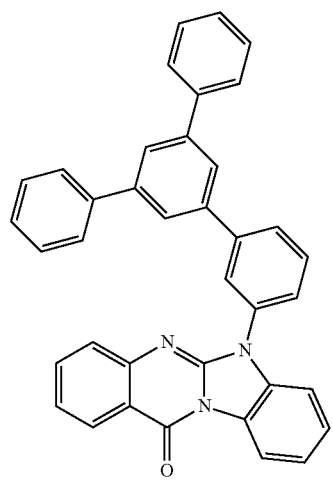 [SMILES: O=c1c2ccccc2nc2n(-c3cccc(-c4cc(-c5ccccc5)cc(-c5ccccc5)c4)c3)c3ccccc3n12]
23
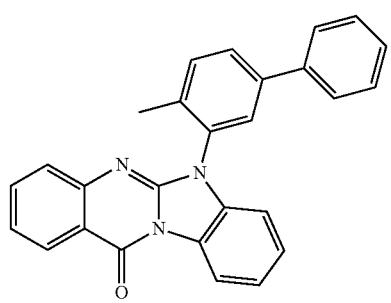 [SMILES: Cc1ccc(-c2ccccc2)cc1-n1c2ccccc2n2c(=O)c3ccccc3nc12]
24
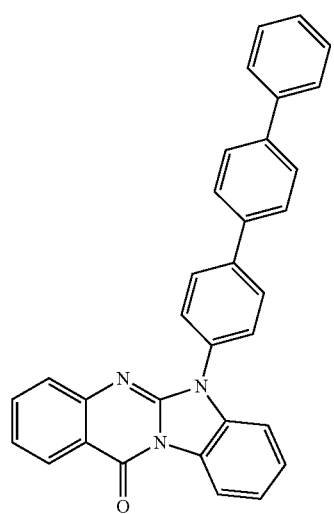 [SMILES: O=c1c2ccccc2nc2n(-c3ccc(-c4ccc(-c5ccccc5)cc4)cc3)c3ccccc3n12]
25
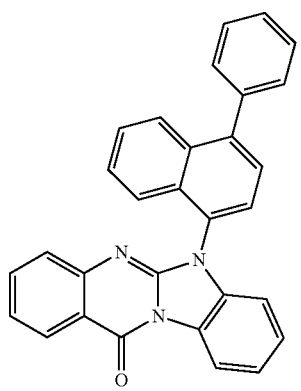 [SMILES: O=c1c2ccccc2nc2n(-c3ccc(-c4ccccc4)c4ccccc34)c3ccccc3n12]
26
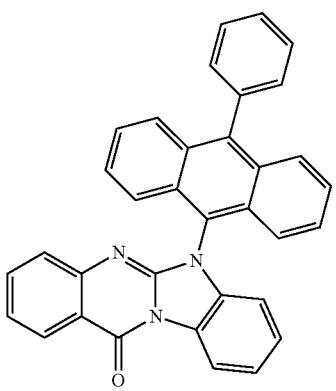 [SMILES: O=c1c2ccccc2nc2n(-c3c4ccccc4c(-c4ccccc4)c4ccccc34)c3ccccc3n12]
27
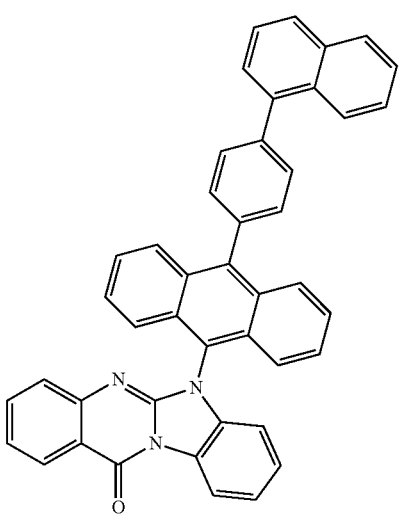 [SMILES: O=c1c2ccccc2nc2n(-c3c4ccccc4c(-c4ccc(-c5cccc6ccccc56)cc4)c4ccccc34)c3ccccc3n12]

28
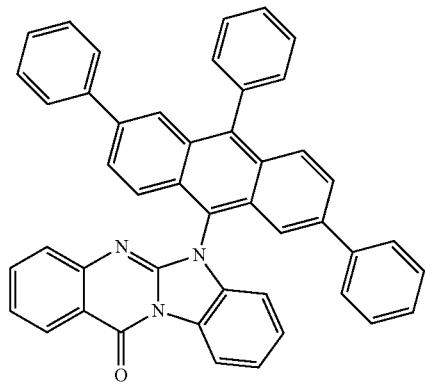 [SMILES: O=c1c2ccccc2nc2n(-c3c4ccc(-c5ccccc5)cc4c(-c4ccccc4)c4ccc(-c5ccccc5)cc34)c3ccccc3n12]
29
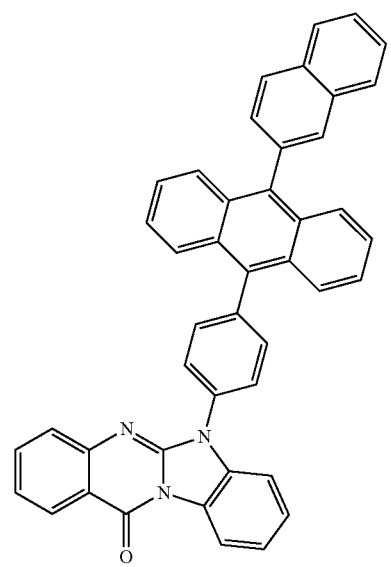 [SMILES: O=c1c2ccccc2nc2n(-c3ccc(-c4c5ccccc5c(-c5ccc6ccccc6c5)c5ccccc45)cc3)c3ccccc3n12]
30
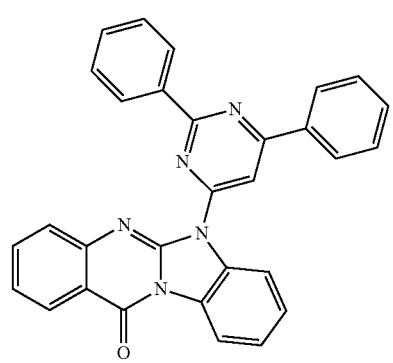
31
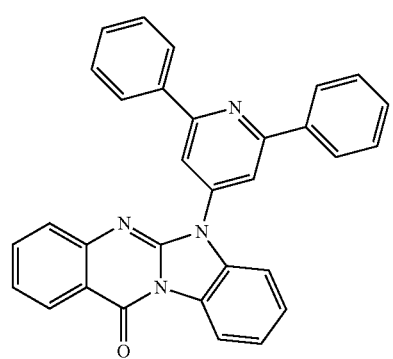
32
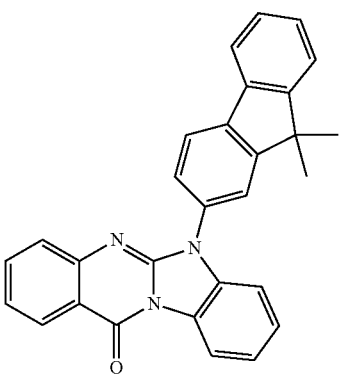 [SMILES: CC1(C)c2ccccc2-c2ccc(-n3c4ccccc4n4c(=O)c5ccccc5nc34)cc21]
33
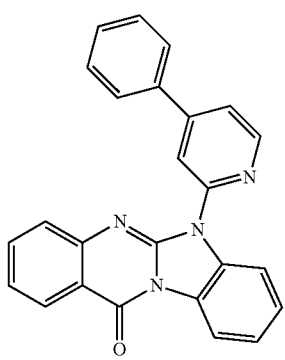 [SMILES: O=c1c2ccccc2nc2n(-c3cc(-c4ccccc4)ccn3)c3ccccc3n12]
34
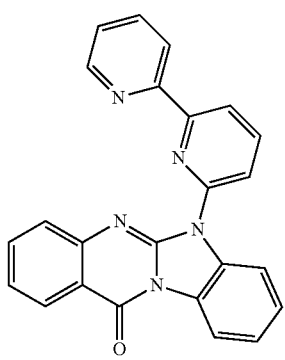 [SMILES: O=c1c2ccccc2nc2n(-c3cccc(-c4ccccn4)n3)c3ccccc3n12]
35
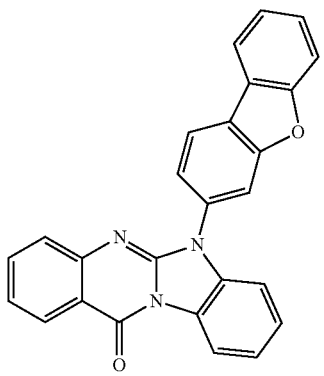 [SMILES: O=c1c2ccccc2nc2n(-c3ccc4c(c3)oc3ccccc34)c3ccccc3n12]

36
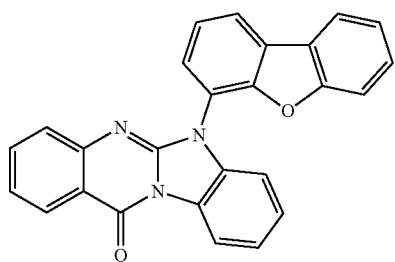 [SMILES: O=c1c2ccccc2nc2n(-c3cccc4c3oc3ccccc34)c3ccccc3n12]
37
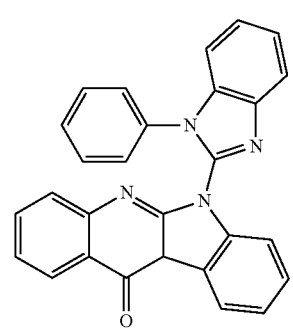 [SMILES: O=C1c2ccccc2N=C2C1c1ccccc1N2c1nc2ccccc2n1-c1ccccc1]
38
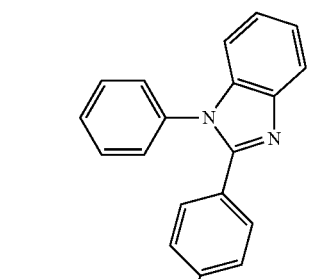
39
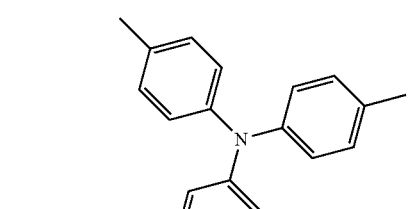
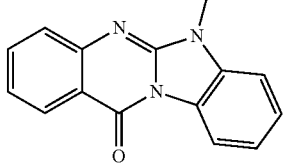
40
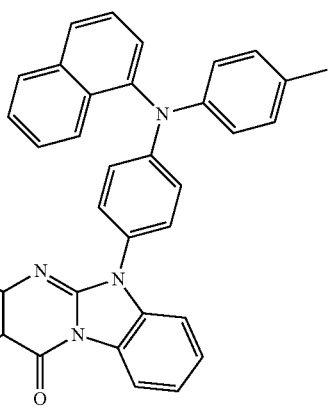
41
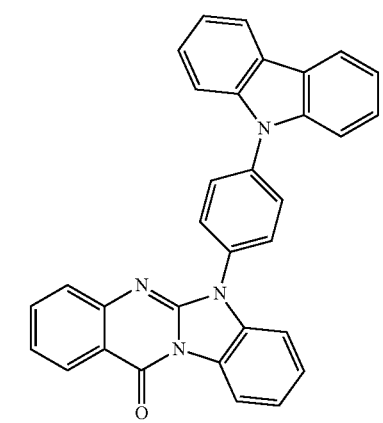 [SMILES: O=c1c2ccccc2nc2n(-c3ccc(-n4c5ccccc5c5ccccc54)cc3)c3ccccc3n12]
42
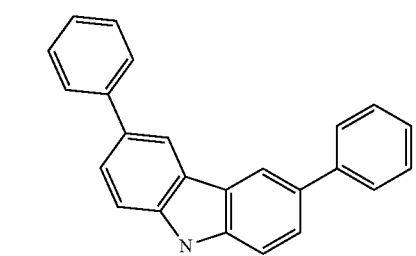
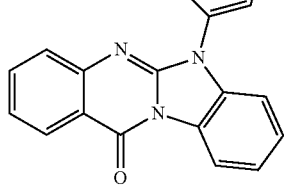

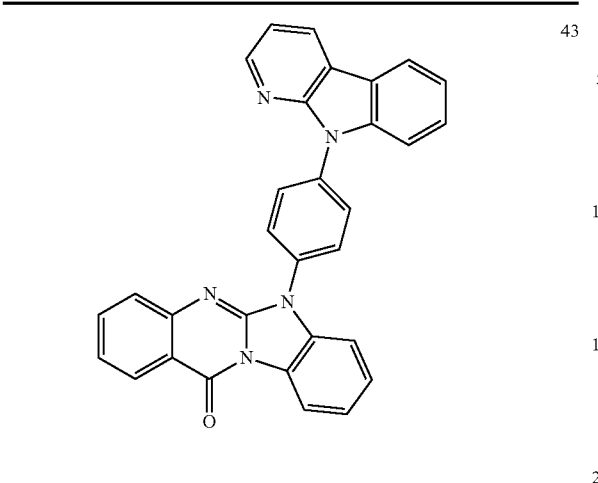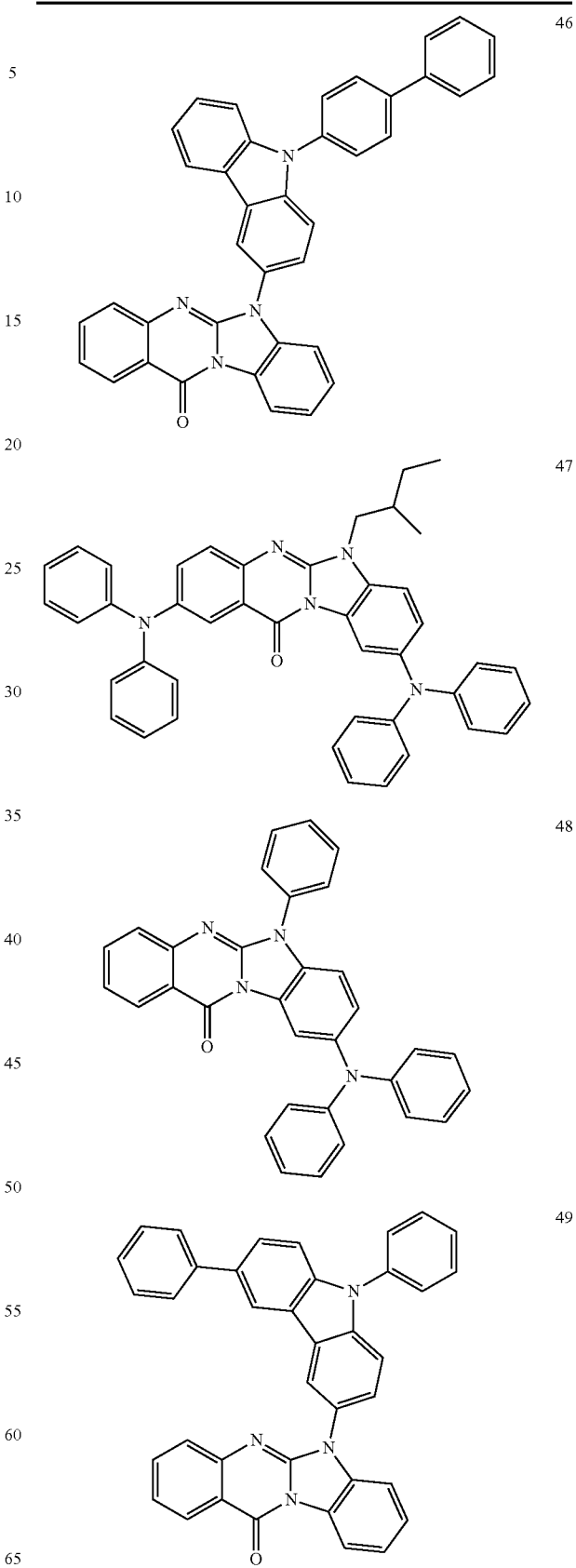

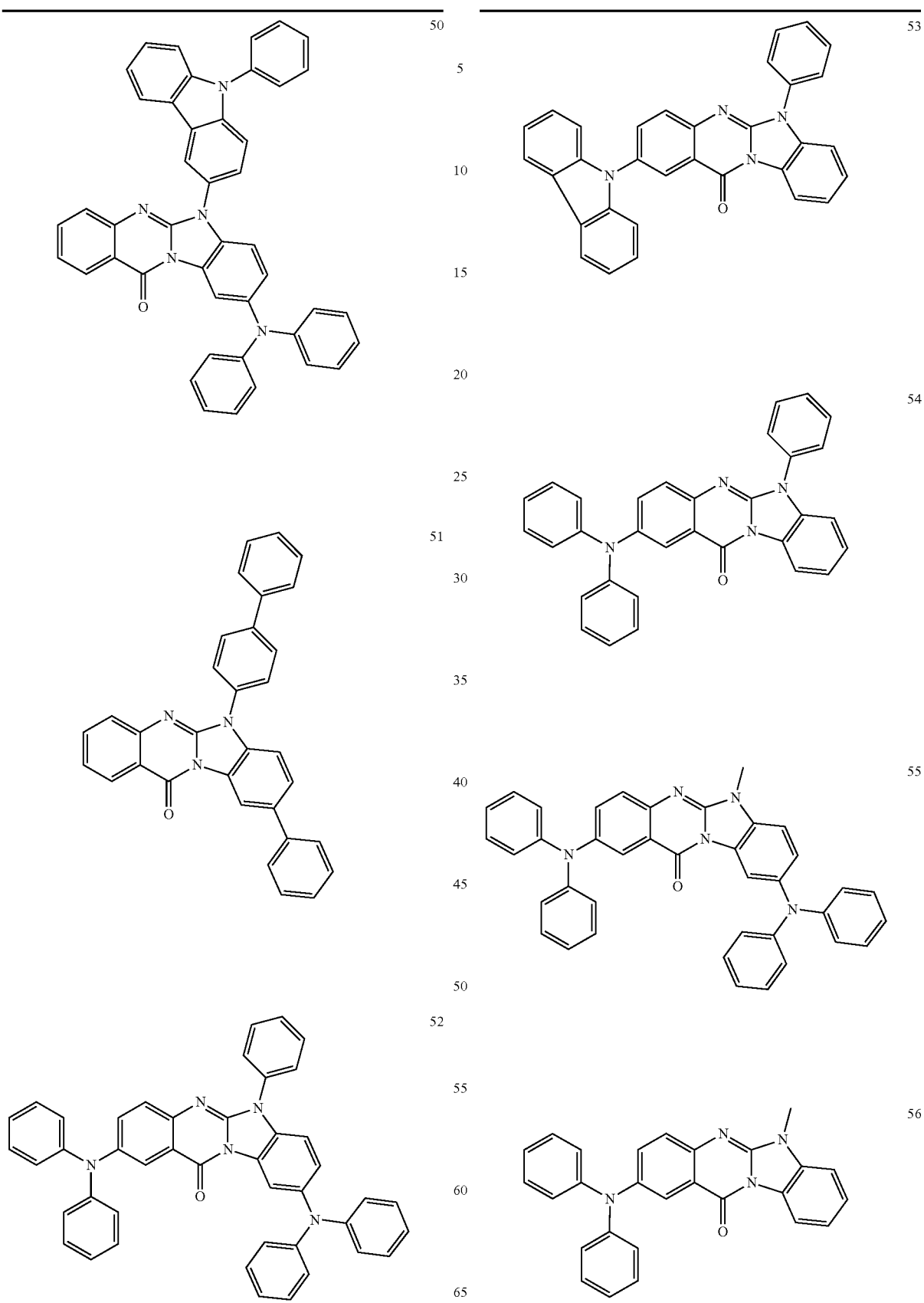

57 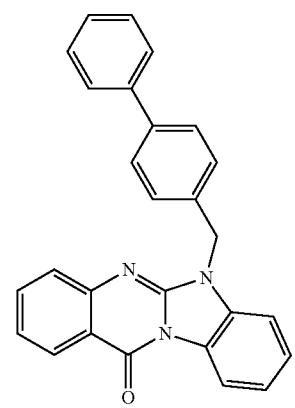 [SMILES: O=c1c2ccccc2nc2n(Cc3ccc(-c4ccccc4)cc3)c3ccccc3n12]
58 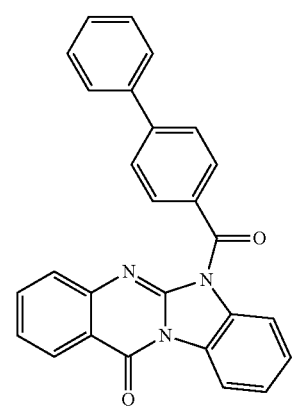 [SMILES: O=C(c1ccc(-c2ccccc2)cc1)n1c2ccccc2n2c(=O)c3ccccc3nc12]
59 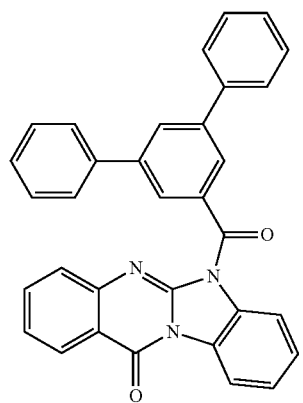 [SMILES: O=C(c1cc(-c2ccccc2)cc(-c2ccccc2)c1)n1c2ccccc2n2c(=O)c3ccccc3nc12]
60 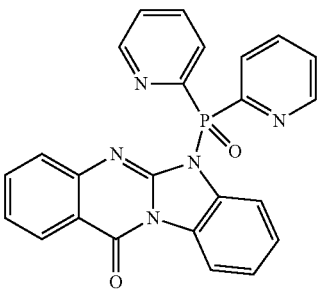 [SMILES: O=c1c2ccccc2nc2n(P(=O)(c3ccccn3)c3ccccn3)c3ccccc3n12]
61 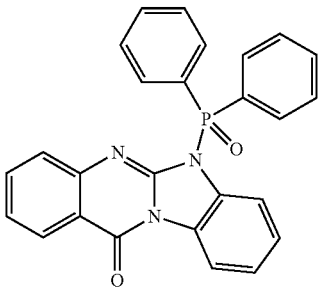 [SMILES: O=c1c2ccccc2nc2n(P(=O)(c3ccccc3)c3ccccc3)c3ccccc3n12]
62 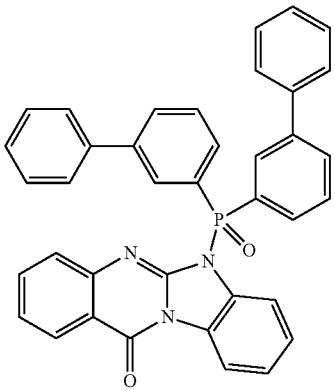 [SMILES: O=c1c2ccccc2nc2n(P(=O)(c3cccc(-c4ccccc4)c3)c3cccc(-c4ccccc4)c3)c3ccccc3n12]
63 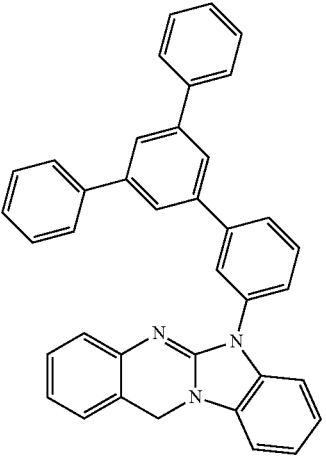 [SMILES: c1ccc(-c2cc(-c3ccccc3)cc(-c3cccc(N4C5=Nc6ccccc6CN5c5ccccc54)c3)c2)cc1]
64 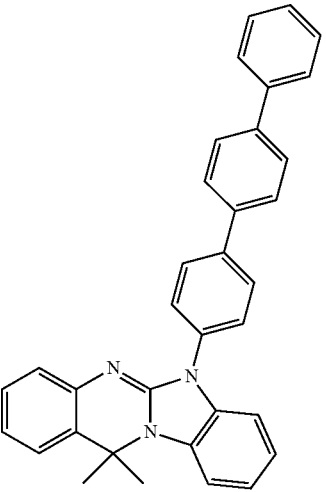 [SMILES: CC1(C)c2ccccc2N=C2N(c3ccc(-c4ccc(-c5ccccc5)cc4)cc3)c3ccccc3N21]

65
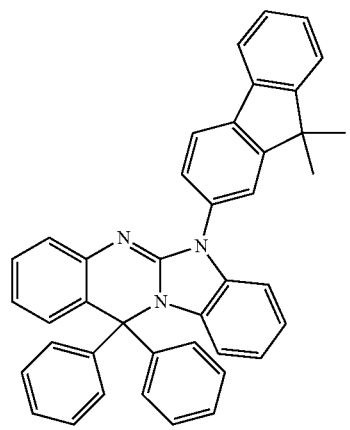 [SMILES: CC1(C)c2ccccc2-c2ccc(N3C4=Nc5ccccc5C(c5ccccc5)(c5ccccc5)N4c4ccccc43)cc21]
66
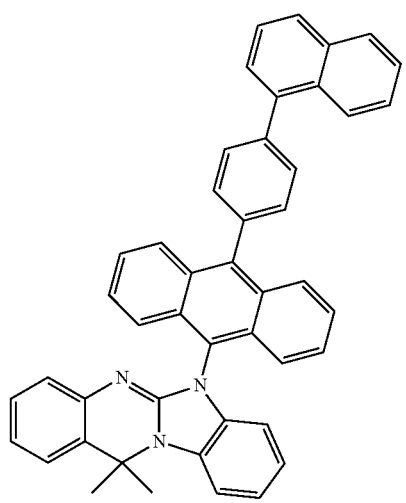 [SMILES: CC1(C)c2ccccc2N=C2N(c3c4ccccc4c(-c4ccc(-c5cccc6ccccc56)cc4)c4ccccc34)c3ccccc3N21]
67
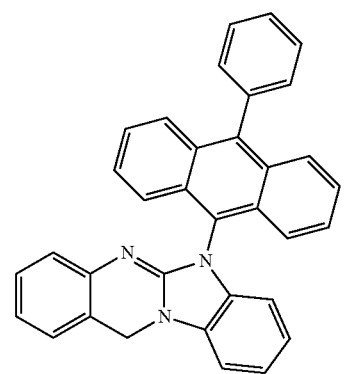 [SMILES: c1ccc(-c2c3ccccc3c(N3C4=Nc5ccccc5CN4c4ccccc43)c3ccccc23)cc1]
68
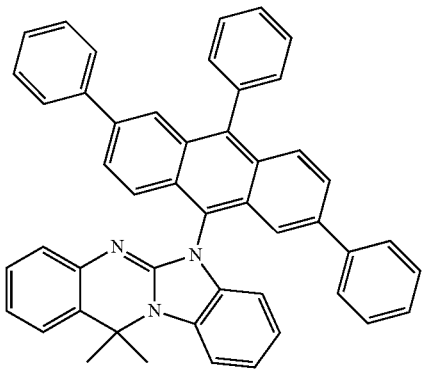 [SMILES: CC1(C)c2ccccc2N=C2N(c3c4ccc(-c5ccccc5)cc4c(-c4ccccc4)c4ccc(-c5ccccc5)cc34)c3ccccc3N21]
69
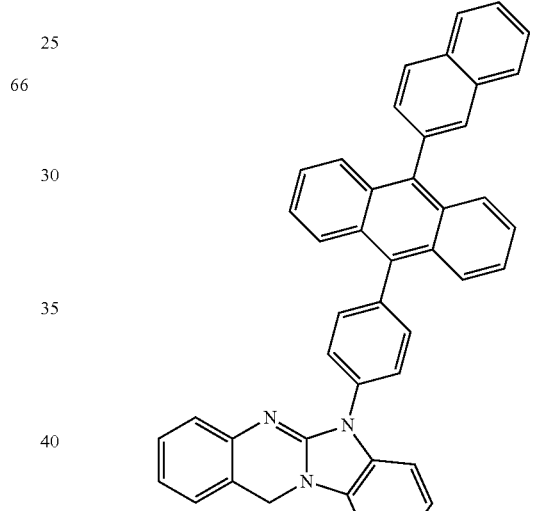
70
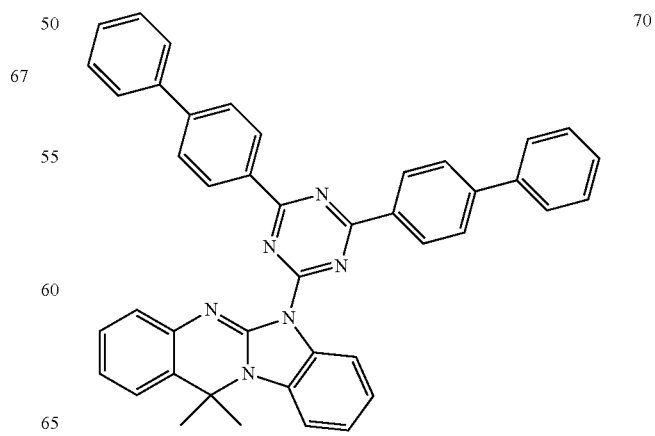

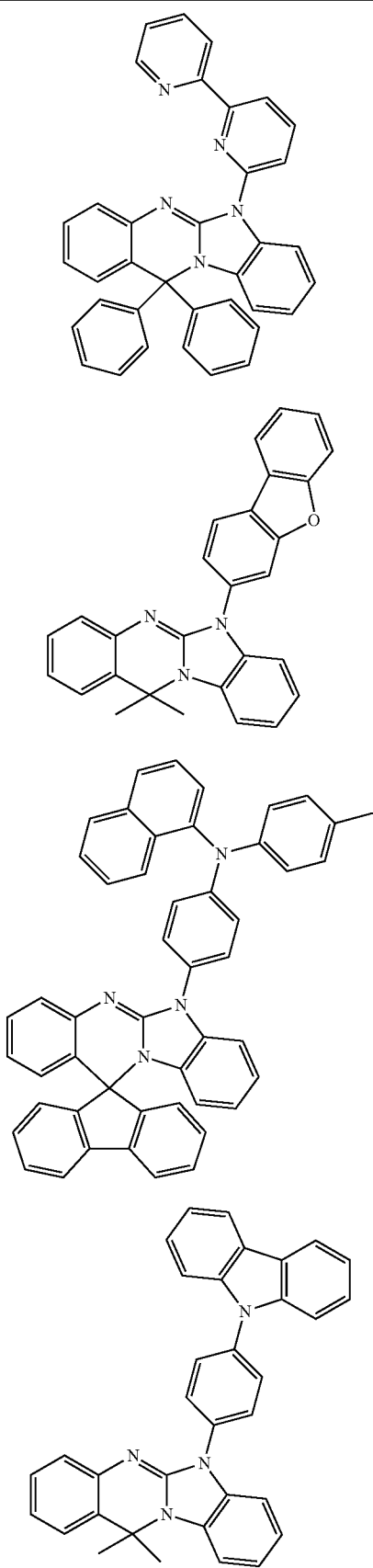
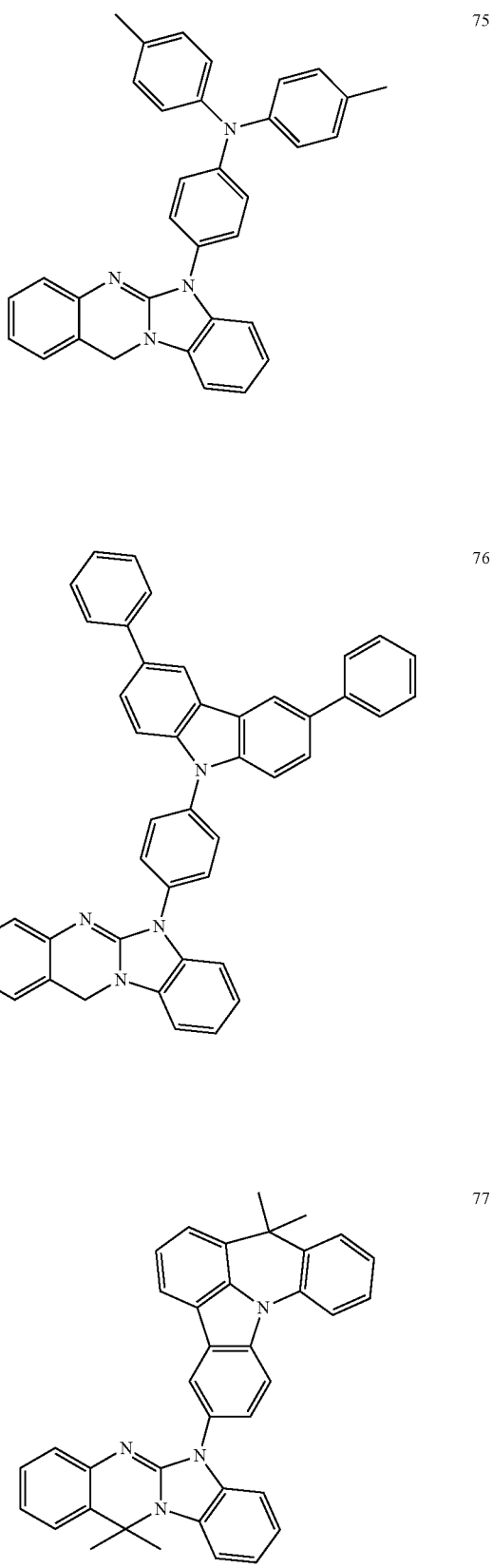

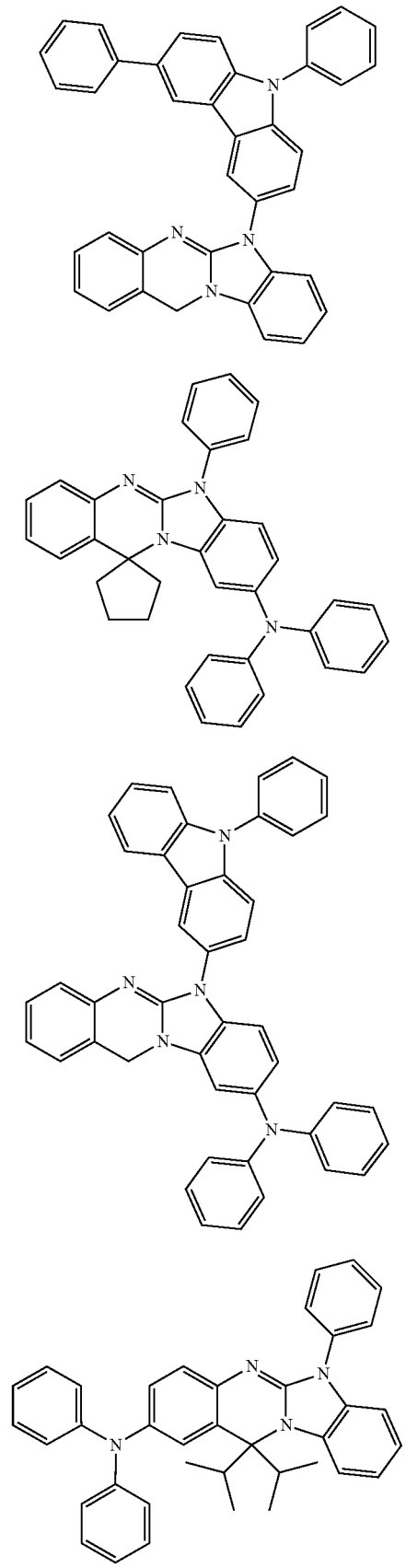
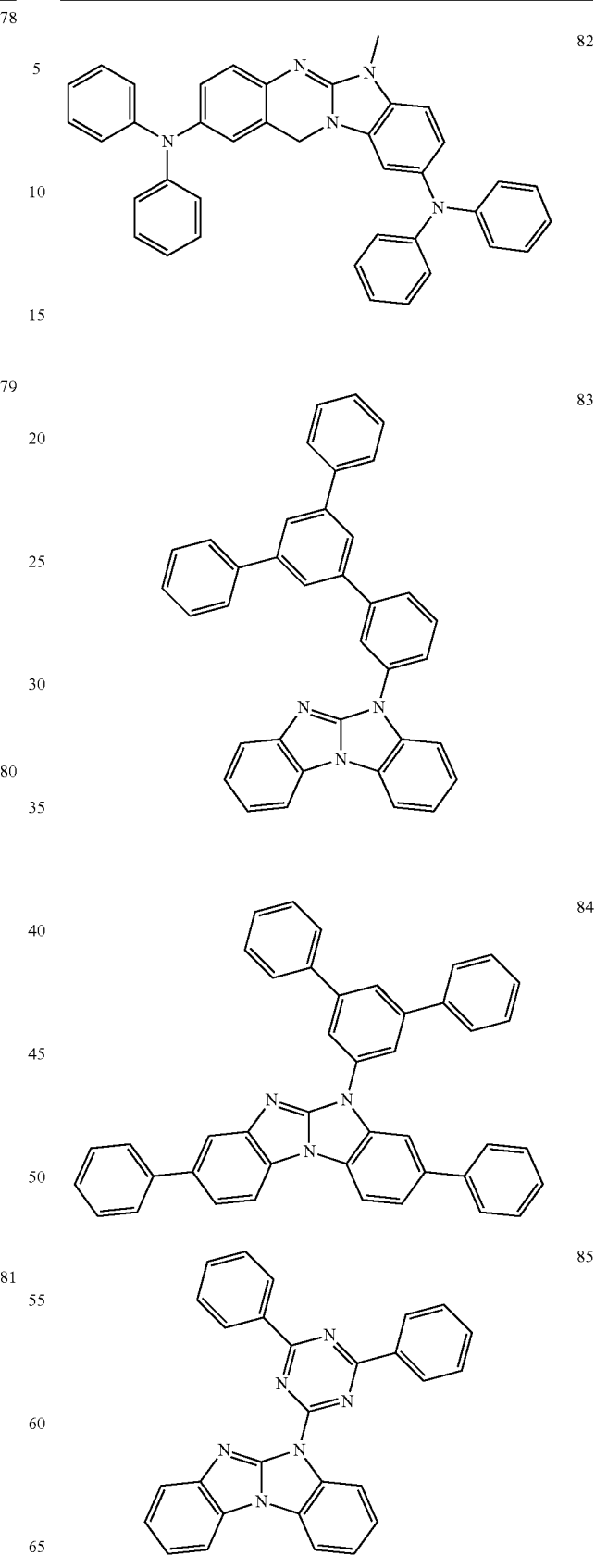

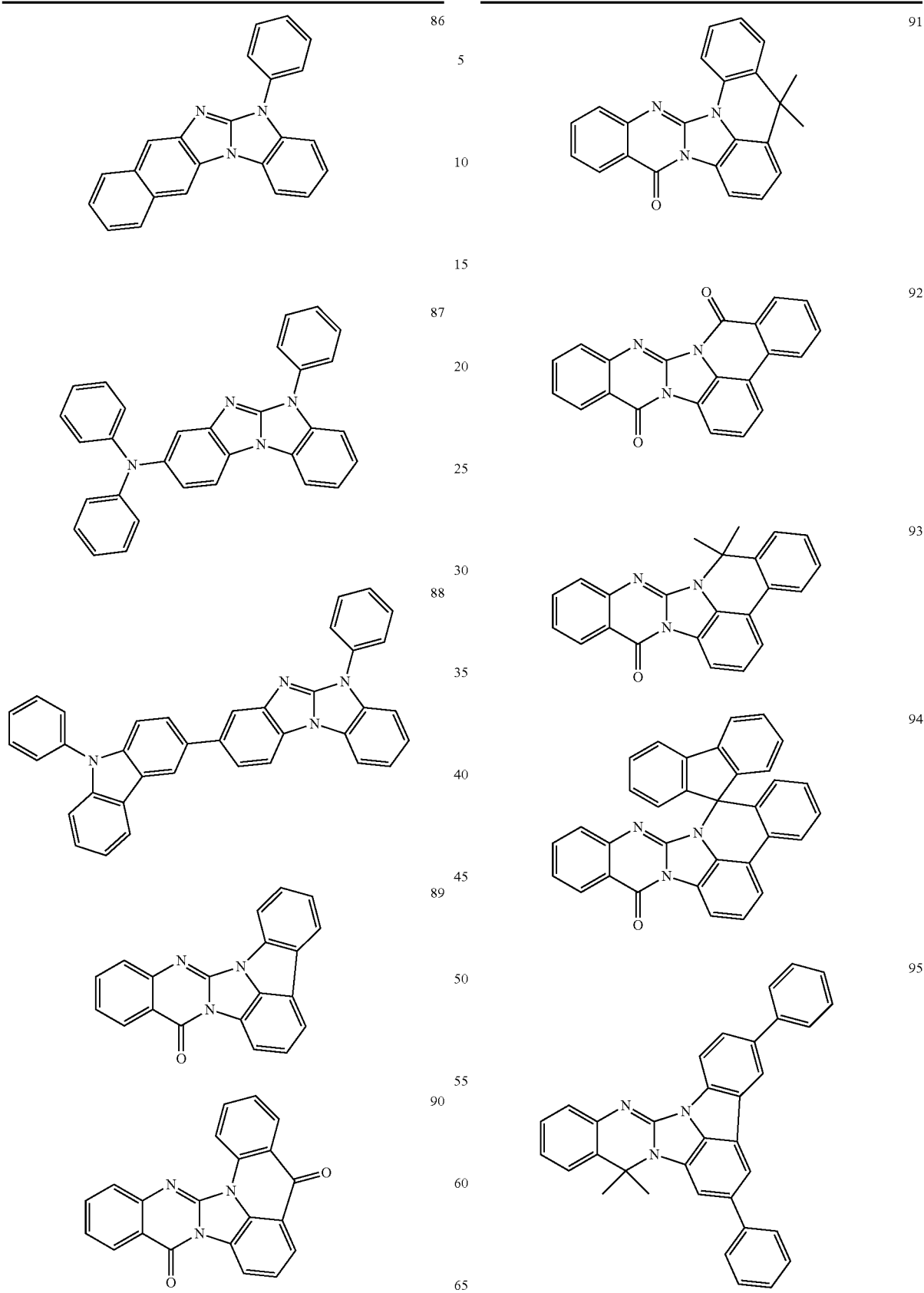

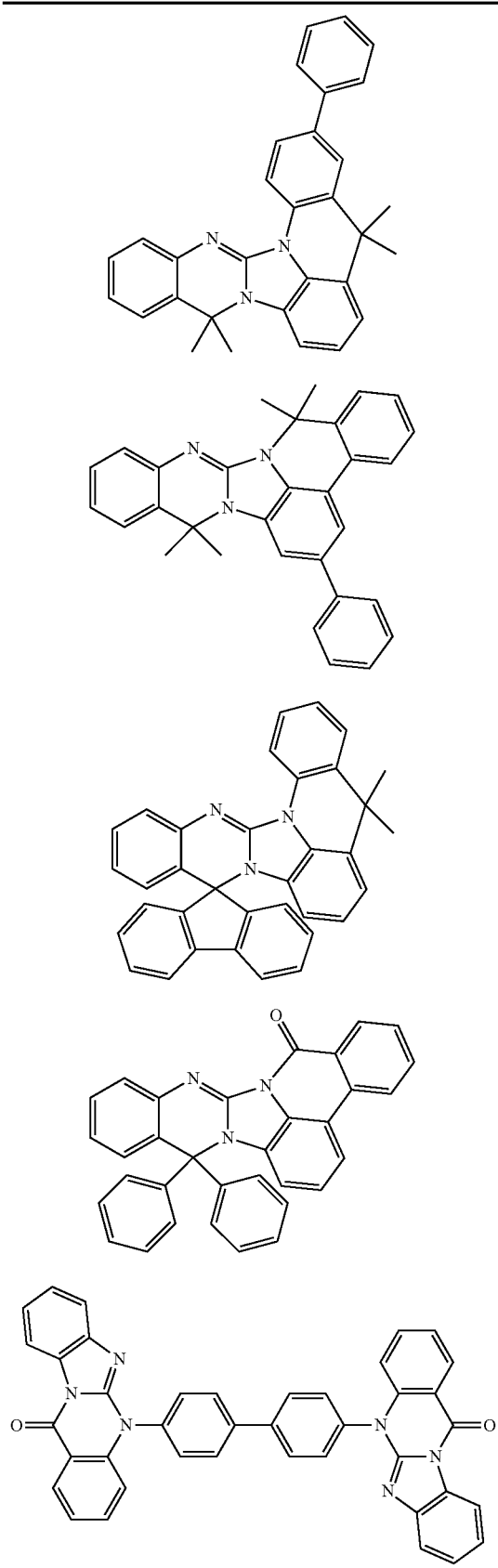
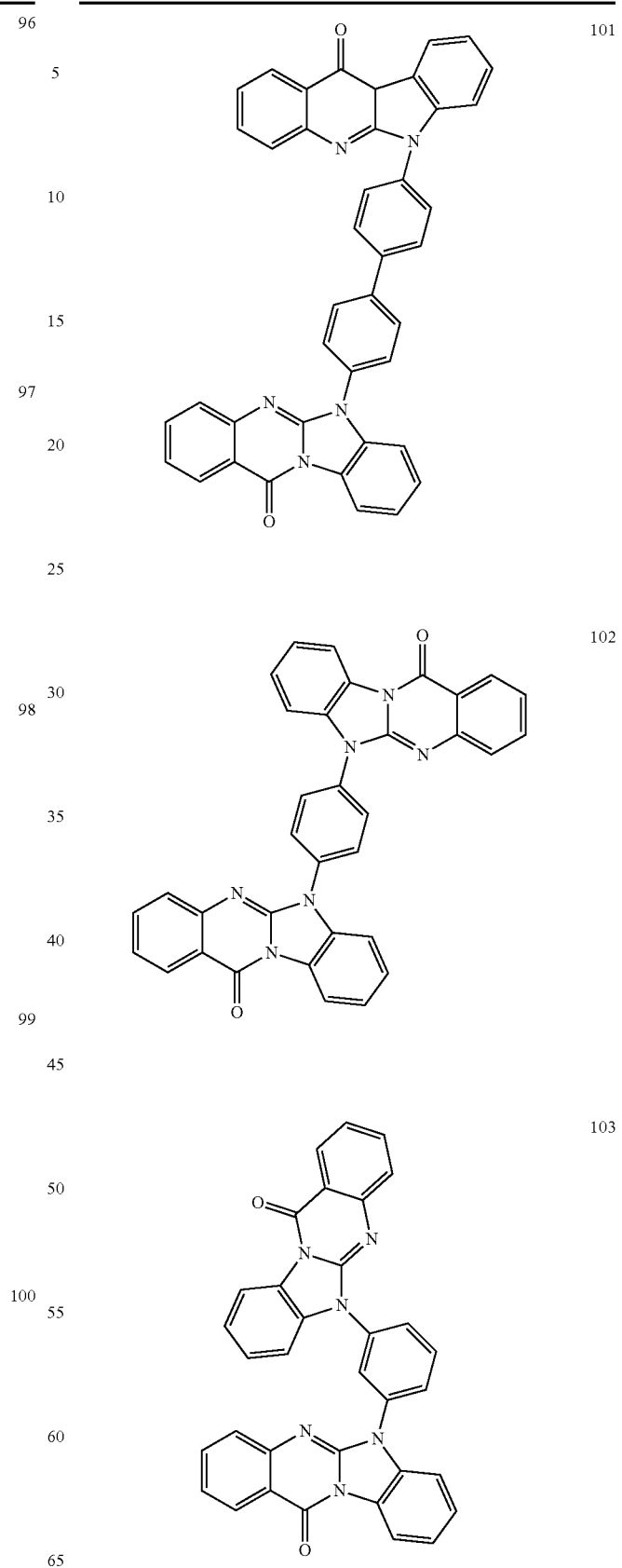

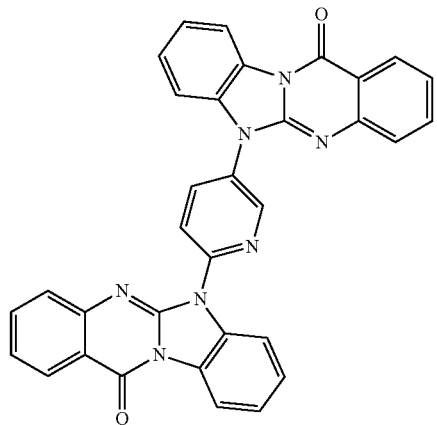 [SMILES: O=c1c2ccccc2nc2n(-c3ccc(-n4c5ccccc5n5c(=O)c6ccccc6nc45)nc3)c3ccccc3n12]
104
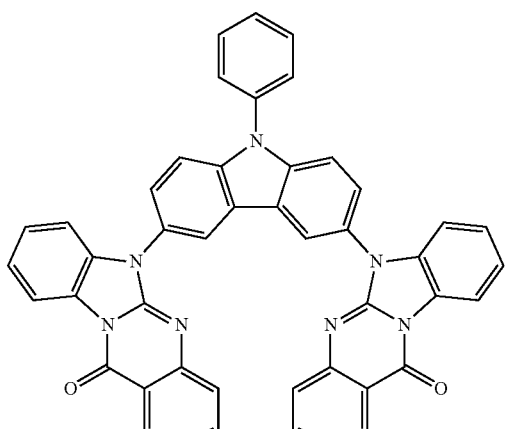
107
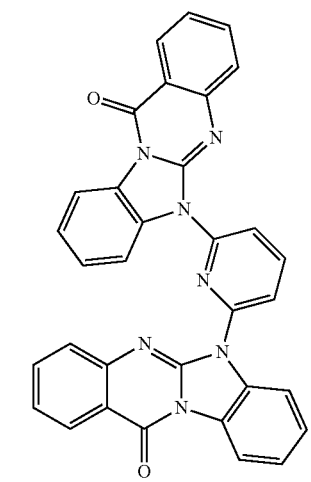 [SMILES: O=c1c2ccccc2nc2n(-c3cccc(-n4c5ccccc5n5c(=O)c6ccccc6nc45)n3)c3ccccc3n12]
105
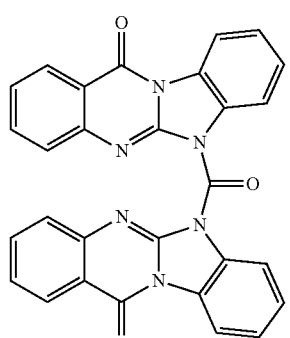
108
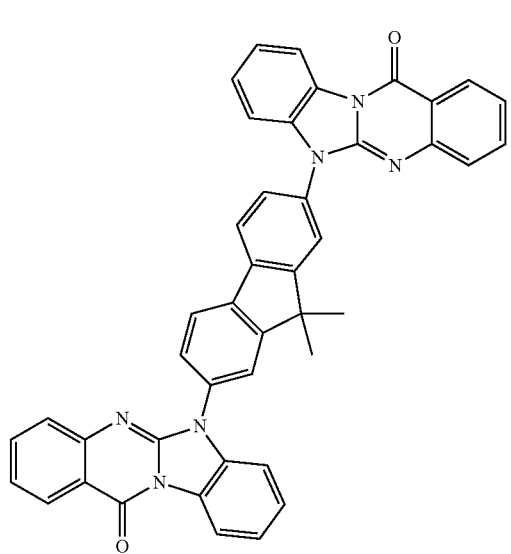 [SMILES: CC1(C)c2cc(-n3c4ccccc4n4c(=O)c5ccccc5nc34)ccc2-c2ccc(-n3c4ccccc4n4c(=O)c5ccccc5nc34)cc21]
106
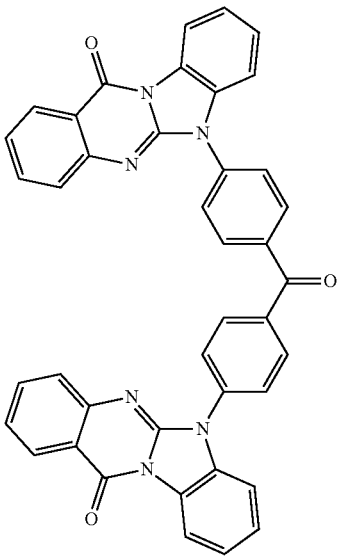 [SMILES: O=C(c1ccc(-n2c3ccccc3n3c(=O)c4ccccc4nc23)cc1)c1ccc(-n2c3ccccc3n3c(=O)c4ccccc4nc23)cc1]
109

-continued

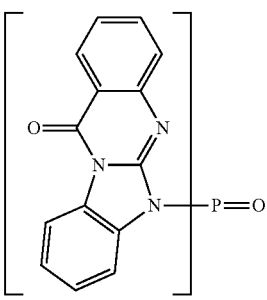

110

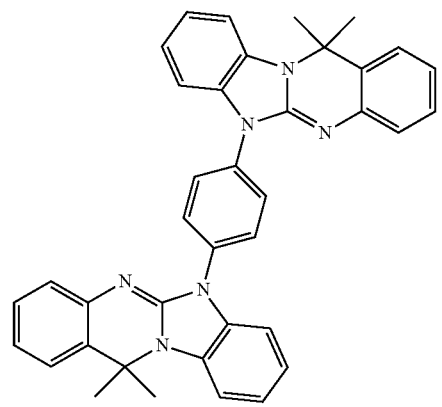 [SMILES: CC1(C)c2ccccc2N=C2N(c3ccc(N4C5=Nc6ccccc6C(C)(C)N5c5ccccc54)cc3)c3ccccc3N21]

111

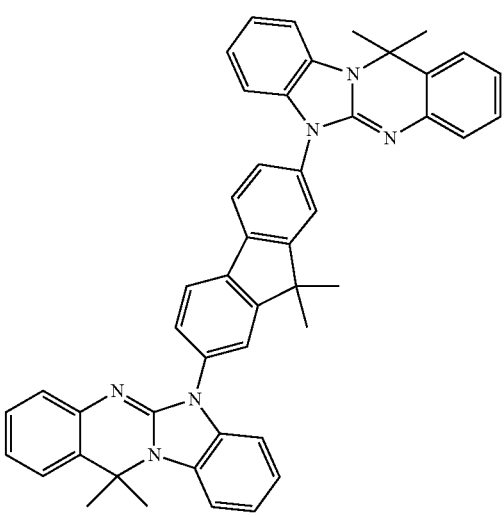 [SMILES: CC1(C)c2cc(N3C4=Nc5ccccc5C(C)(C)N4c4ccccc43)ccc2-c2ccc(N3C4=Nc5ccccc5C(C)(C)N4c4ccccc43)cc21]

112

-continued

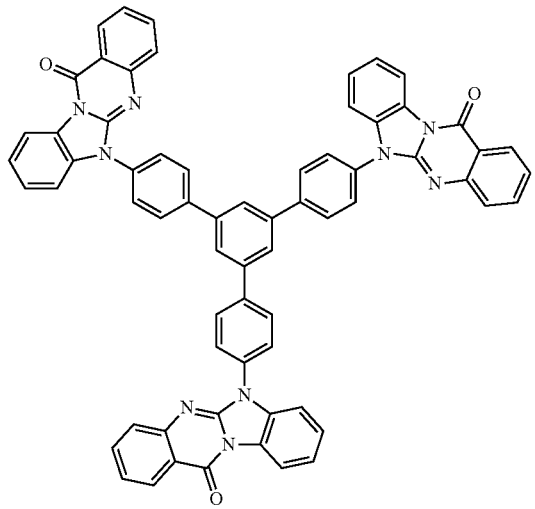 [SMILES: O=c1c2ccccc2nc2n(-c3ccc(-c4cc(-c5ccc(-n6c7ccccc7n7c(=O)c8ccccc8nc67)cc5)cc(-c5ccc(-n6c7ccccc7n7c(=O)c8ccccc8nc67)cc5)c4)cc3)c3ccccc3n12]

113

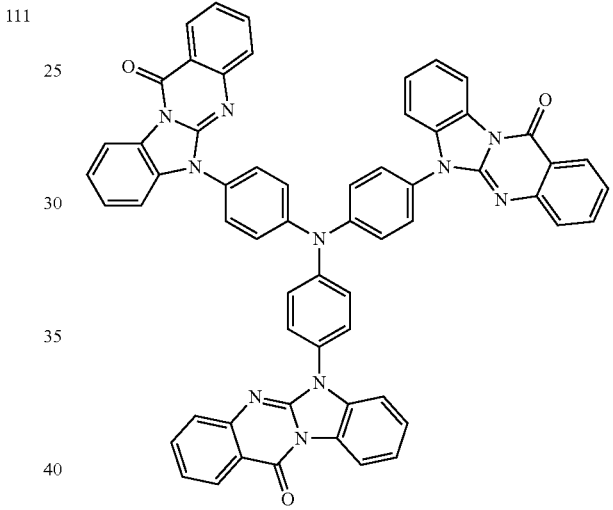

114

The present invention furthermore relates to compounds of the formula (Ic), (IIc), (IIIc) or (IVc), in which R is defined as follows:

R is an aromatic or heteroaromatic ring system having 5 to 20 aromatic ring atoms, which may in each case be substituted by one or more radicals $R^1$, or an aralkyl or heteroaralkyl group having 5 to 20 aromatic ring atoms, which may be substituted by one or more radicals $R^1$, where the radical R may furthermore be linked to an adjacent group $Ar^1$ or $Ar^2$ via a single bond or via a divalent group Y.

The above-mentioned preferred embodiments of the compounds of the formula (Ic) to (IVc) are likewise preferred in this connection.

Particular preference is given to the embodiments of the formulae (V) to (X) and (V-1) to (V-6), (VI-1) to (VI-2), (VII-1) to (VII-6), (VIII-1) to (VIII-2), (IX-1) to (IX-3) and (X-1).

In an even more preferred embodiment of the compounds according to the invention, R is an aryl or heteroaryl group having 5 to 20 aromatic ring atoms, which may in each case be substituted by one or more radicals $R^1$.

The compounds according to the invention can be prepared by synthetic steps known to the person skilled in the art, such as, for example, bromination, Suzuki coupling, Hartwig-Buchwald coupling, etc.

Examples of synthetic routes which lead to the compounds according to the invention will be shown below.

5- or 6-substituted benzimidazo[2,1-b]quinazolin-12(6H)-ones can be obtained from the parent structure benzimidazo[2,1-b]quinazolin-12(6H)-one (CAS [4149-00-2], cf. patent application SU 1182043) by deprotonation using bases in aprotic or protic media with generation of the corresponding anion and reaction thereof with electrophiles ("E+") (Scheme 1).

Scheme 1

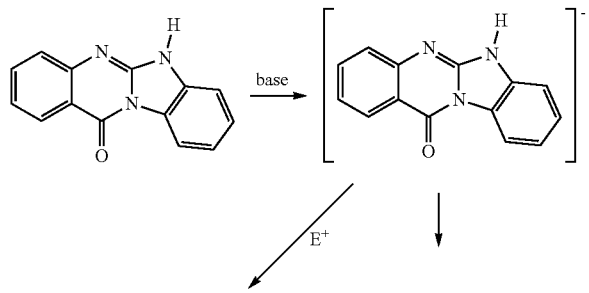

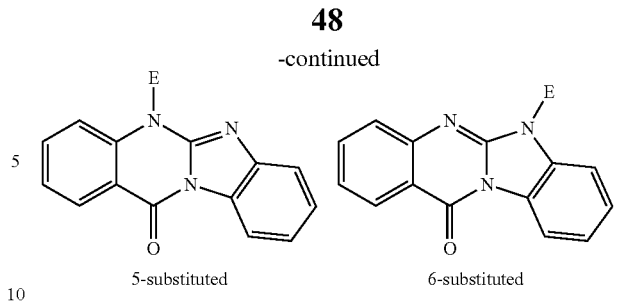

5-substituted    6-substituted

In aprotic solvents, such as, for example, DMF, NMP, DMSO and ether, the 6-isomers are typically obtained regioselectively, whereas the 5-isomers are obtained in protic solvents. Electrophiles which can be used are a wide range of classes of compound, such as, for example, alkyl and aralkyl halides, sulfonates and sulfates, carboxylates, carboxylic anhydrides and carbonyl halides, silicon-halogen compounds, phosphorus-halogen compounds and halogenated electron-deficient heterocycles, such as diazines or triazines (Scheme 2).

Scheme 2

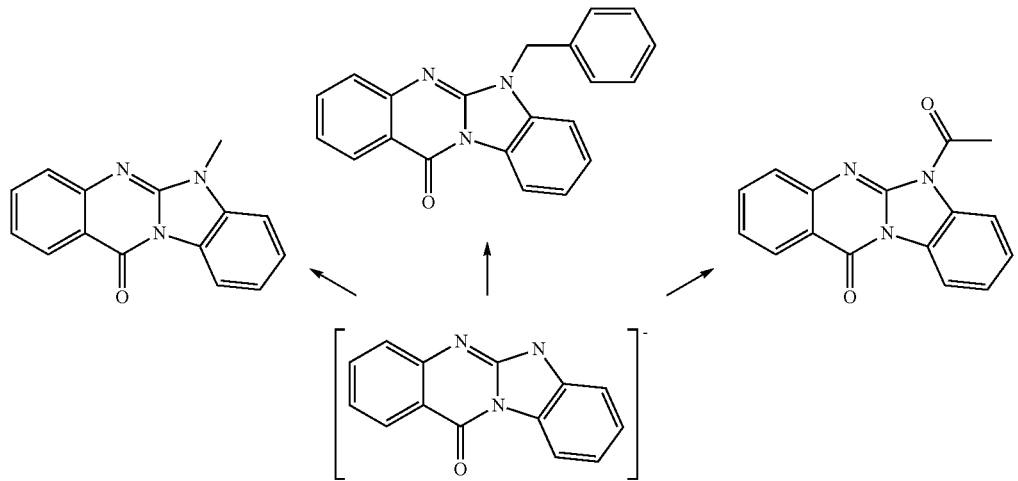

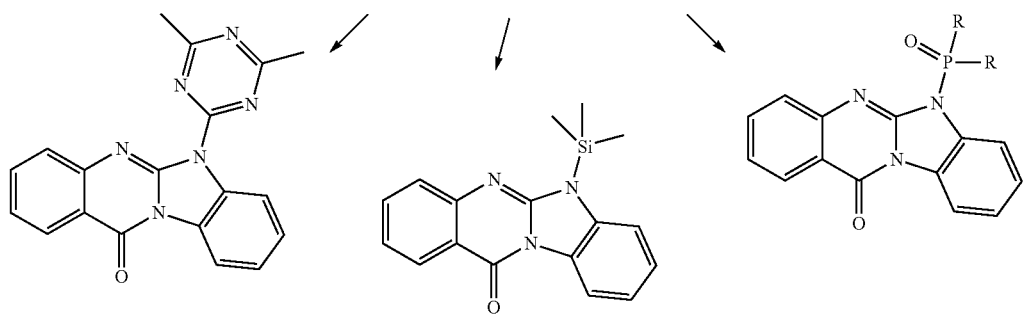

Under the conditions of a palladium- or copper-catalysed C—N coupling, benzimidazo[2,1-b]quinazolin-12(6H)-ones furthermore react to give the 5-aryl-substituted derivatives (Scheme 3). This represents a further possible synthetic route for the preparation of this type of compounds according to the invention.

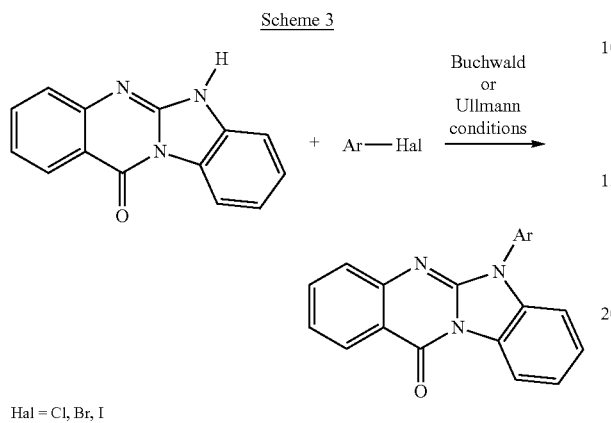

Halogenated benzimidazo[2,1-b]quinazolin-12(6H)-ones (cf. R. D. Carpenter, et al., J. Org. Chem. 2007, 72, 1, 284) can firstly be N-functionalised by the processes shown above and subsequently functionalised further by means of conventional methods of C—C coupling or C—N coupling (Scheme 4). This process is not restricted to the position of the C—C coupling or C—N coupling shown in Scheme 4. The use of isomeric mono-, di- or oligo-bromides of benzimidazo[2,1-b]quinazolin-12(6H)-ones enables the preparation of a multiplicity of derivatives of the compounds shown in Scheme 4 which have a different substitution pattern.

The reduction of the carbonyl function to the parent structure of the 6,12-dihydrobenzimidazo[2,1-b]quinazolines can be carried out, for example, using lithium aluminium hydride under conditions which are familiar to the person skilled in the art (W. H. W. Lunn, J. Org. Chem. 1972, 37, 4, 607, Scheme 5, first line). A reaction with suitable Grignard reagents and subsequent acid-catalysed dehydrating cyclisation results in compounds according to the invention which have a spiro C atom (Scheme 5, second line).

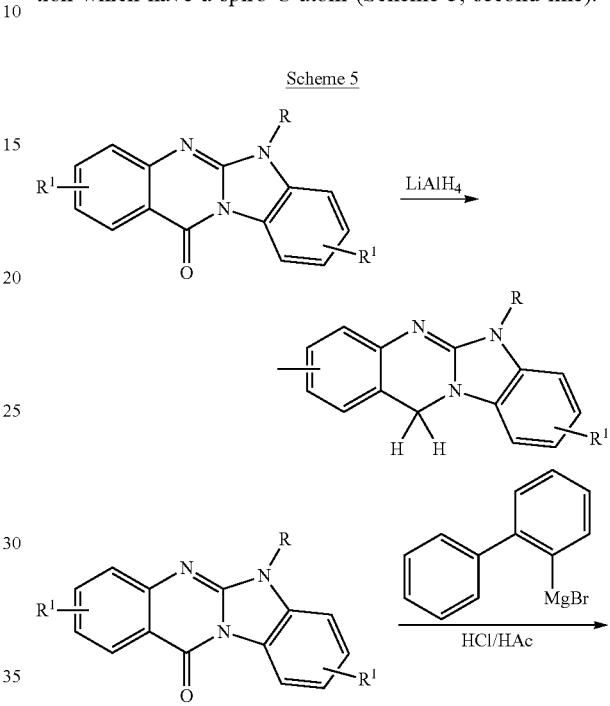

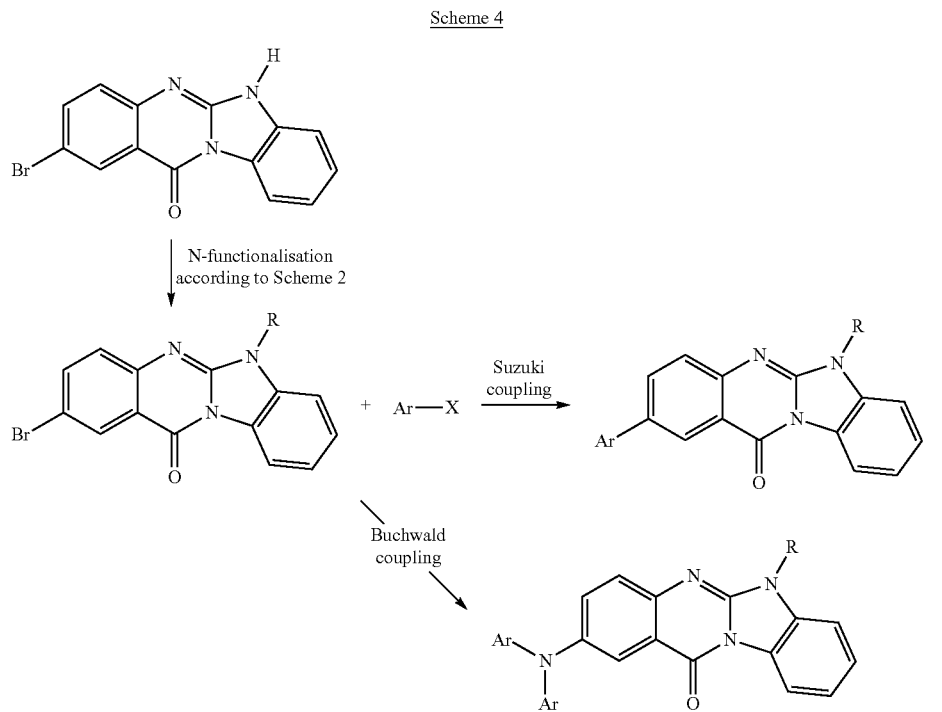

-continued

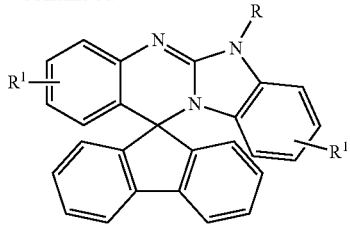

The examples shown above are based on the skeleton of benzimidazo[2,1-b]quinazolin-12(6H)-one (cf. Scheme 1). However, the synthetic methods shown are not restricted to this skeleton. The imidazo[1,2-a]pyrimidin-5(1H)-ones and the pyrimido[1,2-a]benzimidazol-4(10H)-ones and derivatives thereof can also be reacted analogously, enabling the preparation of compounds according to the invention based on these skeletons.

The invention thus furthermore relates to a process for the preparation of the compounds of the formula (Ic) to (IVc) according to the invention, characterised in that at least one of the two steps a) and b) indicated below is carried out:
a) deprotonation at the 5- or 6-N atom of the benzimidazoquinazoline skeleton and subsequent reaction with an electrophilic compound, so that a bond is formed between the 5- or 6-N atom and the electrophilic compound;
b) organometallic coupling under Hartwig-Buchwald or Ullmann conditions between the 5- or 6-N atom of the benzimidazoquinazoline skeleton and an aryl group Ar, which is employed as starting material Ar-Hal, where Hal is any desired suitable leaving group, such as, for example, halide.

The compounds of the formula (Ic) to (IVc) described above, in particular compounds which are substituted by reactive leaving groups, such as bromine, iodine, chlorine, boronic acid or boronic acid ester, can be used as monomers for the preparation of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (Ic) to (IVc), where the bond(s) to the polymer, oligomer or dendrimer may be localised at any desired positions substituted by R or $R^1$ in formula (Ic) to (IVc). Depending on the linking of the compound of the formula (Ic) to (IVc), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (Ic) to (IVc) may be linked directly to one another or they may be linked to one another via a divalent group, for example via a substituted or unsubstituted alkylene group, via a heteroatom or via a divalent aromatic or heteroaromatic group. In branched and dendritic structures, three or more units of the formula (Ic) to (IVc) may, for example, be linked via a trivalent or polyvalent group, for example via a trivalent or polyvalent aromatic or heteroaromatic group, to give a branched or dendritic oligomer or polymer.

The same preferences as described above for compounds of the formula (Ic) to (IVc) apply to the recurring units of the formula (Ic) to (IVc) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (Ic) to (IVc) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

The invention also relates to formulations comprising at least one compound of the formula (Ic) to (IVc) or at least one polymer, oligomer or dendrimer containing at least one unit of the formula (Ic) to (IVc) and at least one solvent, preferably an organic solvent.

The formulations according to the invention are used, for example, in the production of organic electroluminescent devices, which is described in greater detail in a following section.

The compounds of the formula (I) to (IV) are suitable for use in electronic devices, in particular in organic electroluminescent devices (OLEDs). Depending on the substitution, the compounds are employed in various functions and in various layers of the organic electroluminescent device.

Furthermore, the choice of the group X or $X^1$ plays a role in the case of the compounds.

For example, compounds according to the invention which are substituted at least by an arylamino group are particularly suitable for use as hole-transport or hole-injection materials. Furthermore, in the case of compounds for the preferred use as hole-transport or hole-injection materials, it is preferred for X or $X^1$ to represent a group of the formula $C(R^1)_2$ or $NR^1$.

Furthermore, compounds according to the invention which are substituted by at least one electron-deficient heteroaryl group are particularly suitable for use as matrix materials for phosphorescent dopants and/or for use as electron-transport materials. In the case of compounds for the preferred use as matrix materials for phosphorescent dopants and/or as electron-transport materials, it is furthermore preferred for X to represent a single bond or a group of the formula $C=O$, $C=S$, $C=NR^1$, O, S, SO or $SO_2$ or for $X^1$ to represent a group of the formula $C=O$, $C=S$, $C=NR^1$, O, S, SO or $SO_2$.

Furthermore, compounds according to the invention which are substituted by one or more aromatic or heteroaromatic ring systems are particularly suitable for use as fluorescent dopants.

The invention therefore furthermore relates to the use of the compounds of the formula (I) to (IV) in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably organic electroluminescent devices (OLEDs).

The invention furthermore relates, as already mentioned above, to an organic electroluminescent device comprising anode, cathode and at least one organic layer, characterised in that the organic layer comprises a compound of the formula (I) to (IV).

The organic electroluminescent device comprises at least one electroluminescent layer. The electroluminescent layer may comprise a compound of the formula (I) to (IV), but the compound of the formula (I) to (IV) may also be present additionally or exclusively in another layer of the device, for example a hole- or electron-transport layer.

These other layers which may optionally be present in the organic electroluminescent device according to the invention are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or in-organic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to systems having three emitting layers, where at least one of these layers comprises at least one compound of the formula (I) to (IV) and where the three layers exhibit blue, green and orange or red emission (for the basic structure see, for example, WO 2005/011013). Alternatively and/or additionally, the compounds of the formula (I) to (IV) may also be present in the hole-transport layer or another layer. Emitters which have broad-band emission bands and thus exhibit white emission are likewise suitable for white emission.

It is preferred in accordance with the invention for the compound of the formula (I) to (IV) to be employed in an electronic device comprising one or more phosphorescent dopants. The compound here can be used in various layers, preferably in a hole-transport layer, a hole-injection layer or in the emitting layer.

However, the compound of the formula (I) to (IV) can also be employed in accordance with the invention in an electronic device comprising one or more fluorescent dopants.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the emitters described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes without inventive step in combination with the compounds of the formula (I) to (IV) according to the invention in organic electroluminescent devices.

Examples of suitable phosphorescent emitter compounds are furthermore revealed by the following table:

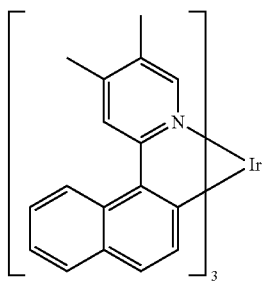
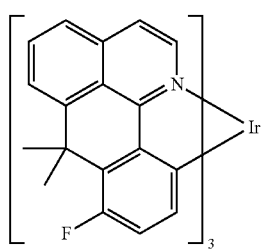
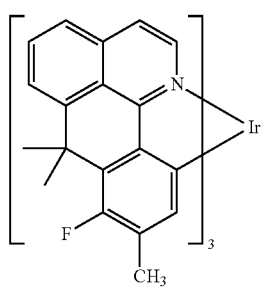
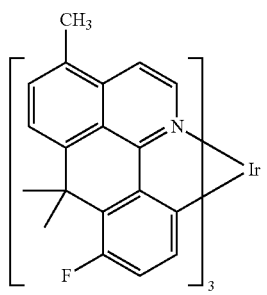
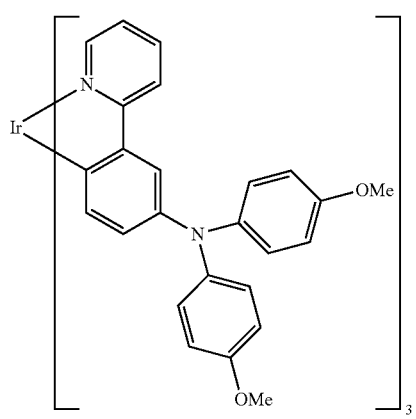
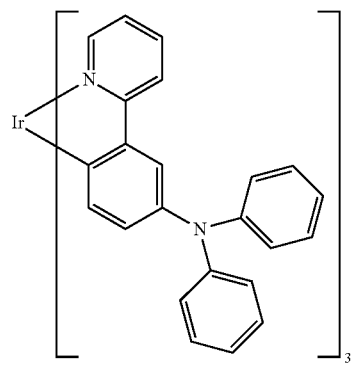
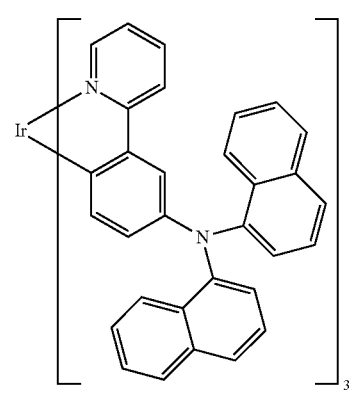
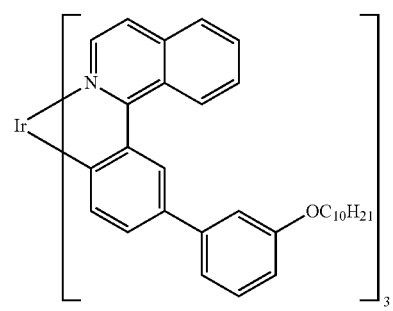
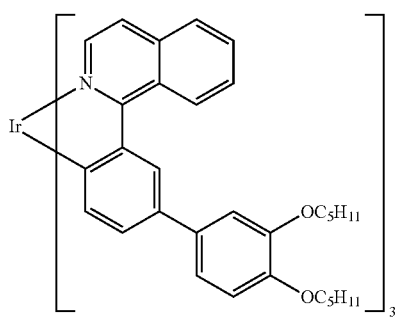

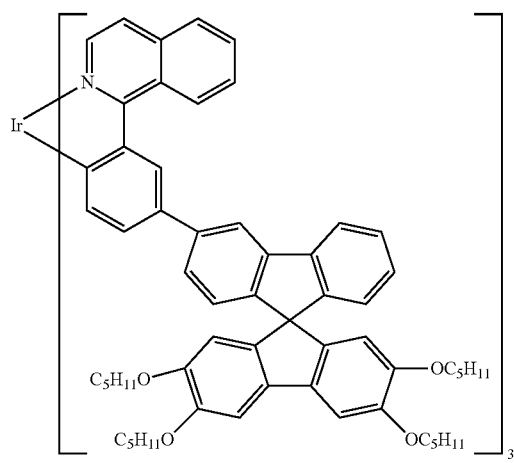
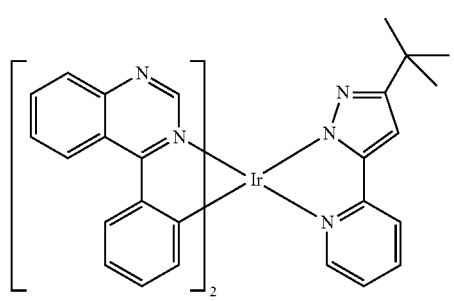
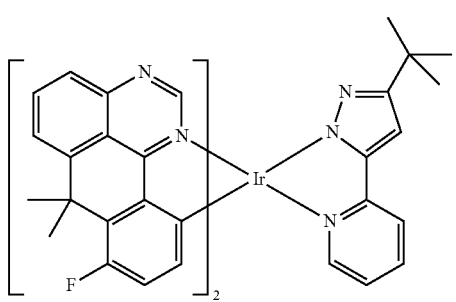
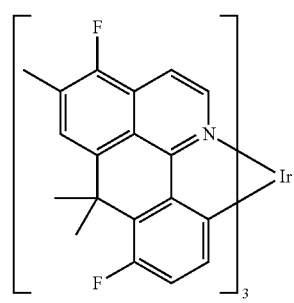
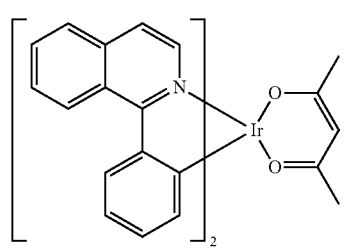
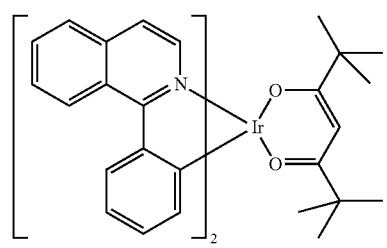
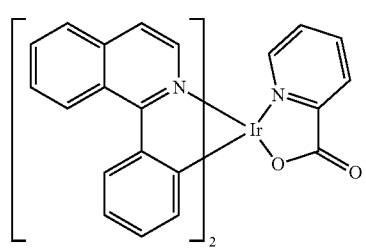
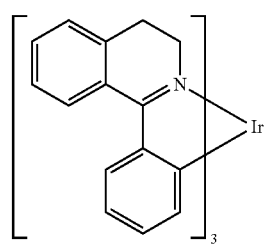
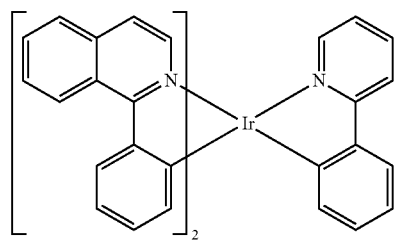
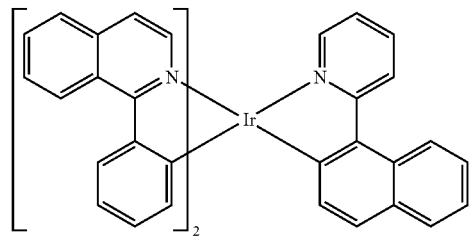
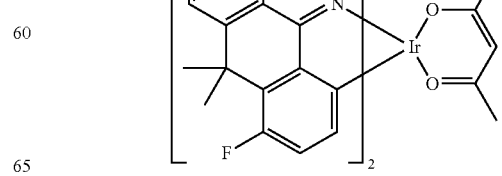

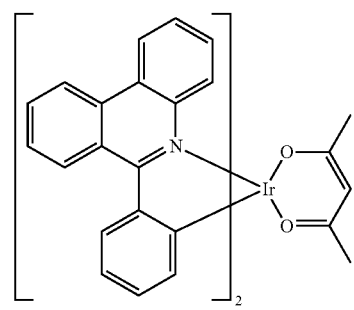
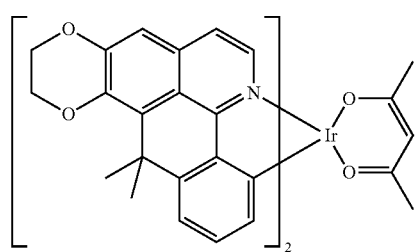
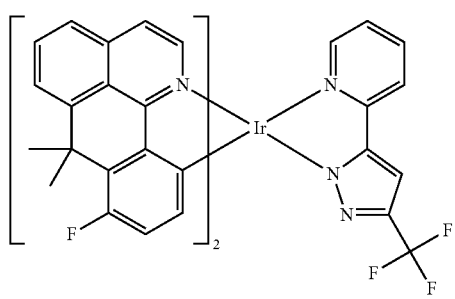
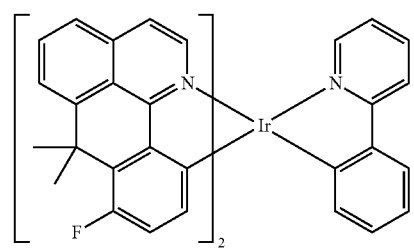
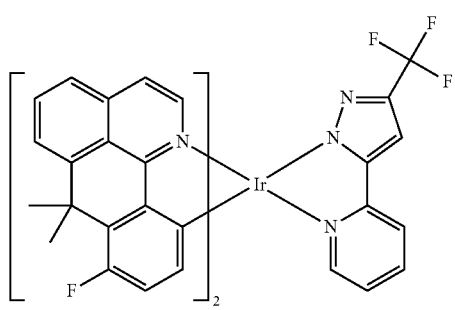
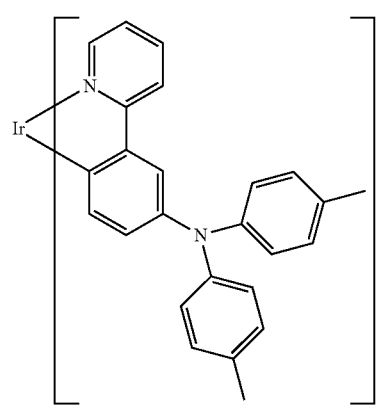
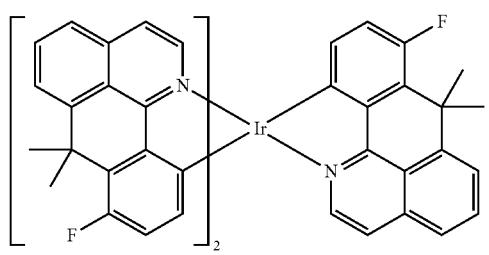
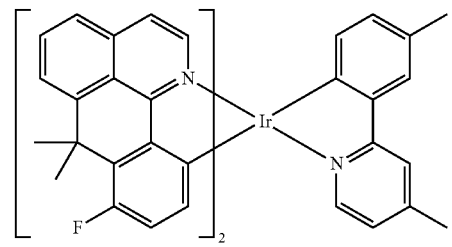
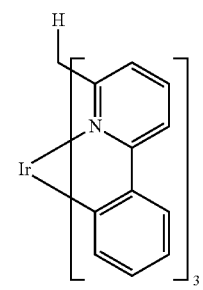
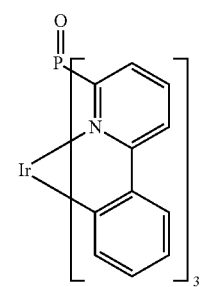

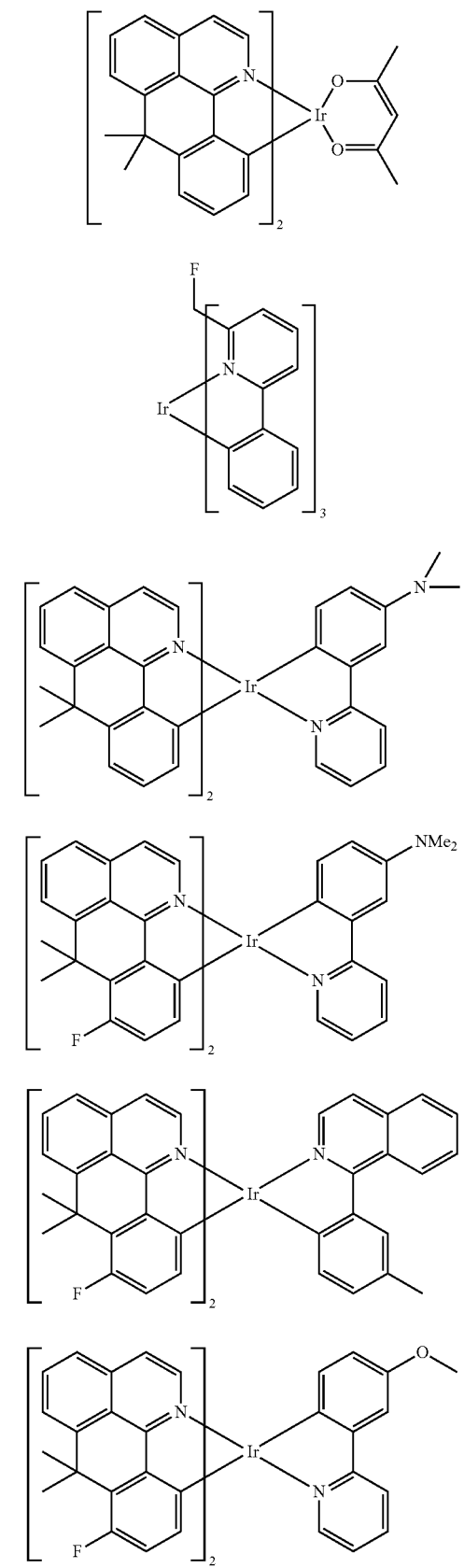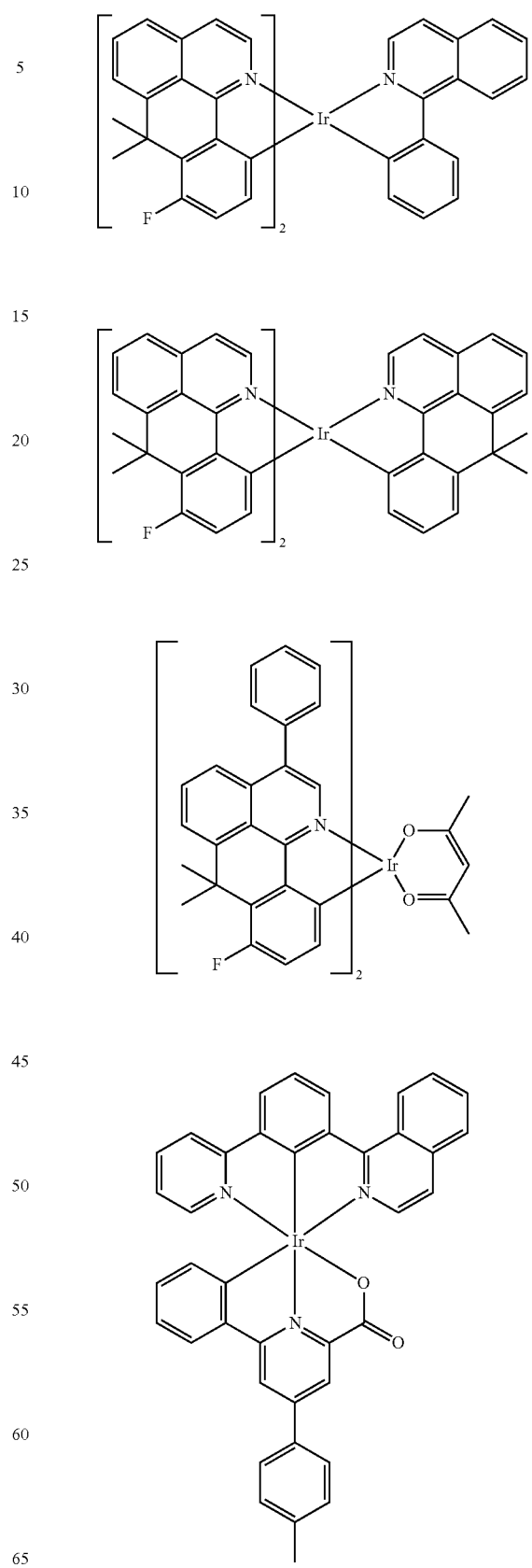

65
-continued
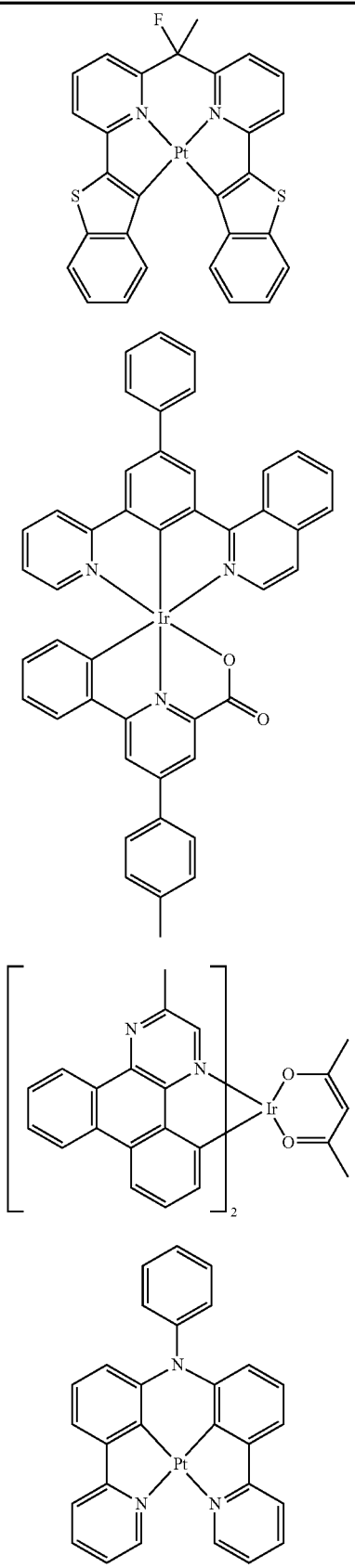
66
-continued
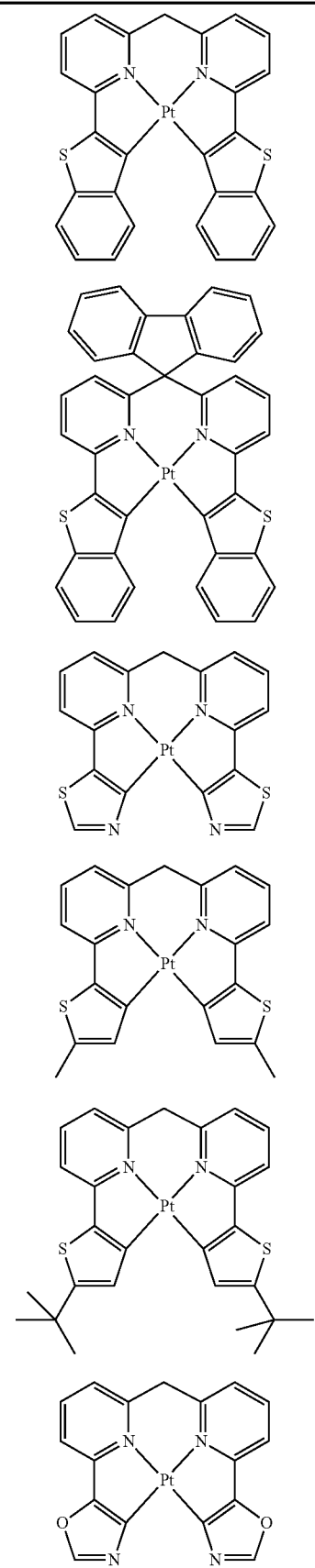

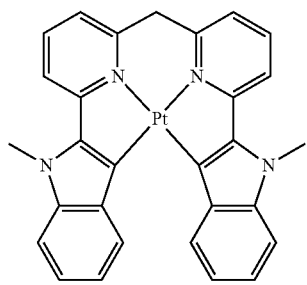
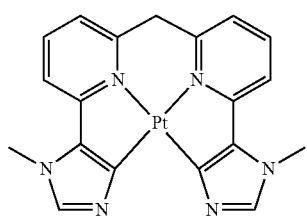
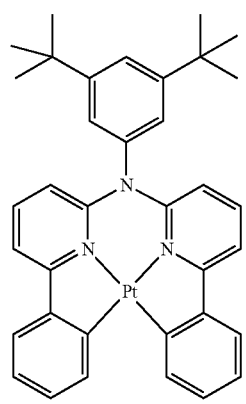
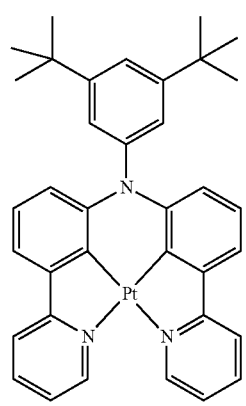
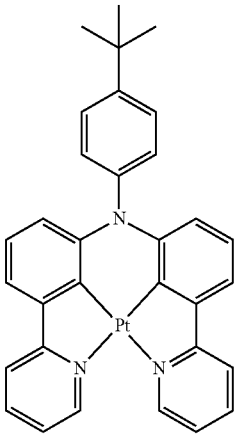
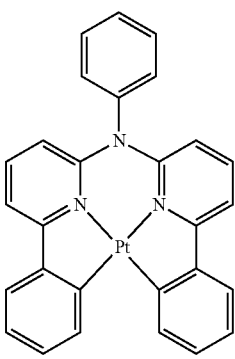
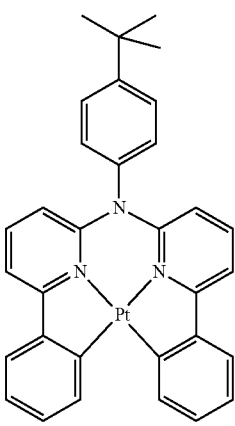
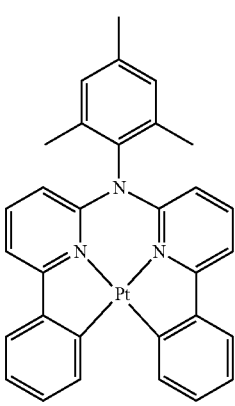

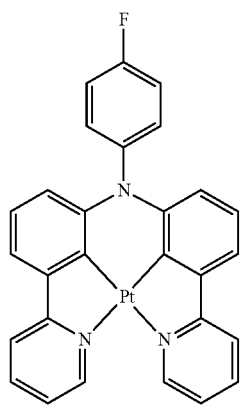
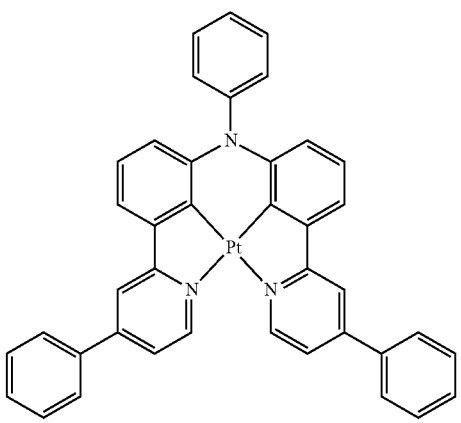
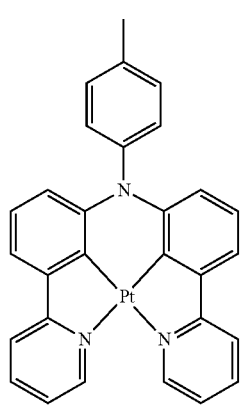
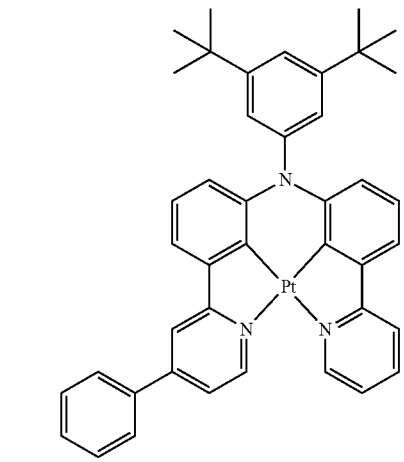
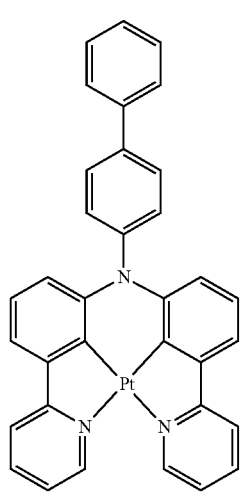
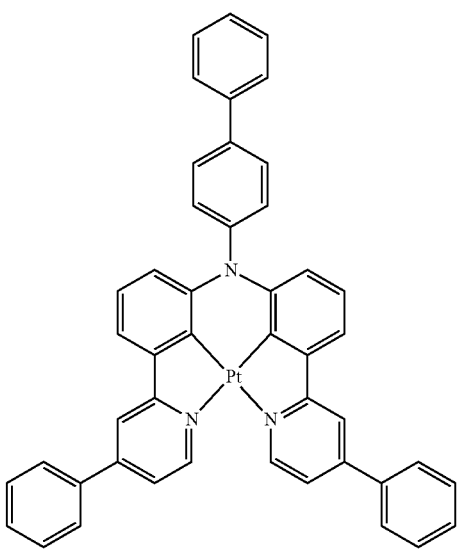

| 71 -continued | 72 -continued |
|---|---|
| 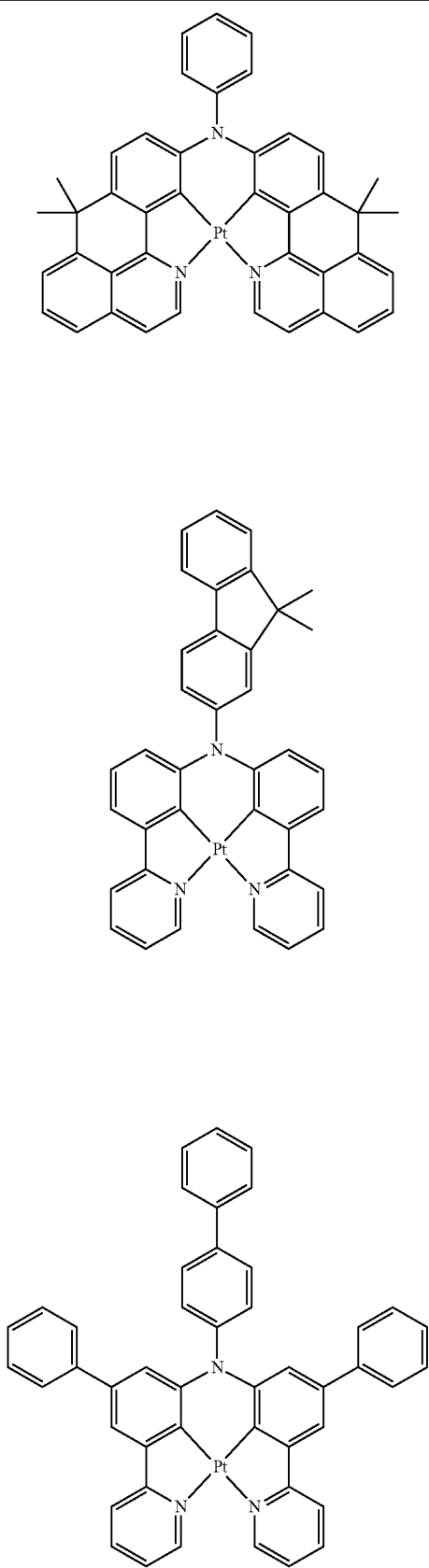 | 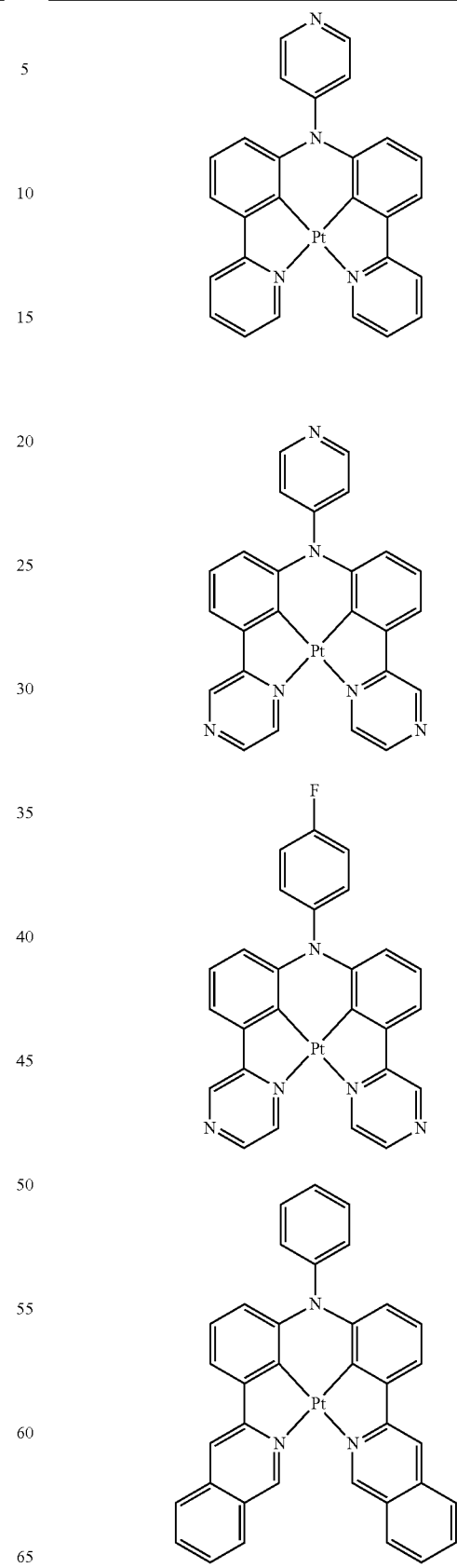 |

73
-continued
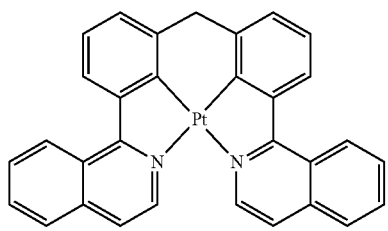
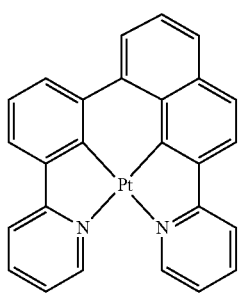
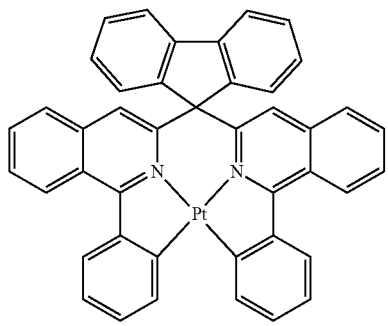
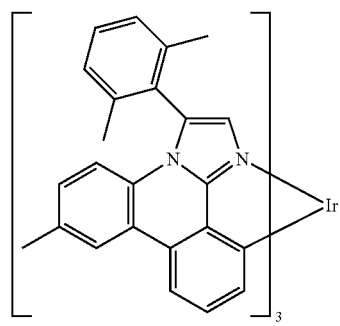
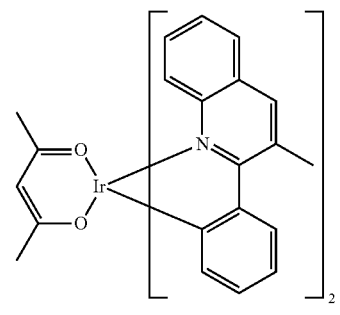
74
-continued
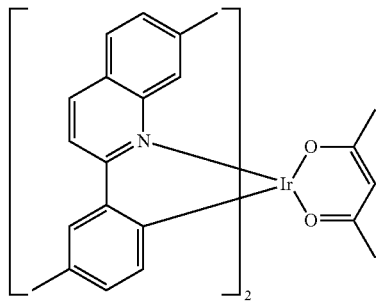
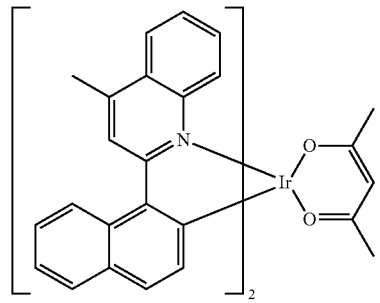
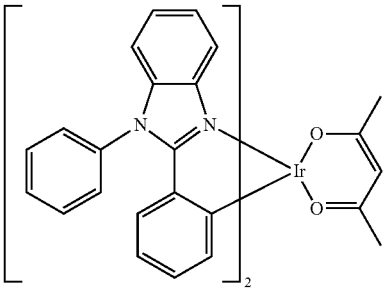
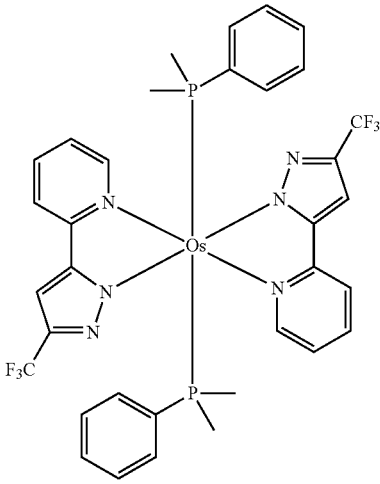
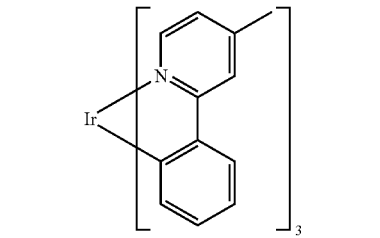

75
-continued
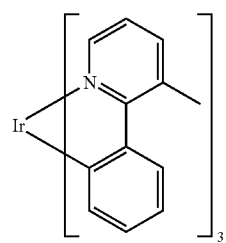
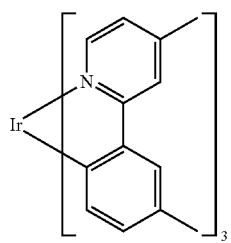
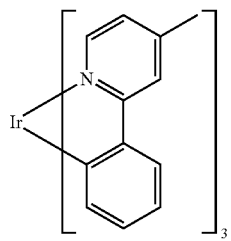
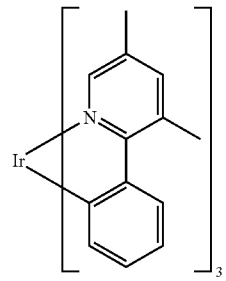
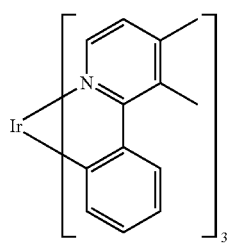
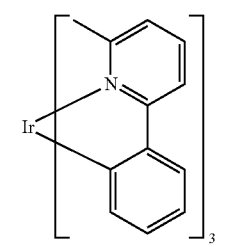
76
-continued
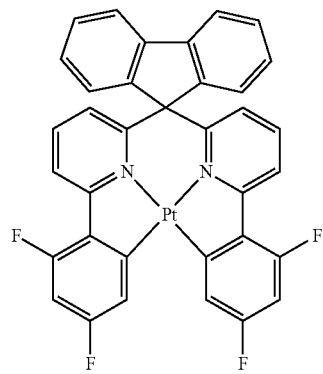
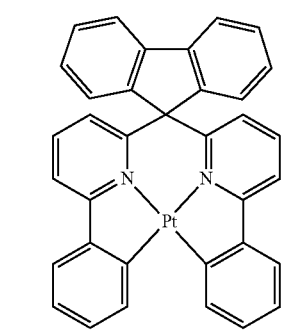
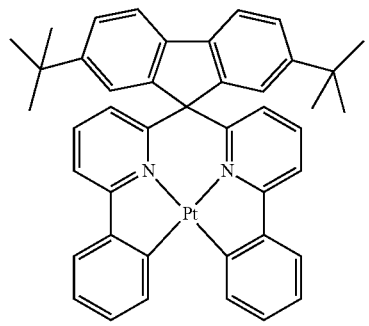
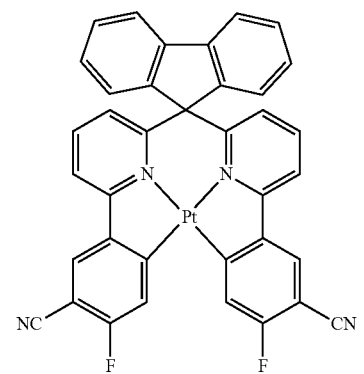

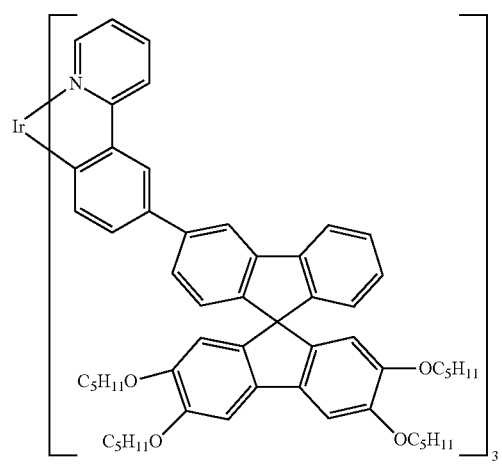
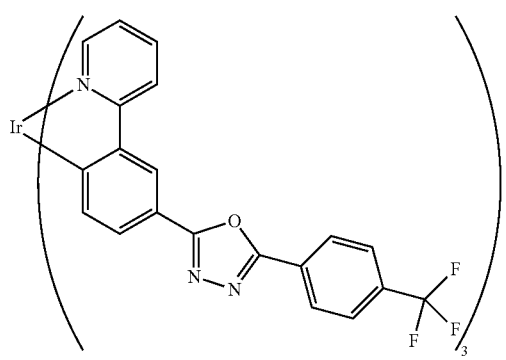
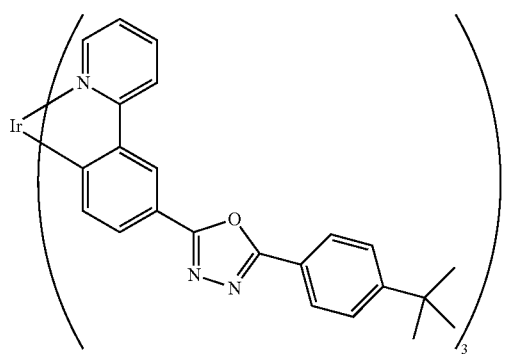
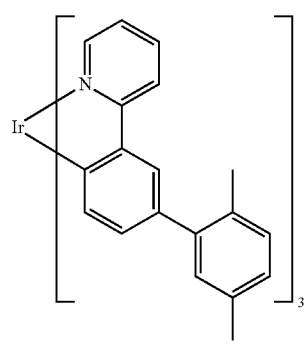
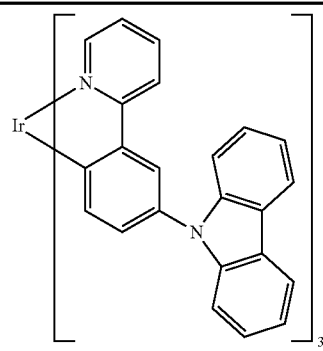
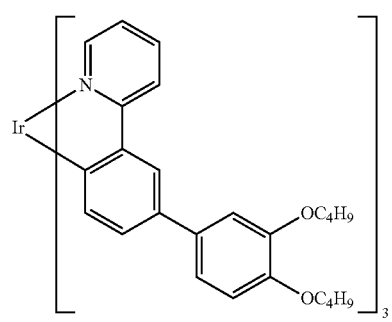
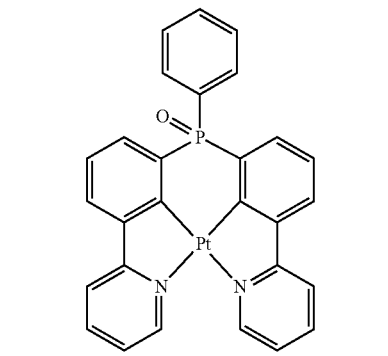
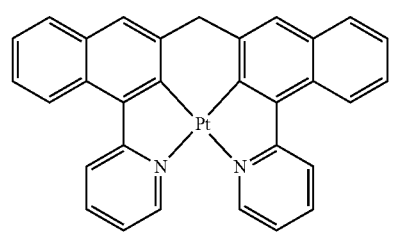
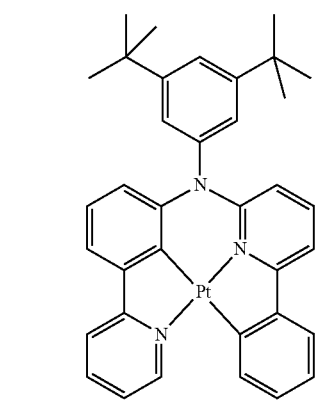

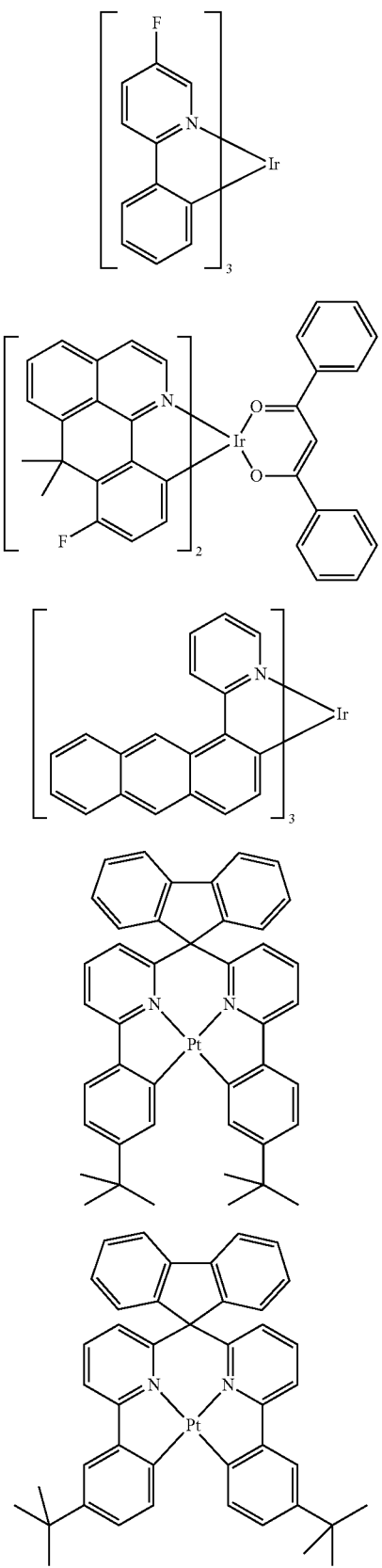
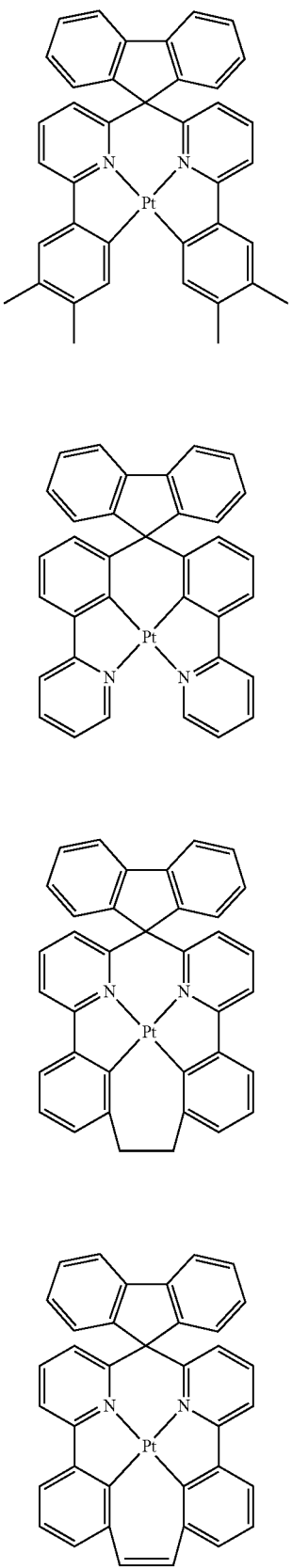

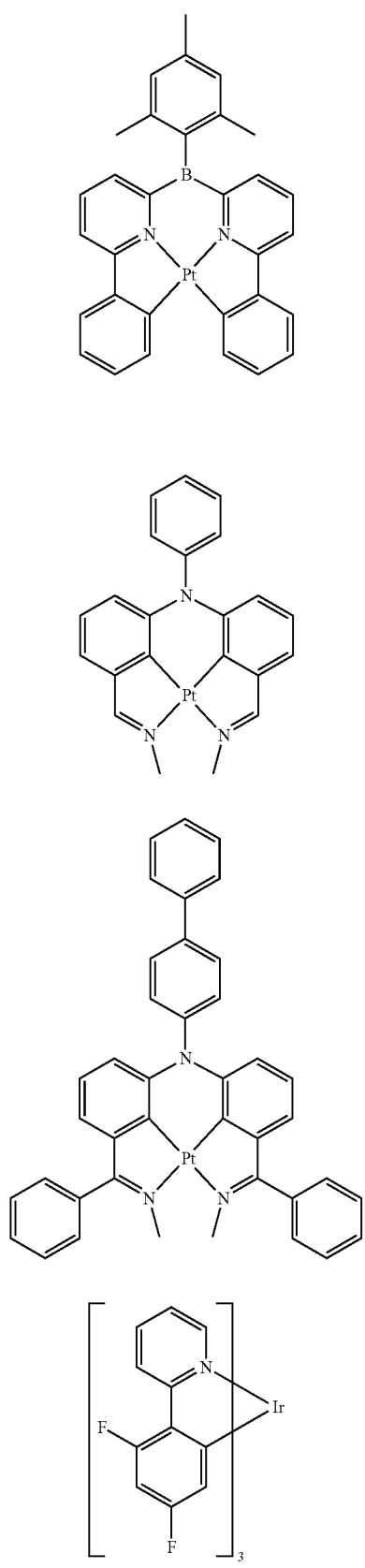
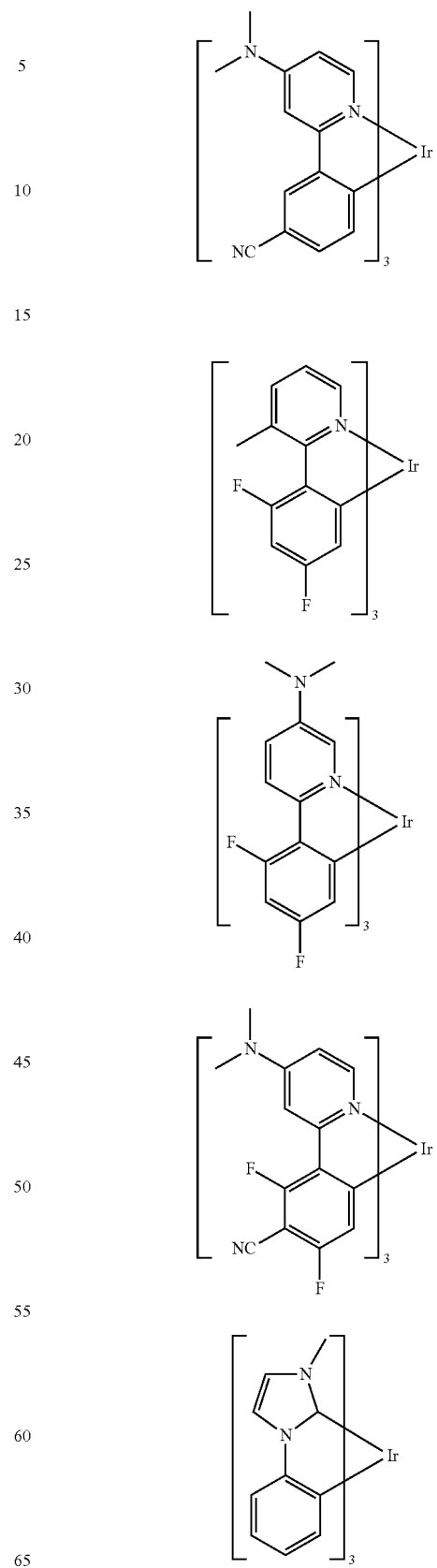

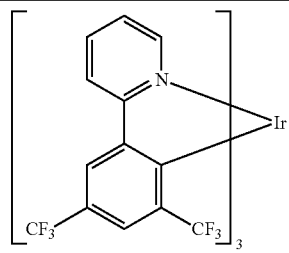
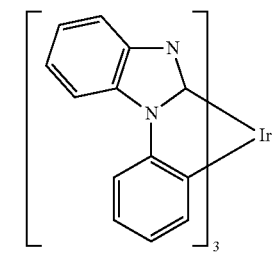
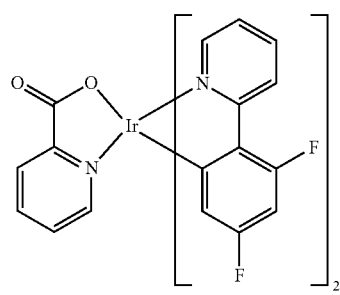
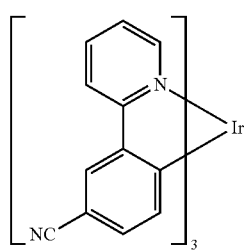
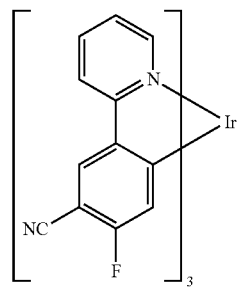
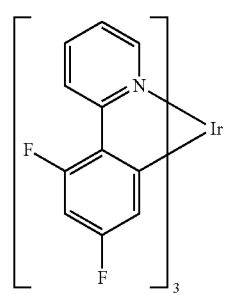
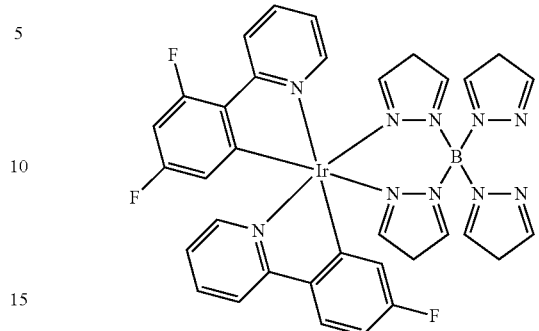
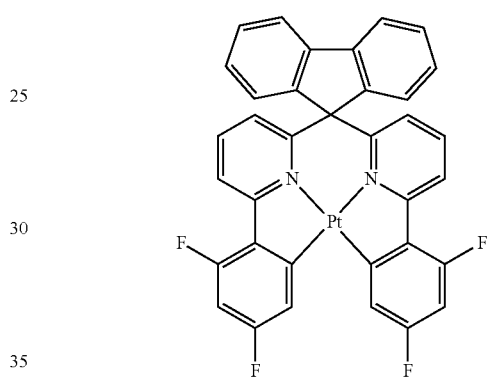
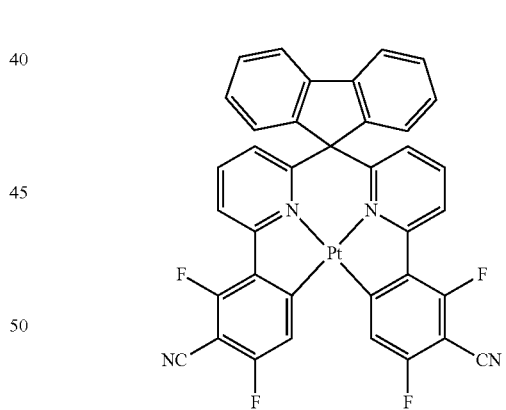
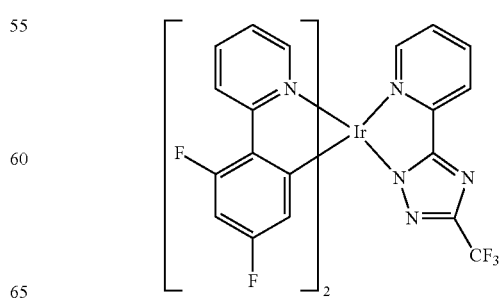

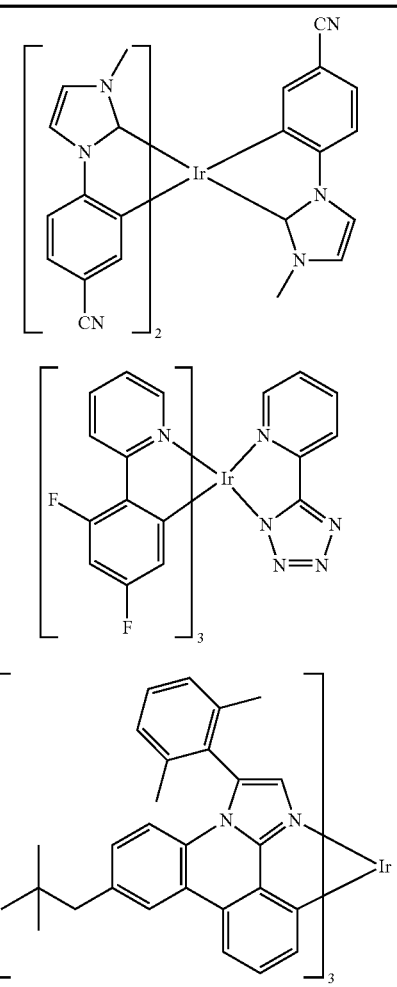

In a preferred embodiment of the present invention, the compounds of the formula (I) to (IV) are employed as matrix material in combination with one or more dopants, preferably phosphorescent dopants.

A dopant is taken to mean the component whose proportion in the mixture is the smaller in a system comprising a matrix material and a dopant. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a preferred embodiment of the invention, the compounds of the formula (I) to (IV) are used as a component of mixed-matrix systems. The mixed-matrix systems preferably comprise two or three different matrix materials, particularly preferably two different matrix materials. Preferably, one of the two materials here represents a material having hole-transporting properties and the other material represents a material having electron-transporting properties. The two different matrix materials here may be present in a ratio of 1:50 to 1:1, preferably 1:20 to 1:1, particularly preferably 1:10 to 1:1 and very particularly preferably 1:4 to 1:1.

The mixed-matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Mixed-matrix systems are preferably employed in phosphorescent organic electroluminescent devices.

Particularly suitable matrix materials, which can be employed in combination with the compounds according to the invention as matrix components of a mixed-matrix system, are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, or indenocarbazole derivatives, for example in accordance with WO 2010/136109.

Preferred phosphorescent dopants for use in mixed-matrix systems comprising the compounds according to the invention are the phosphorescent dopants mentioned in the above table.

In a further preferred embodiment of the invention, the compounds of the formula (I) to (IV) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. The hole-transport layer may be directly adjacent to the emission layer.

If the compounds of the formula (I) to (IV) are used as hole-transport material or as hole-injection material, it may be preferred for them to be doped with electron-acceptor compounds, for example with $F_4$-TCNQ or with compounds as described in EP 1476881 or EP 1596445. In a further preferred embodiment of the invention, a compound of the formula (I) to (IV) is used as hole-transport material in combination with a hexaazatriphenylene derivative as described in US 2007/0092755. The hexaazatriphenylene derivative is particularly preferably employed in its own layer here.

If the compound of the formula (I) to (IV) is employed as hole-transport material in a hole-transport layer, the compound can be employed as pure material, i.e. in a proportion of 100%, in the hole-transport layer or it can be employed in combination with one or more further compounds in the hole-transport layer.

In a further embodiment of the invention, the compounds of the formula (I) to (IV) are employed as fluorescent dopants in an electroluminescent layer. In this case, the compounds are preferably used as green or blue emitters.

Preferred matrix materials for use in combination with the compounds of the formula (I) to (IV) as fluorescent dopants are mentioned in one of the following sections.

The materials preferably employed for the respective functions in the electronic devices according to the invention are mentioned below.

Preferred fluorescent emitter materials are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding styrylphosphines and styryl ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitter materials are selected from indenofluorenamines or indenofluorenediamines, for example in accordance with WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847. Examples of emitter materials from the class of the styrylamines are substituted or unsubstituted tristilbenamines or the emitter materials described in WO 2006/000388, WO 2006/058737, WO 2006/000389, WO 2007/065549 and WO 2007/115610. Preference is furthermore given to the condensed hydrocarbons disclosed in WO 2010/012328.

Furthermore, the compounds of the formula (I) to (IV) are preferably used as fluorescent emitter materials.

Suitable emitter materials are furthermore the structures depicted in the following table, and the derivatives of these structures disclosed in JP 2006/001973, WO 2004/047499, WO 2006/098080, WO 2007/065678, US 2005/0260442 and WO 2004/092111.

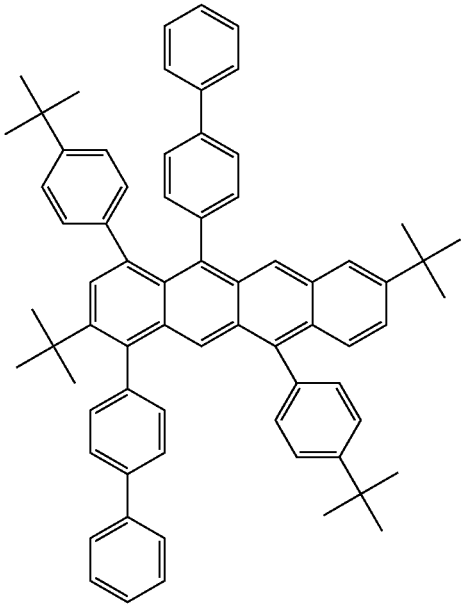 [SMILES: CC(C)(C)c1ccc(-c2c3ccc(C(C)(C)C)cc3cc3c(-c4ccc(-c5ccccc5)cc4)c4c(-c5ccc(C(C)(C)C)cc5)cc(C(C)(C)C)c(-c5ccc(-c6ccccc6)cc5)c4cc23)cc1]

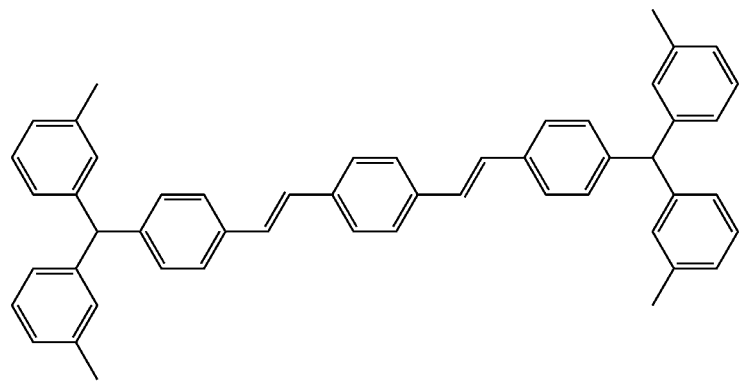 [SMILES: Cc1cccc(C(c2ccc(/C=C/c3ccc(/C=C/c4ccc(C(c5cccc(C)c5)c5cccc(C)c5)cc4)cc3)cc2)c2cccc(C)c2)c1]
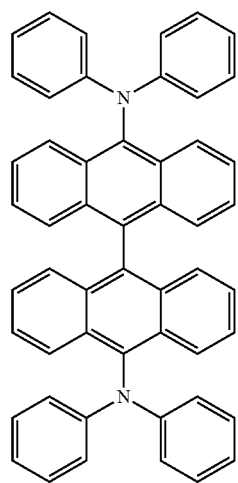 [SMILES: c1ccc(N(c2ccccc2)c2c3ccccc3c(-c3c4ccccc4c(N(c4ccccc4)c4ccccc4)c4ccccc34)c3ccccc23)cc1]
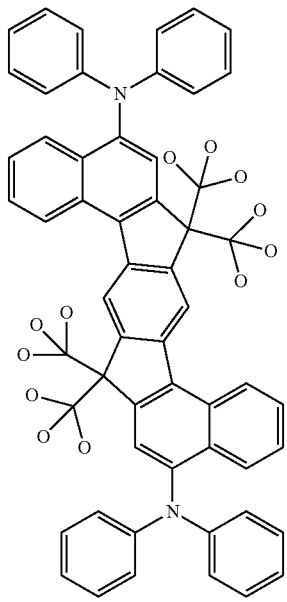 [SMILES: OC(O)(O)C1(C(O)(O)O)c2cc3c(cc2-c2c1cc(N(c1ccccc1)c1ccccc1)c1ccccc21)C(C(O)(O)O)(C(O)(O)O)c1cc(N(c2ccccc2)c2ccccc2)c2ccccc2c1-3]

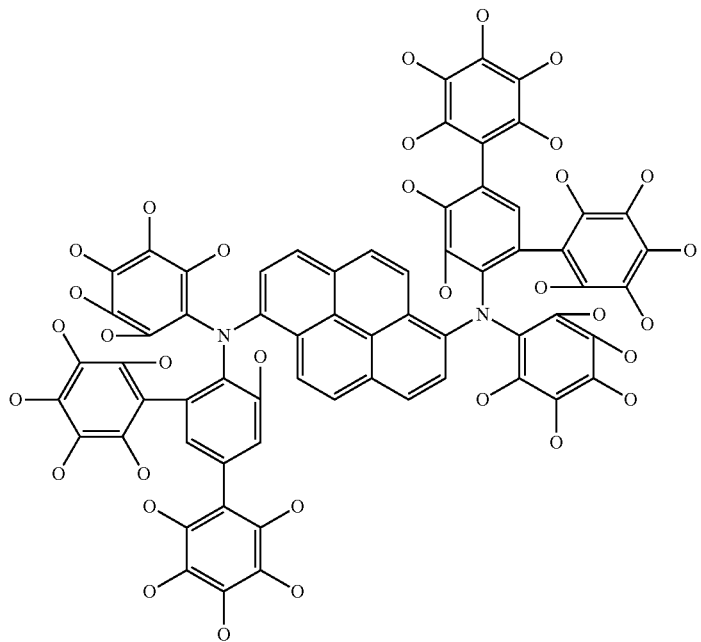 [SMILES: Oc1cc(-c2c(O)c(O)c(O)c(O)c2O)cc(-c2c(O)c(O)c(O)c(O)c2O)c1N(c1c(O)c(O)c(O)c(O)c1O)c1ccc2ccc3c(N(c4c(-c5c(O)c(O)c(O)c(O)c5O)cc(-c5c(O)c(O)c(O)c(O)c5O)c(O)c4O)c4c(O)c(O)c(O)c(O)c4O)ccc4ccc1c2c43]
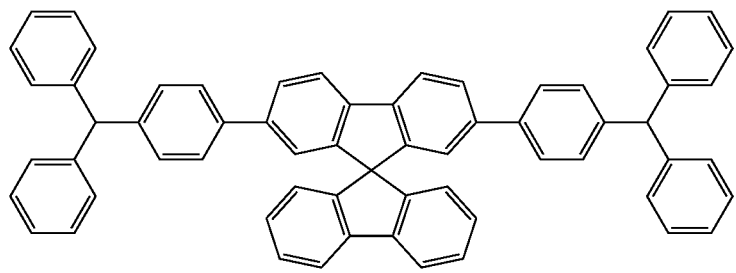 [SMILES: c1ccc(C(c2ccccc2)c2ccc(-c3ccc4c(c3)C3(c5ccccc5-c5ccccc53)c3cc(-c5ccc(C(c6ccccc6)c6ccccc6)cc5)ccc3-4)cc2)cc1]
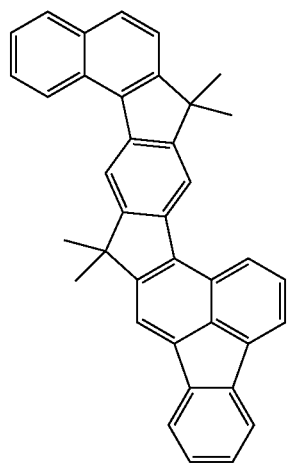 [SMILES: CC1(C)c2cc3c(cc2-c2c1ccc1ccccc21)C(C)(C)c1cc2c4c(cccc4c1-3)-c1ccccc1-2]

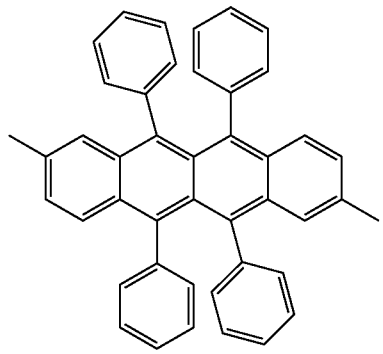
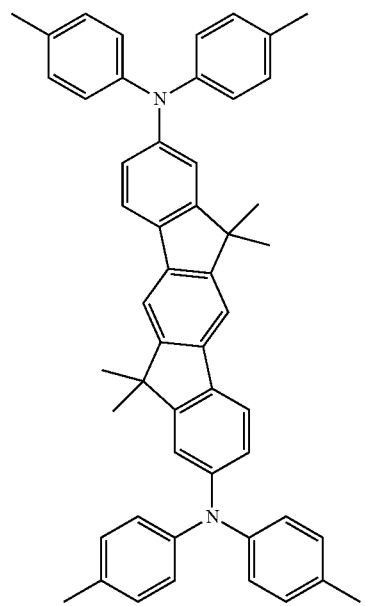
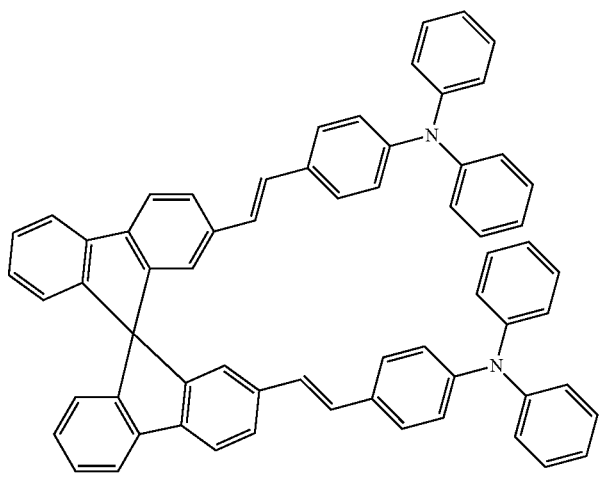 [SMILES: C(=C\c1ccc2c(c1)C1(c3ccccc3-2)c2ccccc2-c2ccc(/C=C/c3ccc(N(c4ccccc4)c4ccccc4)cc3)cc21)/c1ccc(N(c2ccccc2)c2ccccc2)cc1]

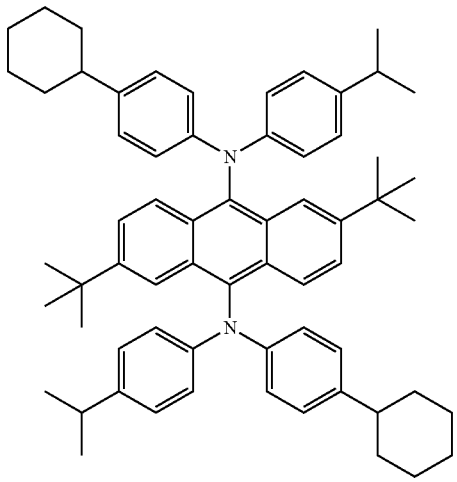 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
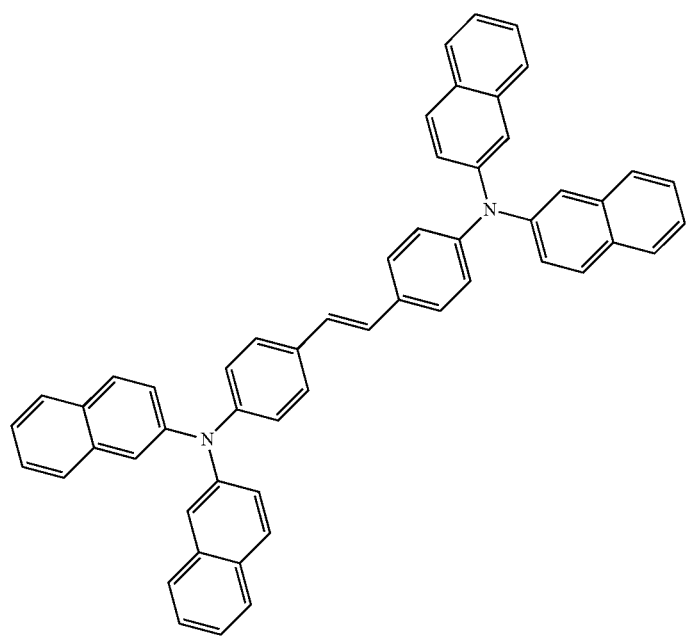 [SMILES: C(=C\c1ccc(N(c2ccc3ccccc3c2)c2ccc3ccccc3c2)cc1)/c1ccc(N(c2ccc3ccccc3c2)c2ccc3ccccc3c2)cc1]

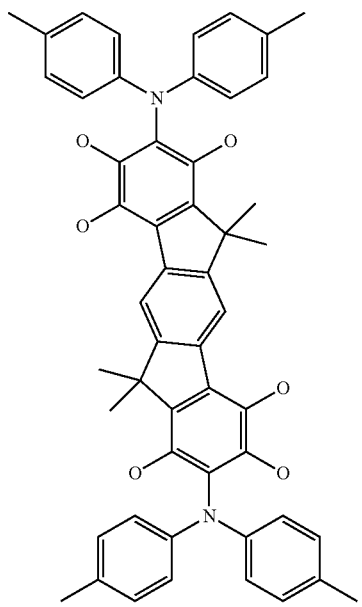
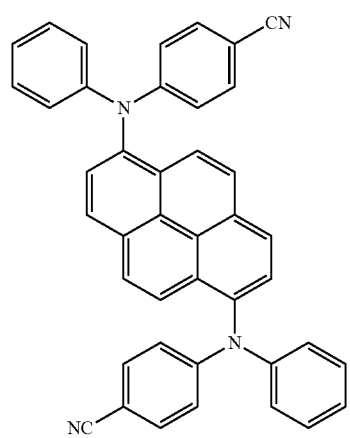 [SMILES: N#Cc1ccc(N(c2ccccc2)c2ccc3ccc4c(N(c5ccccc5)c5ccc(C#N)cc5)ccc5ccc2c3c54)cc1]

-continued
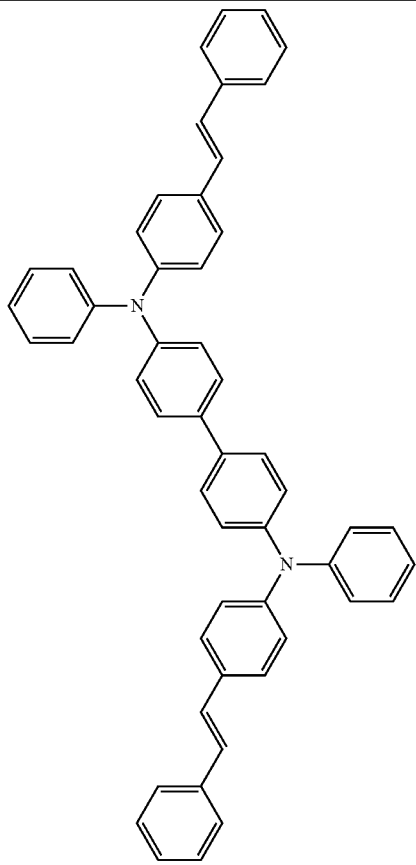
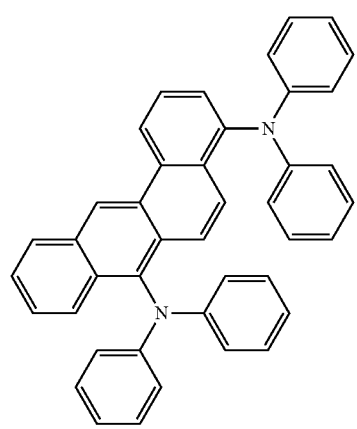 [SMILES: c1ccc(N(c2ccccc2)c2cccc3c2ccc2c(N(c4ccccc4)c4ccccc4)c4ccccc4cc23)cc1]

-continued
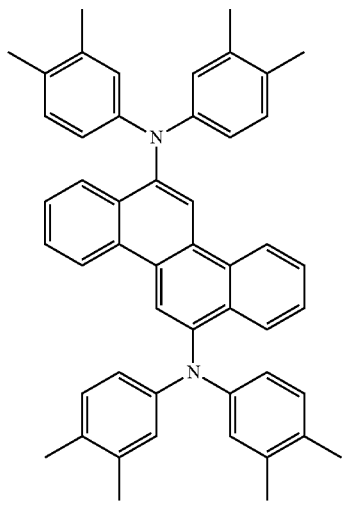
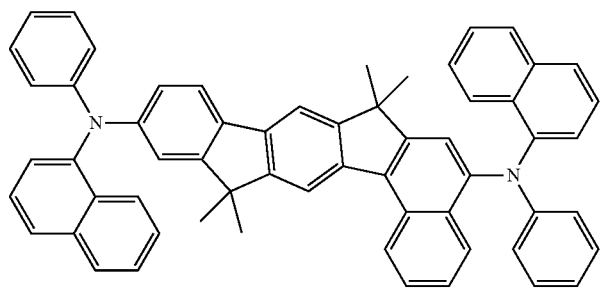 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
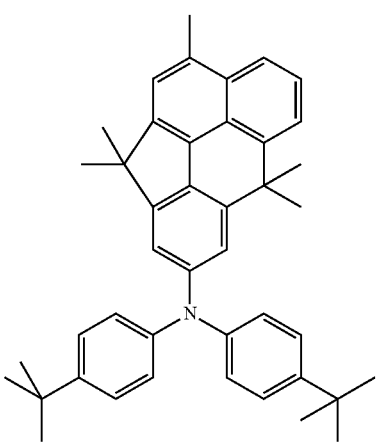 [SMILES: Cc1cc2c3c4c(cccc14)C(C)(C)c1cc(N(c4ccc(C(C)(C)C)cc4)c4ccc(C(C)(C)C)cc4)cc(c1-3)C2(C)C]
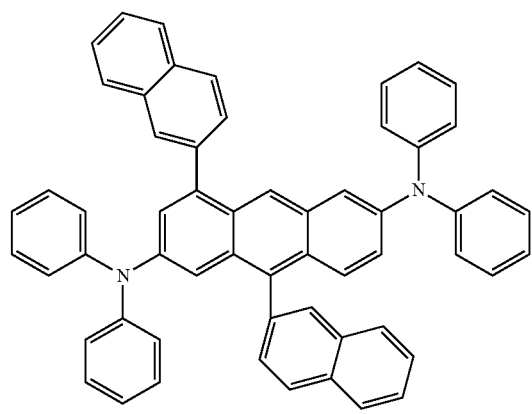 [SMILES: c1ccc(N(c2ccccc2)c2ccc3c(-c4ccc5ccccc5c4)c4cc(N(c5ccccc5)c5ccccc5)cc(-c5ccc6ccccc6c5)c4cc3c2)cc1]

-continued
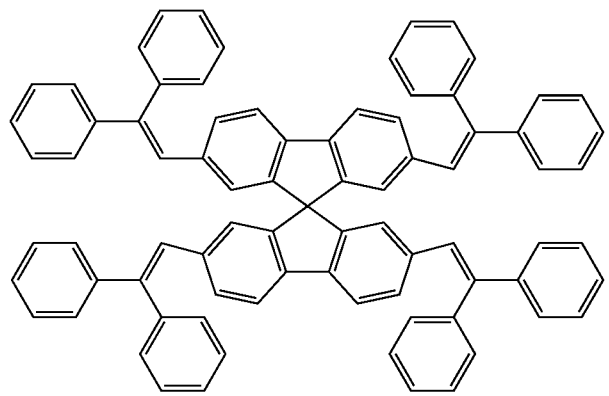 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]
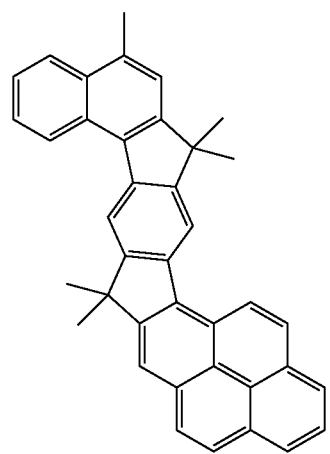 [SMILES: Cc1cc2c(c3ccccc13)-c1cc3c(cc1C2(C)C)-c1c(cc2ccc4cccc5ccc1c2c45)C3(C)C]
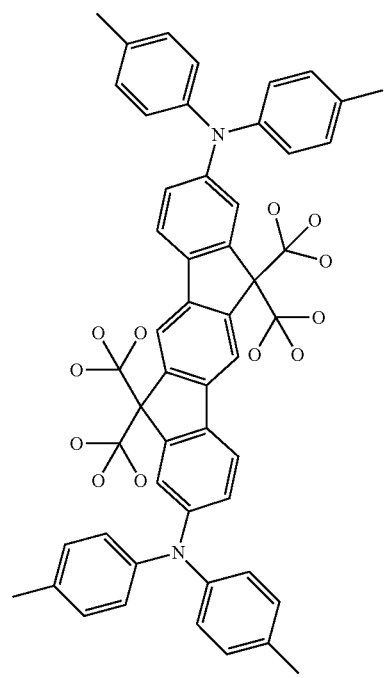

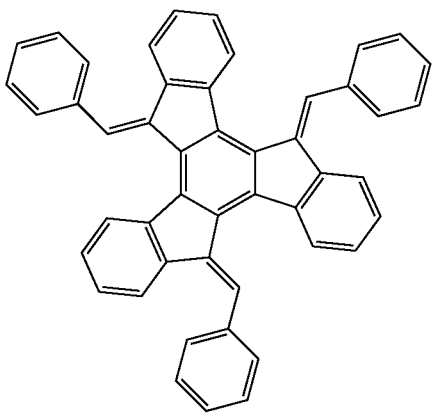 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]
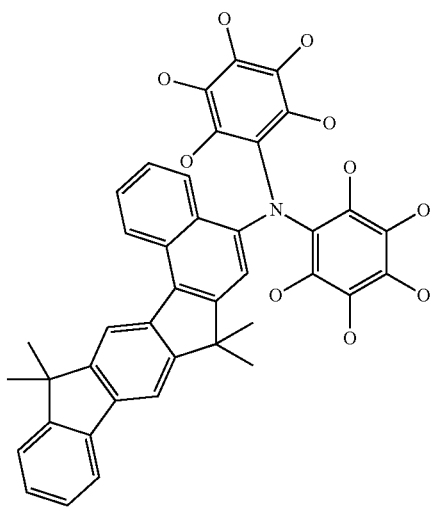 [SMILES: CC1(C)c2ccccc2-c2cc3c(cc21)-c1c(cc(N(c2c(O)c(O)c(O)c(O)c2O)c2c(O)c(O)c(O)c(O)c2O)c2ccccc12)C3(C)C]
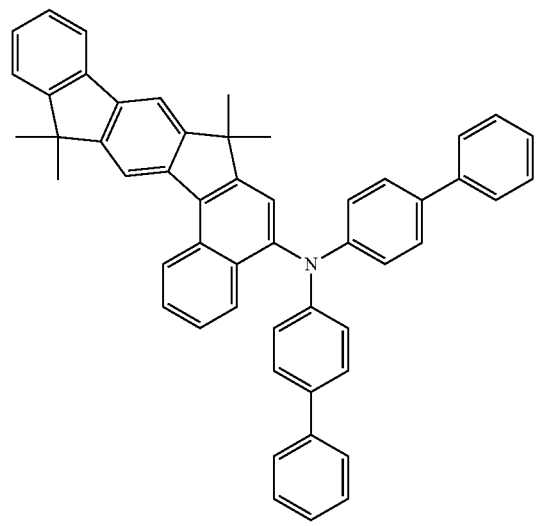 [SMILES: CC1(C)c2ccccc2-c2cc3c(cc21)-c1c(cc(N(c2ccc(-c4ccccc4)cc2)c2ccc(-c4ccccc4)cc2)c2ccccc12)C3(C)C]

-continued
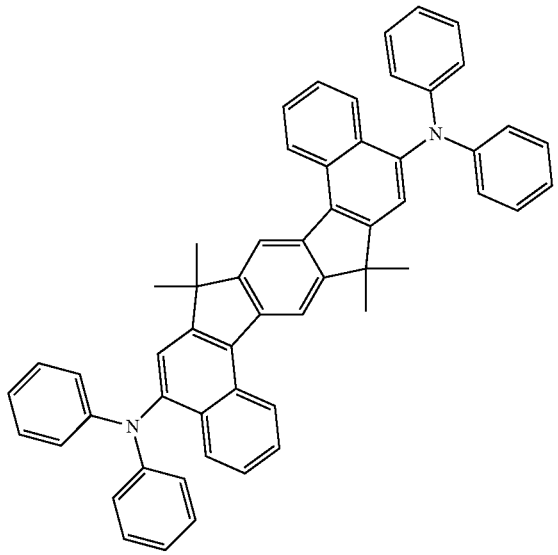 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]
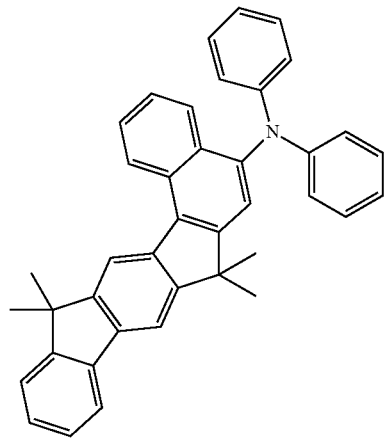 [SMILES: CC1(C)c2ccccc2-c2cc3c(cc21)-c1c(cc(N(c2ccccc2)c2ccccc2)c2ccccc12)C3(C)C]
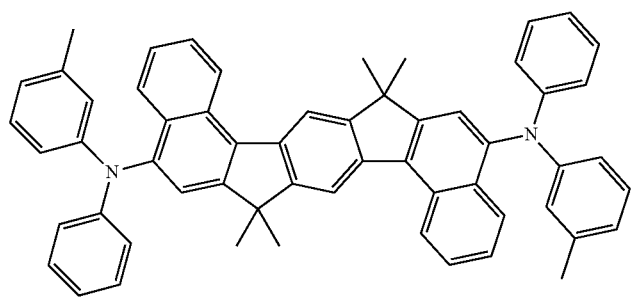 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]

-continued
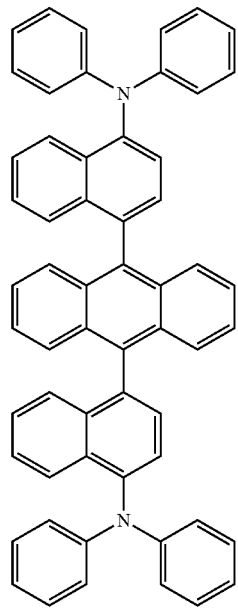 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]
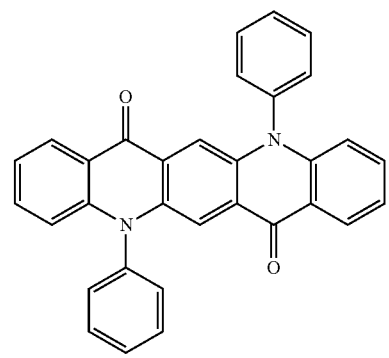 [SMILES: O=c1c2ccccc2n(-c2ccccc2)c2cc3c(=O)c4ccccc4n(-c4ccccc4)c3cc12]
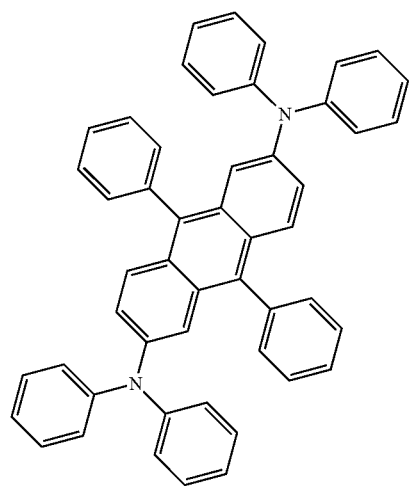 [SMILES: c1ccc(-c2c3ccc(N(c4ccccc4)c4ccccc4)cc3c(-c3ccccc3)c3ccc(N(c4ccccc4)c4ccccc4)cc23)cc1]

-continued
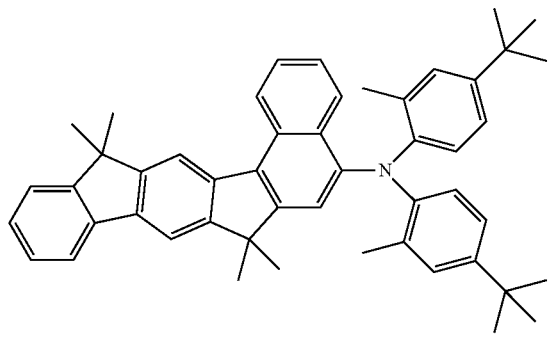 [SMILES: Cc1cc(C(C)(C)C)ccc1N(c1ccc(C(C)(C)C)cc1C)c1cc2c(c3ccccc13)-c1cc3c(cc1C2(C)C)-c1ccccc1C3(C)C]
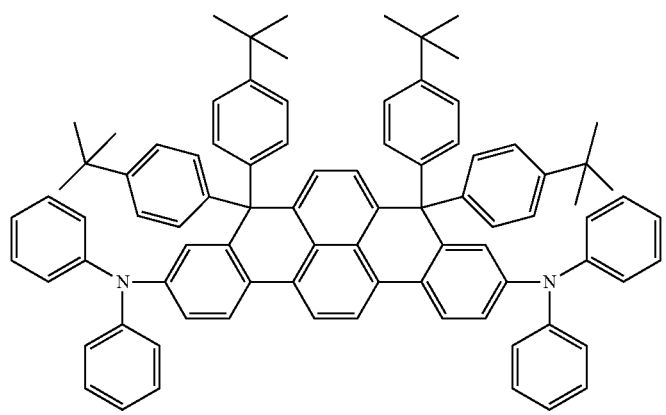 [SMILES: CC(C)(C)c1ccc(C2(c3ccc(C(C)(C)C)cc3)c3cc(N(c4ccccc4)c4ccccc4)ccc3-c3ccc4c5c(ccc2c35)C(c2ccc(C(C)(C)C)cc2)(c2ccc(C(C)(C)C)cc2)c2cc(N(c3ccccc3)c3ccccc3)ccc2-4)cc1]
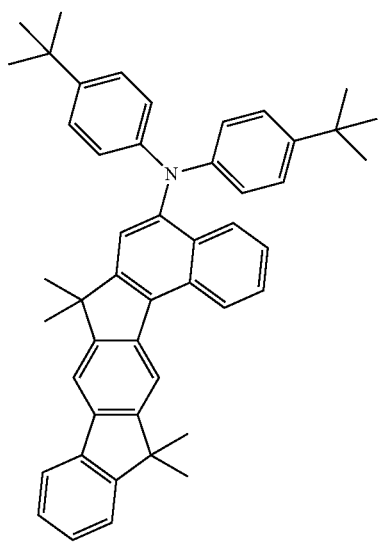 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]

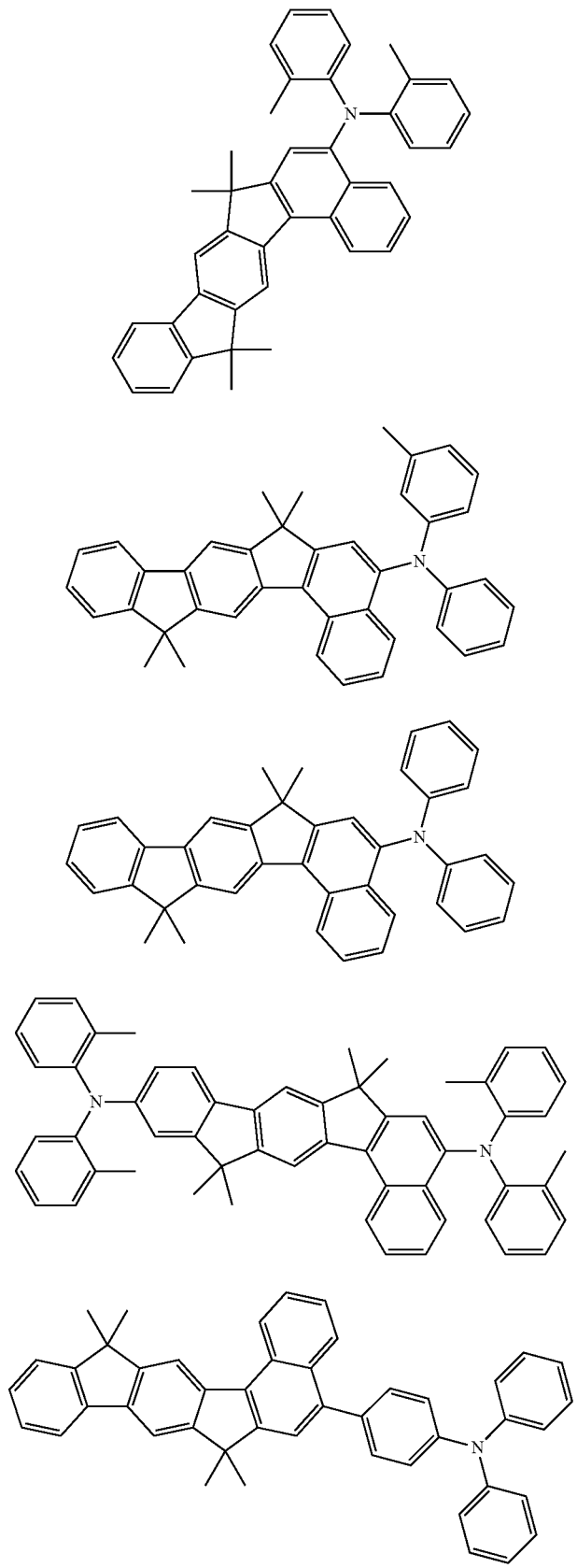

-continued
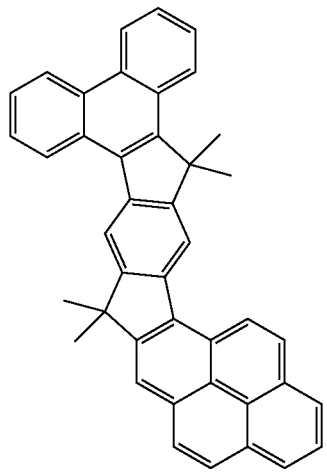 [SMILES: CC1(C)c2cc3c(cc2-c2c1cc1ccc4cccc5ccc2c1c45)C(C)(C)c1c-3c2ccccc2c2ccccc12]
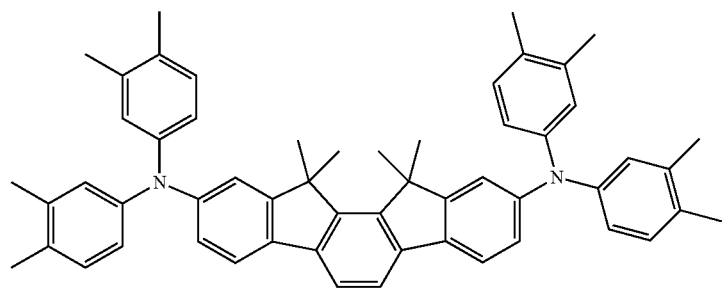
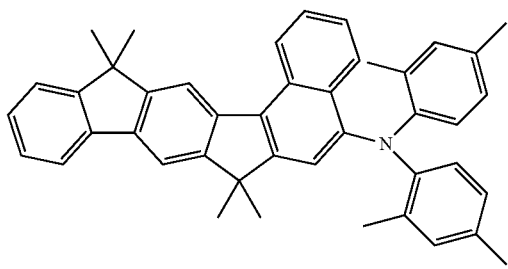 [SMILES: Cc1ccc(N(c2ccc(C)cc2C)c2cc3c(c4ccccc24)-c2cc4c(cc2C3(C)C)-c2ccccc2C4(C)C)c(C)c1]
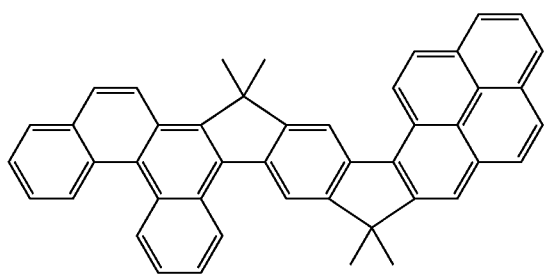 [SMILES: CC1(C)c2cc3c(cc2-c2c1cc1ccc4cccc5ccc2c1c45)C(C)(C)c1c-3c2ccccc2c2c1ccc1ccccc12]

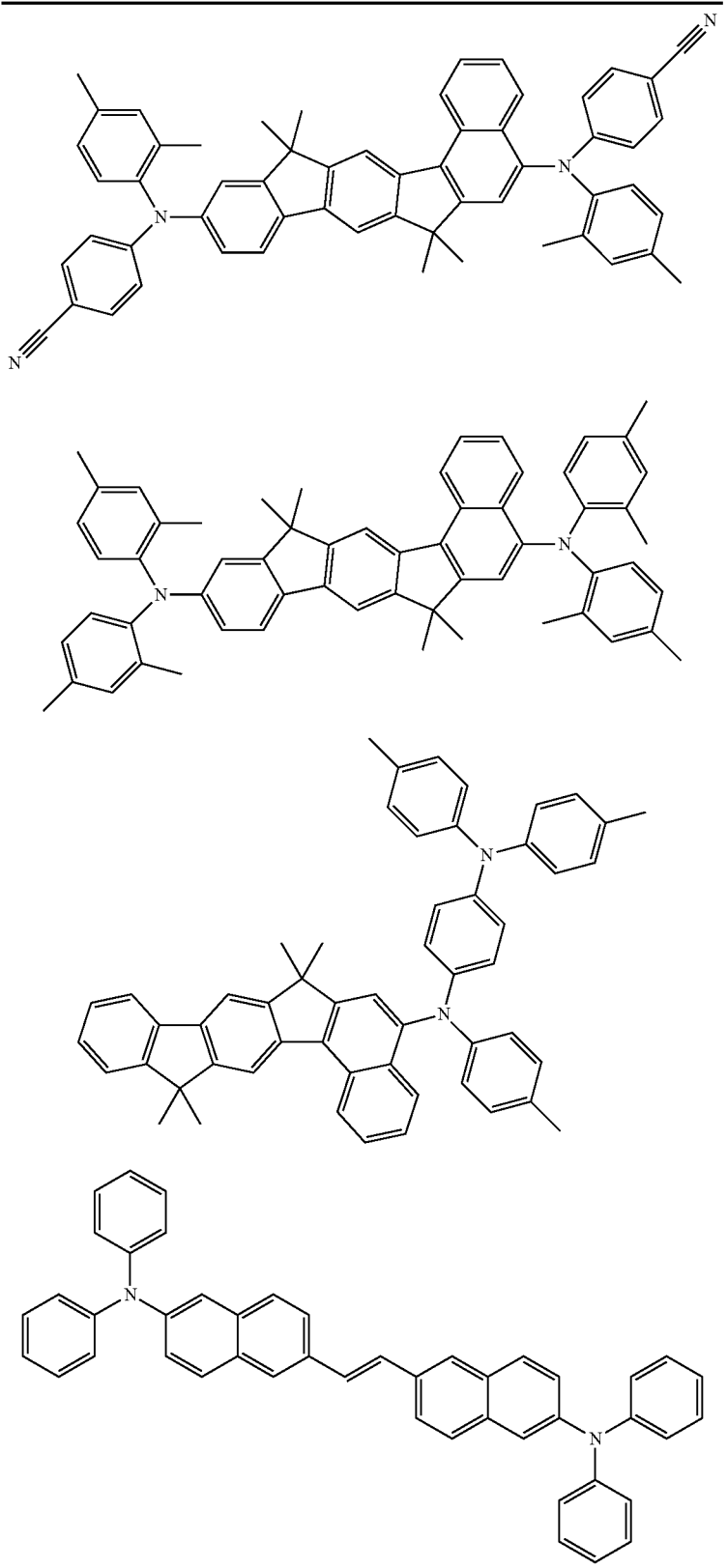
Suitable matrix materials, preferably for fluorescent dopants, are materials from various classes of substance. Preferred matrix materials are selected from the classes of the oligoarylenes (for example 2,2',7,7'-tetraphenyl-spirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Suitable matrix materials are furthermore preferably the compounds according to the invention. Apart from the compounds according to the invention, particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials, apart from the compounds according to the invention, are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials, preferably for fluorescent dopants, are, for example, the materials depicted in the following table, and derivatives of these materials, as disclosed in WO 2004/018587, WO 2008/006449, U.S. Pat. No. 5,935, 721, US 2005/0181232, JP 2000/273056, EP 681019, US 2004/0247937 and US 2005/0211958.

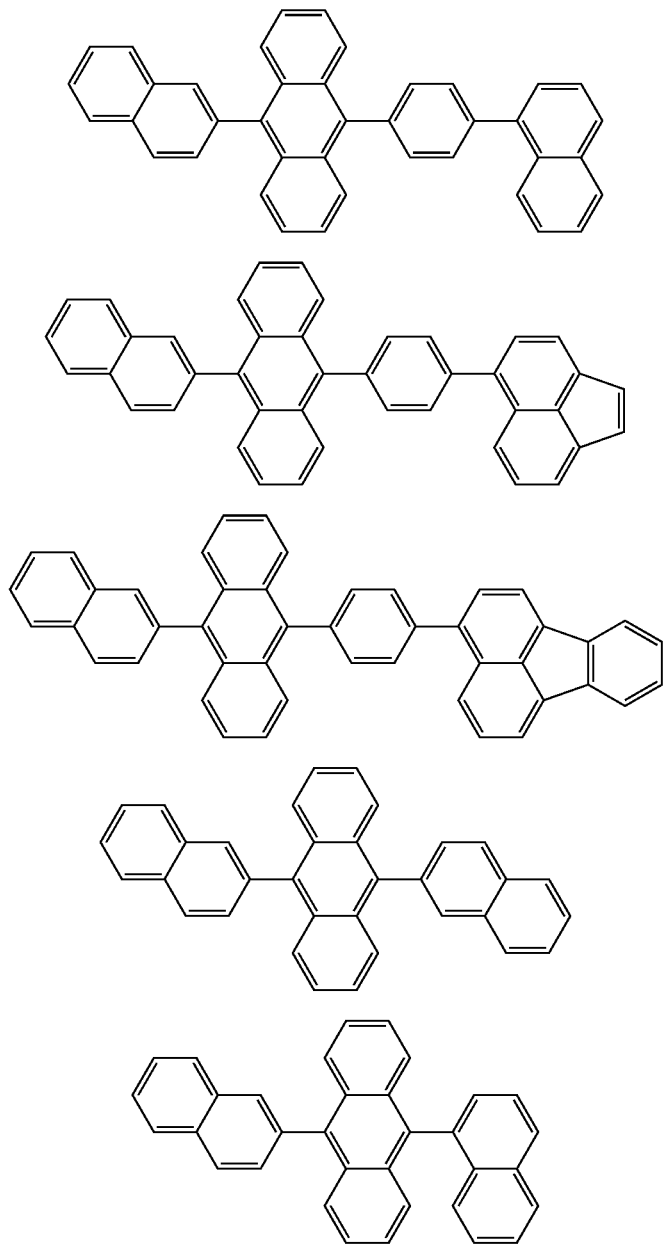

-continued
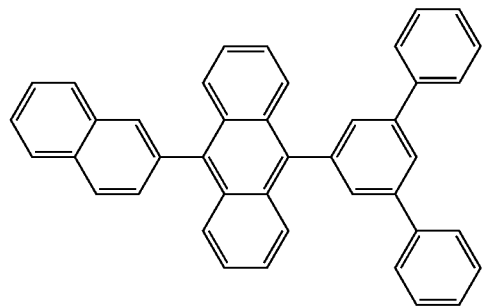 [SMILES: c1ccc(-c2cc(-c3ccccc3)cc(-c3c4ccccc4c(-c4ccc5ccccc5c4)c4ccccc34)c2)cc1]
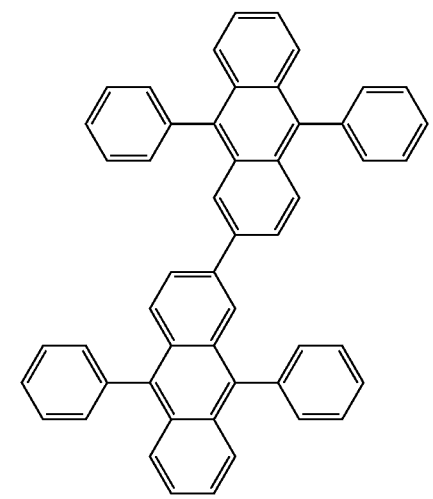 [SMILES: c1ccc(-c2c3ccccc3c(-c3ccccc3)c3cc(-c4ccc5c(-c6ccccc6)c6ccccc6c(-c6ccccc6)c5c4)ccc23)cc1]
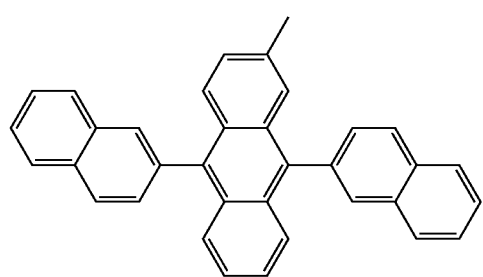 [SMILES: Cc1ccc2c(-c3ccc4ccccc4c3)c3ccccc3c(-c3ccc4ccccc4c3)c2c1]
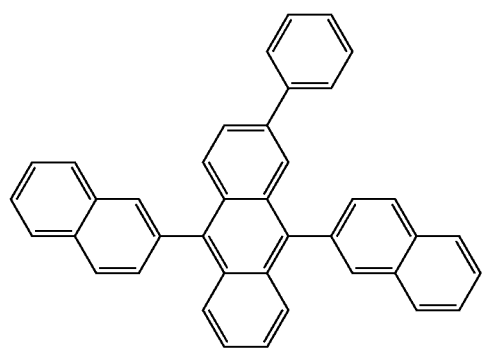 [SMILES: c1ccc(-c2ccc3c(-c4ccc5ccccc5c4)c4ccccc4c(-c4ccc5ccccc5c4)c3c2)cc1]

-continued
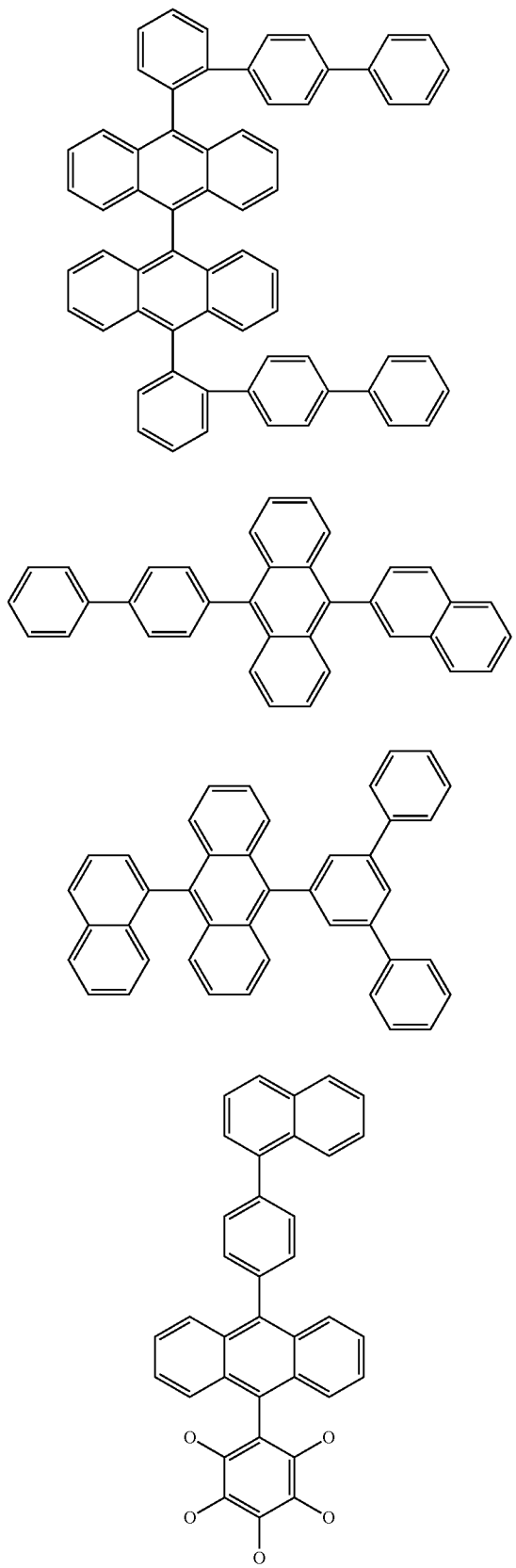

-continued
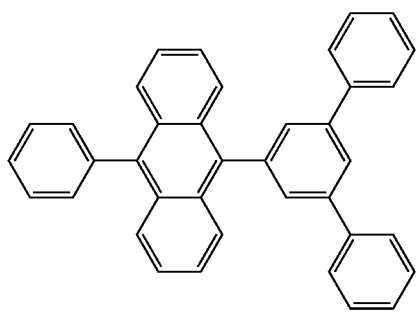 [SMILES: c1ccc(-c2cc(-c3ccccc3)cc(-c3c4ccccc4c(-c4ccccc4)c4ccccc34)c2)cc1]
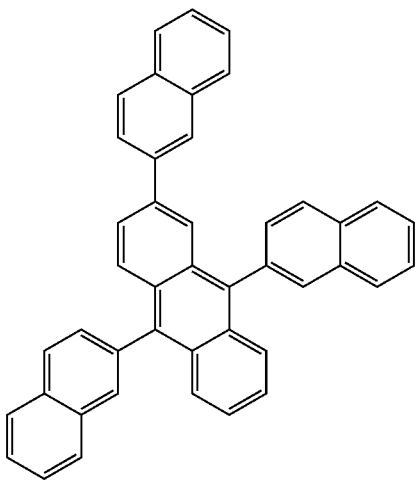 [SMILES: c1ccc2cc(-c3ccc4c(-c5ccc6ccccc6c5)c5ccccc5c(-c5ccc6ccccc6c5)c4c3)ccc2c1]
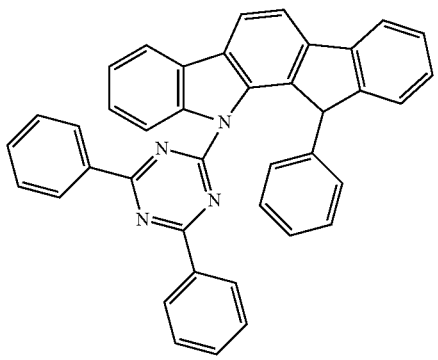 [SMILES: c1ccc(-c2nc(-c3ccccc3)nc(-n3c4ccccc4c4ccc5c(c43)C(c3ccccc3)c3ccccc3-5)n2)cc1]
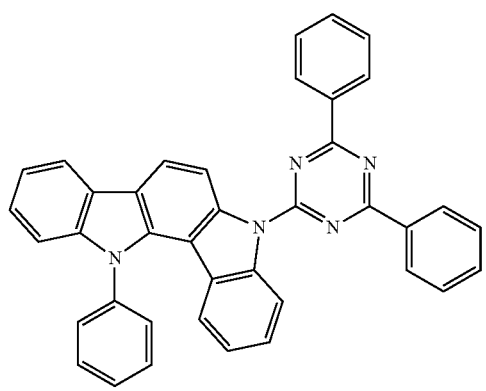 [SMILES: c1ccc(-c2nc(-c3ccccc3)nc(-n3c4ccccc4c4c3ccc3c5ccccc5n(-c5ccccc5)c34)n2)cc1]

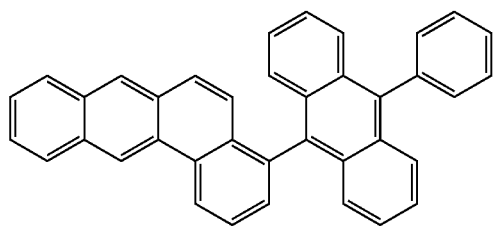 [SMILES: c1ccc(-c2c3ccccc3c(-c3cccc4c3ccc3cc5ccccc5cc34)c3ccccc23)cc1]
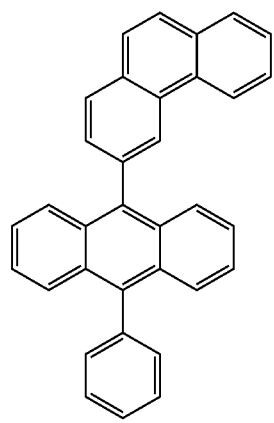 [SMILES: c1ccc(-c2c3ccccc3c(-c3ccc4ccc5ccccc5c4c3)c3ccccc23)cc1]
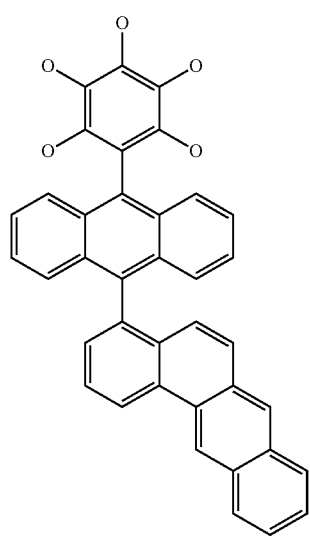 [SMILES: Oc1c(O)c(O)c(-c2c3ccccc3c(-c3cccc4c3ccc3cc5ccccc5cc34)c3ccccc23)c(O)c1O]
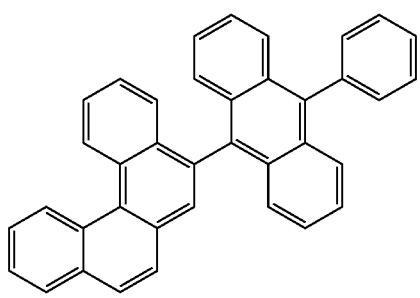 [SMILES: c1ccc(-c2c3ccccc3c(-c3cc4ccc5ccccc5c4c4ccccc34)c3ccccc23)cc1]

-continued
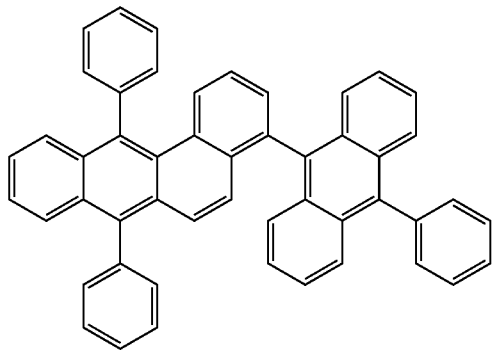 [SMILES: c1ccc(-c2c3ccccc3c(-c3cccc4c3ccc3c(-c5ccccc5)c5ccccc5c(-c5ccccc5)c34)c3ccccc23)cc1]
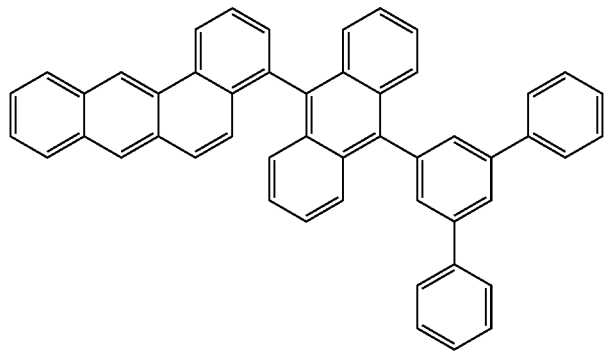 [SMILES: c1ccc(-c2cc(-c3ccccc3)cc(-c3c4ccccc4c(-c4cccc5c4ccc4cc6ccccc6cc45)c4ccccc34)c2)cc1]
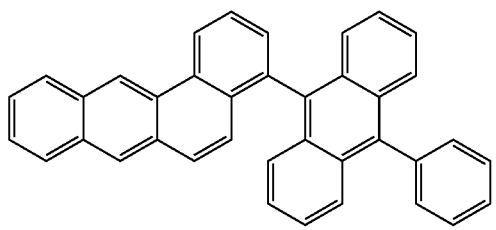 [SMILES: c1ccc(-c2c3ccccc3c(-c3cccc4c3ccc3cc5ccccc5cc34)c3ccccc23)cc1]
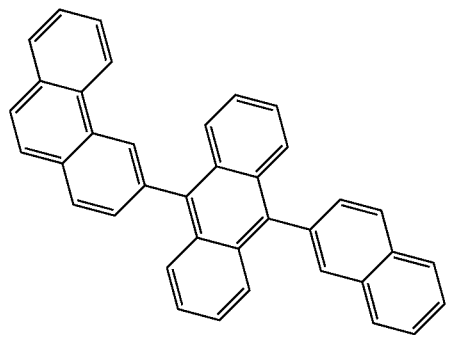 [SMILES: c1ccc2cc(-c3c4ccccc4c(-c4ccc5ccc6ccccc6c5c4)c4ccccc34)ccc2c1]
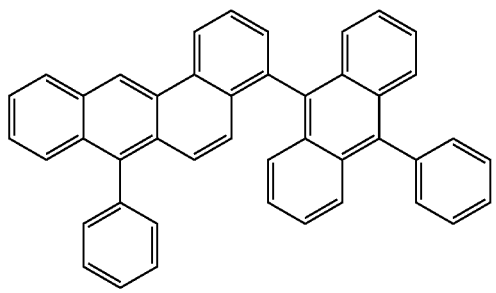 [SMILES: c1ccc(-c2c3ccccc3c(-c3cccc4c3ccc3c(-c5ccccc5)c5ccccc5cc34)c3ccccc23)cc1]

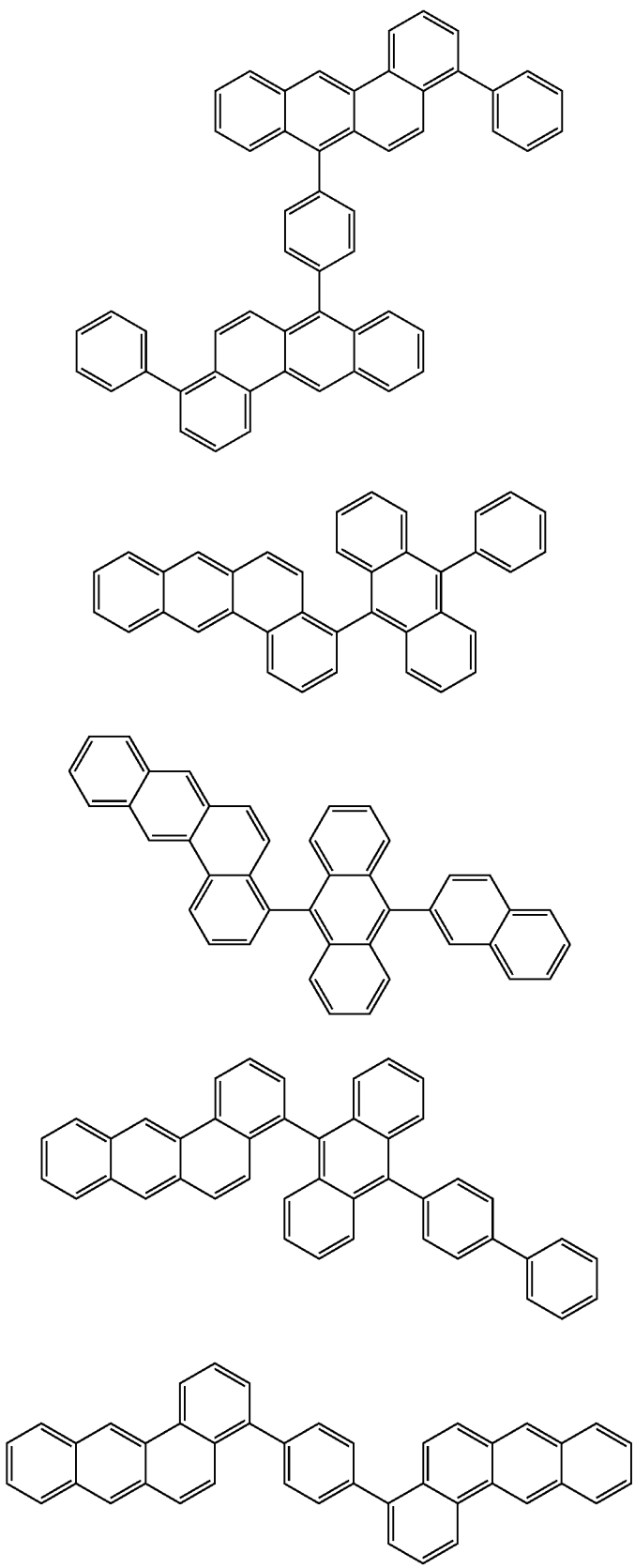

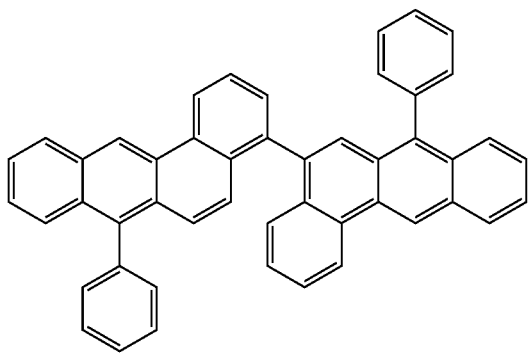 [SMILES: c1ccc(-c2c3ccccc3cc3c2ccc2c(-c4cc5c(-c6ccccc6)c6ccccc6cc5c5ccccc45)cccc23)cc1]
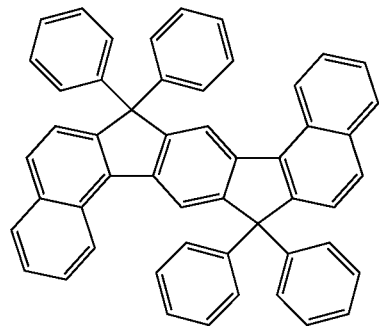 [SMILES: c1ccc(C2(c3ccccc3)c3cc4c(cc3-c3c2ccc2ccccc32)C(c2ccccc2)(c2ccccc2)c2ccc3ccccc3c2-4)cc1]
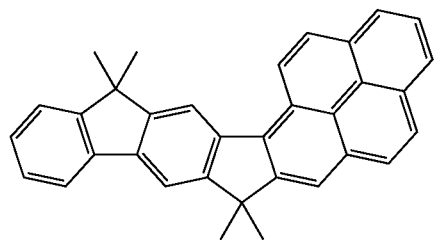 [SMILES: CC1(C)c2ccccc2-c2cc3c(cc21)-c1c(cc2ccc4cccc5ccc1c2c45)C3(C)C]
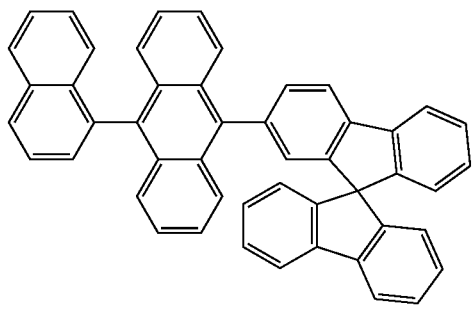 [SMILES: c1ccc2c(c1)-c1ccccc1C21c2ccccc2-c2ccc(-c3c4ccccc4c(-c4cccc5ccccc45)c4ccccc34)cc21]
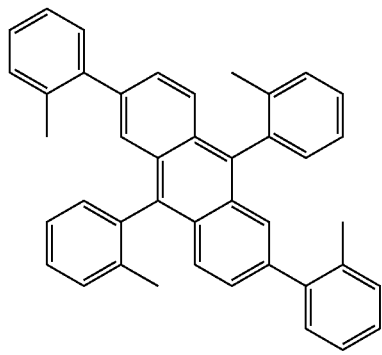 [SMILES: Cc1ccccc1-c1ccc2c(-c3ccccc3C)c3cc(-c4ccccc4C)ccc3c(-c3ccccc3C)c2c1]

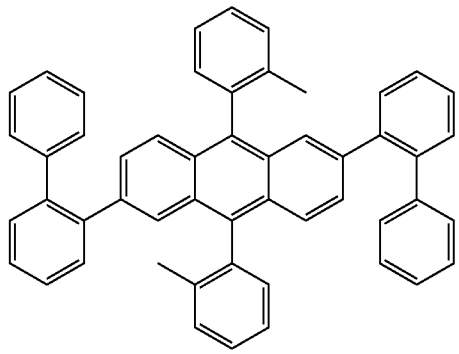 [SMILES: Cc1ccccc1-c1c2ccc(-c3ccccc3-c3ccccc3)cc2c(-c2ccccc2C)c2ccc(-c3ccccc3-c3ccccc3)cc12]
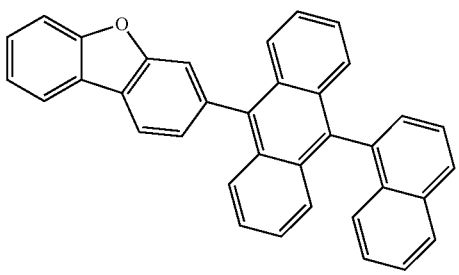 [SMILES: c1ccc2c(-c3c4ccccc4c(-c4ccc5c(c4)oc4ccccc45)c4ccccc34)cccc2c1]
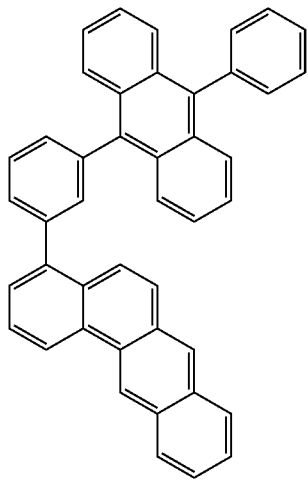 [SMILES: c1ccc(-c2c3ccccc3c(-c3cccc(-c4cccc5c4ccc4cc6ccccc6cc45)c3)c3ccccc23)cc1]
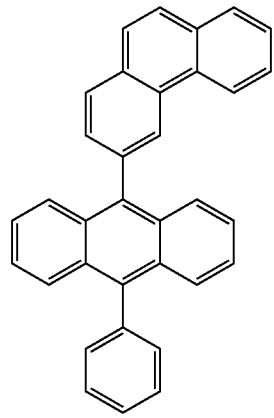 [SMILES: c1ccc(-c2c3ccccc3c(-c3ccc4ccc5ccccc5c4c3)c3ccccc23)cc1]
Besides the compounds of the formula (I) to (IV), suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Ba/Ag or Mg/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) to (IV) are necessary for this purpose. High solubility can be achieved through suitable substitution of the compounds.

For the production of an organic electroluminescent device according to the invention, it is furthermore preferred to apply one or more layers from solution and one or more layers by a sublimation process.

The organic electroluminescent devices comprising one or more compounds of the formula (I) to (IV) can be employed in accordance with the invention in displays, as light sources in lighting applications and as light sources in medical and/or cosmetic applications (for example light therapy).

On use of the compounds of the formula (I) to (IV) in organic electroluminescent devices, one or more of the advantages indicated below can be achieved:
  on use of the compounds of the formula (I) to (IV) as matrix materials for phosphorescent emitters, high power efficiency and a low operating voltage of the devices can be achieved
  on use of the compounds of the formula (I) to (IV) as hole-transport materials, preferably in a hole-transport layer, high power efficiency and a low operating voltage of the devices can be achieved
  using the compounds of the formula (I) to (IV), devices can be produced which have a long lifetime.

The use of the compounds of the formula (I) to (IV) is not restricted to the functions hole-transport material and matrix material for phosphorescent emitters. For example, the use as electron-transport material and/or as matrix material in mixed-matrix systems is furthermore possible.

The invention is explained in greater detail by the following working examples without thereby intending to imply a restriction to the examples explicitly disclosed.

USE EXAMPLES

A) Synthesis Examples

The following syntheses are carried out, unless indicated otherwise, under a protective-gas atmosphere in dried solvents. The solvents and reagents can be purchased from ALDRICH or ABCR. Benzimidazo[2,1-b]guinazolin-12 (6H)-one [4149-00-2] was prepared in accordance with SU 1182043, 6,12-dihydrobenzimidazo[2,1-b]quinazoline [32675-34-6] was prepared in accordance with W. H. W. Lumm et al., J. Org. Chem. 1972, 37, 4, 607 and 5H-benzimidazo[1,2-a]benzimidazole [28890-99-5] was prepared in accordance with A. Reddouane et al., Bull, Soc. Chim. Beiges 96, 10, 787, 1987.

Example 1: Matrix M1

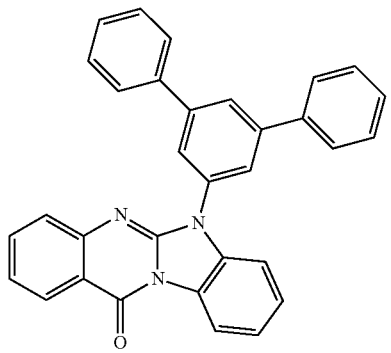 [SMILES: O=c1c2ccccc2nc2n(-c3cc(-c4ccccc4)cc(-c4ccccc4)c3)c3ccccc3n12]

A mixture of 23.5 g (100 mmol) of benzimidazo[2,1-b]quinazolin-12(6H)-one, 34.0 g (110 mmol) of 1-bromo-3,5-diphenylbenzene [103068-20-8], 20.7 g (150 mmol) of potassium carbonate, 3.8 g (20 mmol) of copper iodide, 200 g of glass beads (diameter 3 mm) and 300 ml of NMP is heated at 200° C. for 20 h with vigorous stirring. After cooling, a mixture of 200 ml of water and 200 ml of ethanol is added, the mixture is stirred for a further 30 min., the suspension is filtered through a slotted frit in order to separate off the glass beads, the solid is then filtered off with suction, washed three times with 100 ml of ethanol each time and dried in vacuo. The solid is subjected to continuous hot extraction with o-xylene through an aluminium oxide bed (aluminium oxide, basic, activity grade 1), subsequently recrystallised five times from NMP and three times from o-dichlorobenzene and then subjected to fractional sublimation in vacuo (pressure about $10^{-5}$ mbar, temperature about 320° C.). Yield: 21.3 g (46 mmol), 46%; purity: 99.9% according to HPLC.

The following compounds are prepared analogously:

| Ex. | Bromide | Product | Yield |
|---|---|---|---|
| 2 | | Matrix M2 | 46% |
| 3 | | Matrix M3 | 45% |

-continued
| Ex. | Bromide | Product | Yield |
|---|---|---|---|
| 4 | 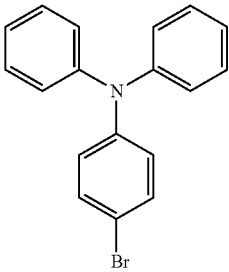 36809-26-4 | 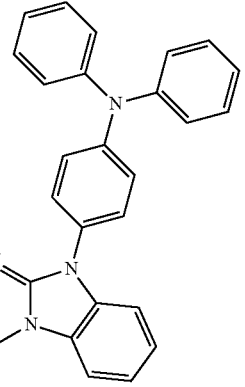 Matrix M4 | 38% |
| 5 | 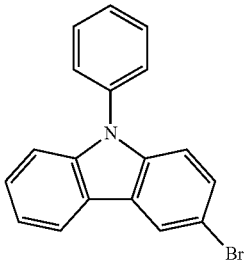 1153-85-1 | 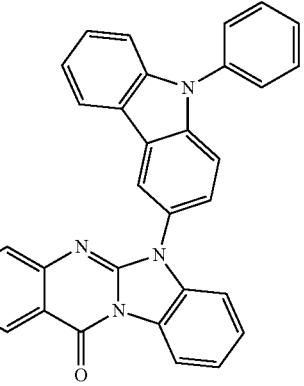 Matrix M5 | 52% |
| 6 | 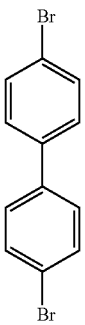 92-86-4 Use of 45 mmol | 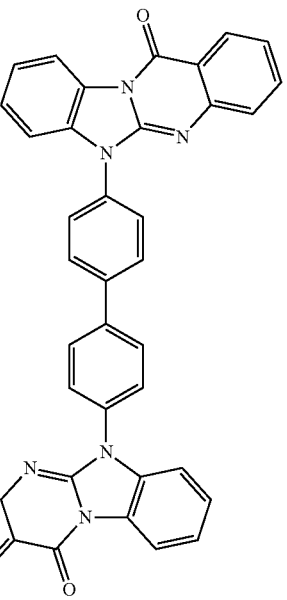 Matrix M6 | 36% |

-continued

| Ex. | Bromide | Product | Yield |
|---|---|---|---|
| 7 | 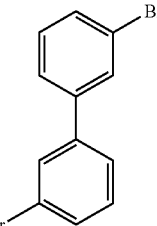<br>16400-51-4<br>Use of 45 mmol | 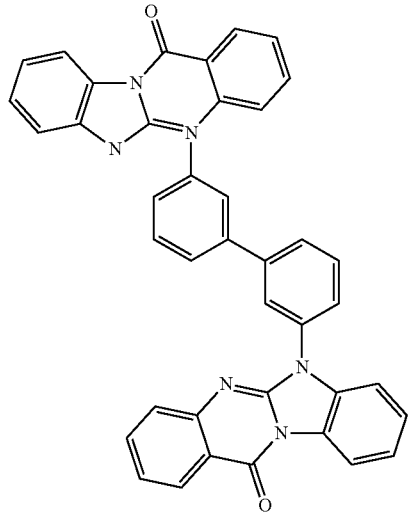<br>Matrix M7 | 44% |
| 8 | 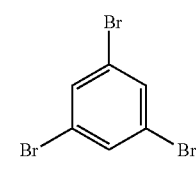<br>626-39-1<br>Use of 30 mmol | 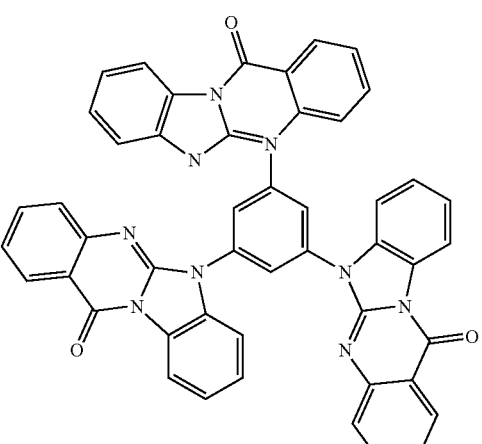<br>Matrix M8 | 28% |

Example 9: Matrix M9

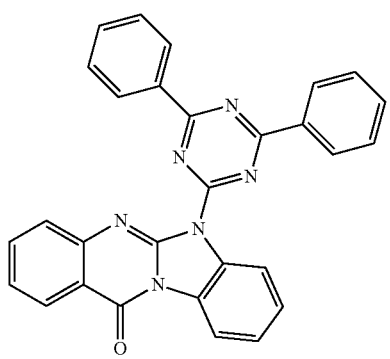 [SMILES: O=c1c2ccccc2nc2n(-c3nc(-c4ccccc4)nc(-c4ccccc4)n3)c3ccccc3n12]

A suspension of 23.5 g (100 mmol) of benzimidazo[2,1-b]quinazolin-12(6H)-one, 2.6 g (110 mmol) of sodium hydride and 29.4 g (110 mmol) of 1-chloro-3,5-diphenyltriazine [3842-55-5] in 300 ml of DMF is stirred at 120° C. for 16 h. After cooling, 100 ml of ethanol are added dropwise, and 100 ml of water are then added, the solid is filtered off with suction, washed three times with 100 ml of a mixture of ethanol/water (1:1, vv) each time, three times with 100 ml of ethanol each time and then dried in vacuo. After recrystallisation of the solid three times from NMP, the product is recrystallised a further seven times from o-dichlorobenzene and then subjected to fractional sublimation in vacuo (pressure about $10^{-5}$ mbar, temperature about 340° C.). Yield: 30.2 g (67 mmol), 67%; purity: 99.9% according to HPLC. The following compounds are prepared analogously:

7.6 g (200 mmol) of lithium aluminium hydride are added in portions to a vigorously stirred suspension, cooled to 0° C., of 46.4 g (100 mmol) of 6-[1,1;3',1"]-terphenyl-5'-yl-6,

| Ex. | Diazine/triazine | Product | Yield |
|---|---|---|---|
| 10 | 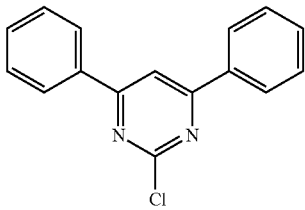<br>2915-16-4 | 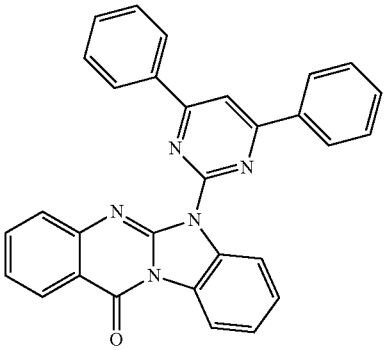<br>Matrix M10 | 59% |
| 11 | 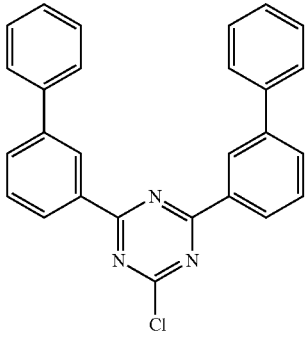<br>1205748-61-3 | 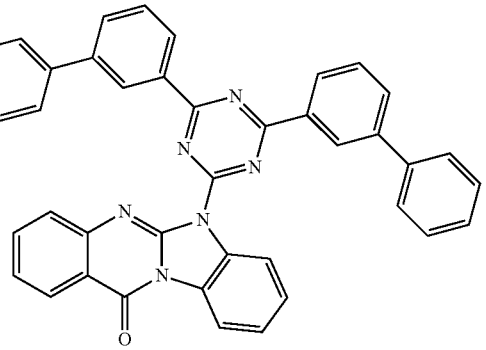<br>Matrix M11 | 63% |

Example 12: Hole Conductor HTM 12

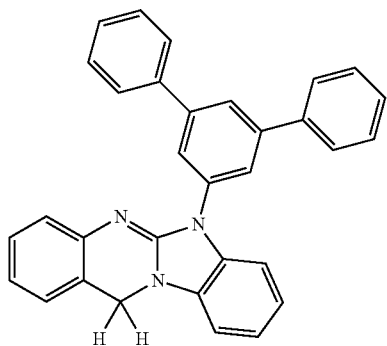 [SMILES: c1ccc(-c2cc(-c3ccccc3)cc(N3C4=Nc5ccccc5CN4c4ccccc43)c2)cc1]

12-dihydrobenzimidazo[2,1-b]quinazoline (Ex. 1) in 1000 ml of diethylene glycol dimethyl ether. The reaction mixture is allowed to warm slowly to room temperature over the course of 4 h and is then stirred for a further 12 h. A mixture of 7.6 ml of water and 50 ml of diethylene glycol dimethyl ether, 7.6 ml of NaOH solution (10% by weight) and then 23.0 ml of water is added dropwise to the reaction mixture with vigorous stirring. The salts are filtered off with suction, rinsed with 100 ml of diethylene glycol dimethyl ether and removed in vacuo. After recrystallisation of the solid five times from NMP, the product is subjected to fractional sublimation in vacuo (pressure about $10^{-5}$ mbar, temperature about 320° C.). Yield: 17.5 g (39 mmol), 39%; purity: 99.9% according to HPLC.

The following compounds are prepared analogously:

| Ex. | Benzimidazo[2,1-b]-quinazolin-12(6H)-one | Product | Yield |
|---|---|---|---|
| 13 | Ex. 3 | HTM 13 | 46% |
| 14 | Ex. 4 | HTM 14 | 45% |

Example 15: Hole Conductor HTM 15

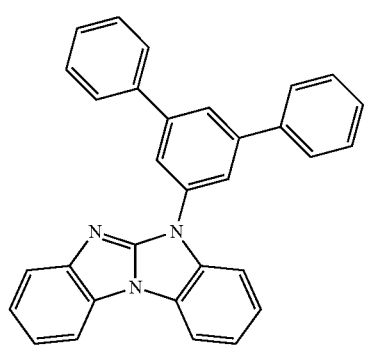 [SMILES: c1ccc(-c2cc(-c3ccccc3)cc(-n3c4ccccc4n4c5ccccc5nc34)c2)cc1]

A mixture of 20.7 g (100 mmol) of 5H-benzimidazo[1,2-a]benzimidazole, 34.0 g (110 mmol) of 1-bromo-3,5-diphenylbenzene [103068-20-8], 20.7 g (150 mmol) of potassium carbonate, 3.8 g (20 mmol) of copper iodide, 200 g of glass beads (diameter 3 mm) and 300 ml of NMP is heated at 200° C. for 20 h with vigorous stirring. After cooling, a mixture of 200 ml of water and 200 ml of ethanol is added, the mixture is stirred for a further 30 min., the suspension is filtered through a slotted frit in order to separate off the glass beads, the solid is then filtered off with suction, washed three times with 100 ml of ethanol each time and dried in vacuo. The solid is subjected to continuous hot extraction with o-xylene through an aluminium oxide bed (aluminium oxide, basic, activity grade 1), subsequently recrystallised twice from NMP and five times from o-dichlorobenzene and then subjected to fractional sublimation in vacuo (pressure about $10^{-5}$ mbar, temperature about 310° C.). Yield: 9.6 g (22 mmol), 22%; purity: 99.9% according to HPLC.

B) Device Examples

Example 16: Production of OLEDs

OLEDs according to the invention and OLEDs in accordance with the prior art are produced by a general process in accordance with WO 04/058911, which is adapted to the circumstances described here (layer-thickness variation, materials used).

The results for various OLEDs are presented in Examples 17 to 35 below (see Tables 1, 2 and 3). Glass plates which have been coated with structured ITO (indium tin oxide) in a thickness of 150 nm are coated with 20 nm of PEDOT (poly(3,4-ethylenedioxy-2,5-thiophene), applied by spin coating from water, purchased from H. C. Starck, Goslar, Germany) for improved processing. These coated glass plates form the substrates to which the OLEDs are applied. The OLEDs have in principle the following layer structure: substrate/hole-injection layer (HIL1, comprising HIL1, 20 nm)/hole-transport layer (HTL, comprising HTM1 (reference) or the HTMs according to the invention, 20 nm)/electron-blocking layer (EBL, 20 nm)/emission layer (EML comprising matrix materials M1 to M11 M according to the invention, 40 nm)/electron-transport layer (ETL, comprising ETL1, 20 nm)/electron-injection layer (EIL, comprising LiF, 1 nm) and finally a cathode. The cathode is formed by an aluminium layer with a thickness of 100 nm. The precise structure of the OLEDs, in particular the structure of the hole-conductor or emitter layer, and the results obtained with these OLEDs on use of the compounds according to the invention as matrix materials for phosphorescent emitters is shown in Table 1 for green-emitting OLEDs and in Table 2 for blue-emitting OLEDs. Table 3 shows the results for the use of compounds according to the invention both as matrix materials for phosphorescent emitters and also as hole-transport materials.

The materials used for the production of the OLEDs are shown in Table 4.

All materials are applied by thermal vapour deposition in a vacuum chamber. The emission layer here always consists of at least one matrix material (host material) and an emitting dopant (dopant, emitter), with which the matrix material or matrix materials is admixed in a certain proportion by volume by co-evaporation.

The as yet unoptimised OLEDs are characterised by standard methods. For this purpose, the electroluminescence spectra, the current efficiency (measured in cd/A) and the voltage are determined. The efficiencies and voltages indicated in the tables relate to the corresponding values at an operating luminance of 1000 cd/m$^2$.

TABLE 1

Green-emitting OLEDs

| Ex. | EML | Efficiency [cd/A] | Voltage [V] | CIE, x/y |
|---|---|---|---|---|
| 17 | M1: TEG1 (15%) | 41.2 | 4.8 | 0.33/0.62 |
| 18 | M2: TEG1 (15%) | 37.9 | 4.7 | 0.33/0.62 |
| 19 | M3: TEG1 (15%) | 44.0 | 4.8 | 0.33/0.62 |
| 20 | M4: TEG2 (15%) | 52.0 | 4.5 | 0.32/0.61 |
| 21 | M5: TEG2 (15%) | 55.3 | 4.4 | 0.32/0.61 |
| 22 | M6: TEG2 (15%) | 48.0 | 4.4 | 0.32/0.61 |
| 23 | M7: TEG2 (15%) | 45.5 | 4.3 | 0.32/0.61 |
| 24 | M8: TEG2 (15%) | 34.6 | 4.5 | 0.32/0.61 |
| 25 | M9: TEG2 (15%) | 50.0 | 4.3 | 0.36/0.58 |
| 26 | M10: TEG2 (15%) | 45.0 | 4.1 | 0.36/0.58 |
| 27 | M11: TEG2 (15%) | 52.7 | 4.2 | 0.36/0.58 |

TABLE 2

Blue-emitting OLEDs

| Ex. | EML | Efficiency [cd/A] | Voltage [V] | CIE, x/y |
|---|---|---|---|---|
| 28 | M1: TEB1 (15%) | 22.4 | 6.8 | 0.16/0.26 |
| 29 | M5: TEB1 (15%) | 24.0 | 6.6 | 0.16/0.27 |
| 30 | M1: TEB2 (15%) | 32.3 | 4.9 | 0.17/0.38 |
| 31 | M5: TEB2 (15%) | 28.1 | 4.8 | 0.17/0.38 |

TABLE 3

Green-emitting OLEDs

| Ex. | HTM/EML | Efficiency [cd/A] | Voltage [V] | CIE, x/y |
|---|---|---|---|---|
| 32 | HTM12/ M6: TEG2 (15%) | 48.3 | 4.4 | 0.32/0.61 |
| 33 | HTM13/ M6: TEG2 (15%) | 52.1 | 4.3 | 0.32/0.61 |
| 34 | HTM14/ M6: TEG2 (15%) | 53.0 | 4.3 | 0.32/0.61 |
| 35 | HTM15/ M6: TEG2 (15%) | 46.7 | 4.1 | 0.32/0.61 |

TABLE 4

Structural formulae of the materials used

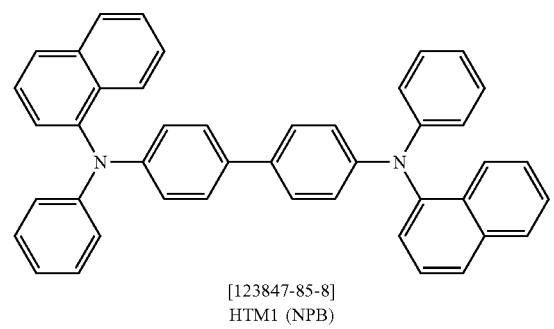

[515834-67-0]
HIL1

[123847-85-8]
HTM1 (NPB)

TABLE 4-continued

Structural formulae of the materials used

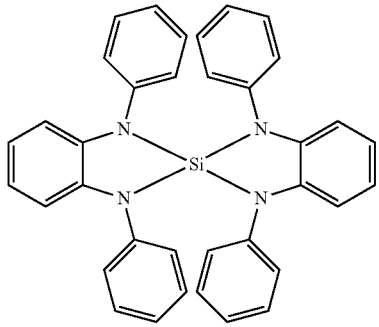 [SMILES: c1ccc(N2c3ccccc3N(c3ccccc3)[Si]23N(c2ccccc2)c2ccccc2N3c2ccccc2)cc1]

DE 102008056688.8
EBL

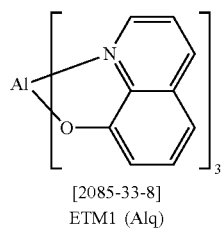

[2085-33-8]
ETM1 (Alq)

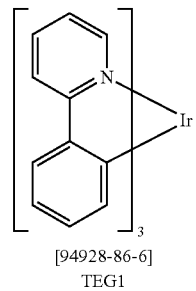

[94928-86-6]
TEG1

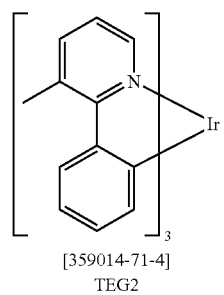

[359014-71-4]
TEG2

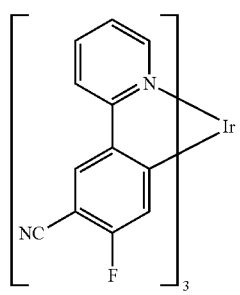

[613682-85-2]
TEB1

TABLE 4-continued

Structural formulae of the materials used

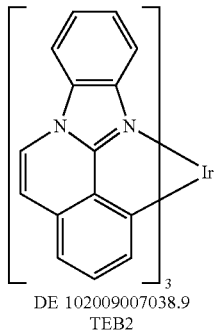

DE 102009007038.9
TEB2

As is clearly evident from the examples shown above, the materials according to the invention are particularly suitable for use as matrix materials for phosphorescent emitters and as hole conductors, where they result in high efficiencies and low operating voltages.

The invention claimed is:

1. An electronic device comprising anode, cathode and at least one organic layer, wherein the organic layer comprises at least one compound of the formula (Ic) or (IIIc)

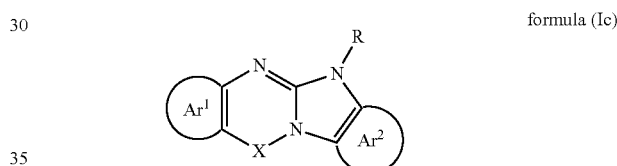

formula (Ic)

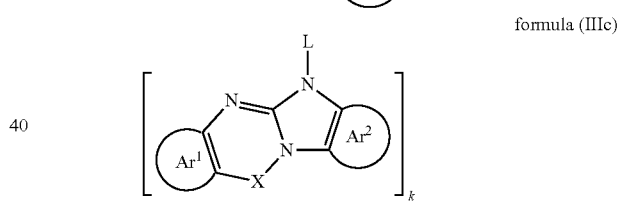

formula (IIIc)

where the following applies to the symbols occurring:

X is a single bond;

L is a divalent, or in the case of k=3, 4, 5 or 6 a tri-, tetra-, penta- or hexavalent group respectively, selected from C=O, C=NR$^1$, Si(R$^1$)$_2$, P(=O)(R$^1$), SO, SO$_2$, alkylene groups having 1 to 20 C atoms, alkenylene or alkynylene groups having 2 to 20 C atoms, where, in the case of the groups mentioned, one or more CH$_2$ groups is optionally replaced by Si(R$^1$)$_2$, O, S, C=O, C=NR$^1$, C=O—O, C=O—NR$^1$, NR$^1$, P(=O)(R$^1$), SO or SO$_2$ and where one or more H atoms in the above-mentioned groups is optionally replaced by D, F, Cl, Br, I, CN or NO$_2$, aromatic or heteroaromatic ring systems having 5 to 60 aromatic ring atoms, each of which is optionally substituted by one or more radicals R$^1$, and any desired combinations of 1, 2, 3, 4 or 5 identical or different groups selected from the above-mentioned groups; or L is a single bond, where k in this case must be equal to 2;

R is an aromatic or heteroaromatic ring system having 5 to 60 aromatic ring atoms, which may in each case be substituted by one or more radicals R$^1$, or an aralkyl or heteroaralkyl group having 5 to 60 aromatic ring atoms, which is optionally substituted by one or more radicals $R^1$, or a combination of these systems, where furthermore the radical R is optionally linked to one or more adjacent radicals $Ar^1$ and $Ar^2$ via a single bond or a divalent group Y;

Y is on each occurrence, identically or differently, a divalent group selected from C=O, C=S, C=NR$^1$, C(R$^1$)$_2$, Si(R$^1$)$_2$, NR$^1$, PR$^1$, P(=O)R$^1$, O, S, SO and SO$_2$;

$R^1$ is on each occurrence, identically or differently, H, D, F, Cl, Br, I, CHO, N(R$^2$)$_2$, C(=O)R$^2$, P(=O)(R$^2$)$_2$, S(=O)R$^2$, S(=O)$_2$R$^2$, CN, NO$_2$, Si(R$^2$)$_3$, B(OR$^2$)$_2$, OSO$_2$R$^2$, OH, COOR$^2$, CON(R$^2$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals $R^2$ and where one or more CH$_2$ groups in the above-mentioned groups is optionally replaced by Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, —O—, —S—, —COO— or —CONR$^2$— and where one or more H atoms in the above-mentioned groups is optionally replaced by D, F, Cl, Br, I, CN or NO$_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which is optionally substituted by one or more radicals $R^2$, or a combination of these systems, where two or more radicals $R^1$ is optionally linked to one another and may form an aliphatic or aromatic ring;

$Ar^1$ and $Ar^2$ are, identically or differently, an aryl group containing 6 to 60 aromatic ring atoms or a heteroaryl group containing 5 to 60 aromatic ring atoms, each of which is optionally substituted by one or more radicals $R^1$; and $R^2$ is, identically or differently on each occurrence, H, D, F or an aliphatic, aromatic and/or heteroaromatic organic radical having 1 to 20 C atoms, in which, in addition, one or more H atoms is optionally replaced by D or F; two or more substituents $R^2$ here may also be linked to one another and form an aliphatic or aromatic ring; and k is equal to 2, 3, 4, 5 or 6.

2. The electronic device according to claim 1, wherein the radical R represents an aryl or heteroaryl group having 5 to 20 aromatic ring atoms, which may in each case be substituted by one or more radicals $R^1$, or represents an aralkyl or heteroaralkyl group having 5 to 20 aromatic ring atoms, which is optionally substituted by one or more radicals $R^1$, where the radical R may furthermore be linked to one of the groups $Ar^1$ and $Ar^2$ via a single bond or via a divalent group Y.

3. The electronic device according to claim 1, wherein k is equal to 2 or 3.

4. The electronic device according to claim 1, wherein the compound of one of the formula (Ic) or (IIIc) represents a compound of one of the formulae (IX-1) to (IX-3) and (X-1)

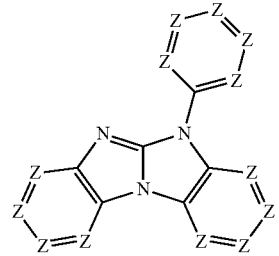
formula (IX-1)

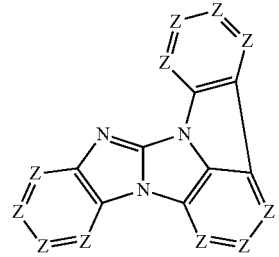
formula (IX-2)

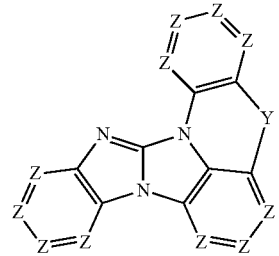
formula (IX-3)

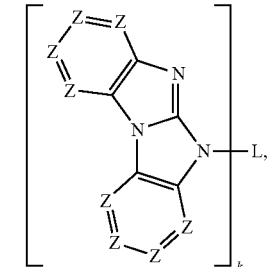
formula (X-1)

where the symbols occurring are as defined in claim 1 and furthermore

Z is on each occurrence, identically or differently, CR$^1$ or N, where not more than two adjacent groups Z may simultaneously be equal to N.

5. The electronic device according to claim 1, wherein the device is an organic integrated circuit (O-IC), organic field-effect transistor (O-FET), organic thin-film transistor (O-TFT), organic light-emitting transistor (O-LET), organic solar cell (O-SC), organic optical detector, organic photoreceptor, organic field-quench device (O-FQD), light-emitting electrochemical cell (LEC), organic laser diode (O-laser) and organic electroluminescent device (OLED).

6. The electronic device according to claim 5, wherein the device is an OLED.

7. The electronic device according to claim 1, wherein the compound of one of the formula (Ic) or (IIIc) is employed as hole-transport material in a hole-transport layer or hole-injection layer and/or is employed as matrix material in an emitting layer.

8. A compound of one of the formulae (Ic) or (IIIc)

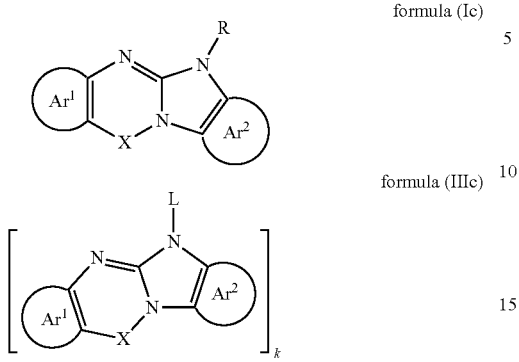

formula (Ic)

formula (IIIc)

wherein
Ar$^1$ and Ar$^2$ are, identically or differently, an aryl group containing 6 to 60 aromatic ring atoms or a heteroaryl group containing 5 to 60 aromatic ring atoms, each of which is optionally substituted by one or more radicals R$^1$; and
R is an aromatic or heteroaromatic ring system having 5 to 20 aromatic ring atoms, which may in each case be substituted by one or more radicals R$^1$, or an aralkyl or heteroaralkyl group having 5 to 20 aromatic ring atoms, which may be substituted by one or more radicals R$^1$, where the radical R may furthermore be linked to an adjacent group Ar$^1$ or Ar$^2$ via a single bond or via a divalent group Y;
X is a single bond;
L is a divalent, or in the case of k=3, 4, 5 or 6 a tri-, tetra-, penta- or hexavalent group respectively, selected from C=O, C=NR$^1$, Si(R$^1$)$_2$, P(=O)(R$^1$), SO, SO$_2$, alkylene groups having 1 to 20 C atoms, alkenylene or alkynylene groups having 2 to 20 C atoms, where, in the case of the groups mentioned, one or more CH$_2$ groups is optionally replaced by Si(R$^1$)$_2$, O, S, C=O, C=NR$^1$, C=O—O, C=O—NR$^1$, NR$^1$, P(=O)(R$^1$), SO or SO$_2$ and where one or more H atoms in the above-mentioned groups is optionally replaced by D, F, Cl, Br, I, CN or NO$_2$, aromatic or heteroaromatic ring systems having 5 to 60 aromatic ring atoms, each of which is optionally substituted by one or more radicals R$^1$, and any desired combinations of 1, 2, 3, 4 or 5 identical or different groups selected from the above-mentioned groups; or L is a single bond, where k in this case must be equal to 2;
Y is on each occurrence, identically or differently, a divalent group selected from C=O, C=S, C=NR$^1$, C(R$^1$)$_2$, Si(R$^1$)$_2$, NR$^1$, PR$^1$, P(=O)R$^1$, O, S, SO and SO$_2$;
R$^1$ is on each occurrence, identically or differently, H, D, F, Cl, Br, I, CHO, N(R$^2$)$_2$, C(=O)R$^2$, P(=O)(R$^2$)$_2$, S(=O)R$^2$, S(=O)$_2$R$^2$, CN, NO$_2$, Si(R$^2$)$_3$, B(OR$^2$)$_2$, OSO$_2$R$^2$, OH, COOR$^2$, CON(R$^2$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals R$^2$ and where one or more CH$_2$ groups in the above-mentioned groups is optionally replaced by Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, —O—, —S—, —COO— or —CONR$^2$— and where one or more H atoms in the above-mentioned groups is optionally replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which is optionally substituted by one or more radicals R$^2$, or a combination of these systems, where two or more radicals R$^1$ is optionally linked to one another and may form an aliphatic or aromatic ring;
R$^2$ is, identically or differently on each occurrence, H, D, F or an aliphatic, aromatic and/or heteroaromatic organic radical having 1 to 20 C atoms, in which, in addition, one or more H atoms is optionally replaced by D or F; two or more substituents R$^2$ here may also be linked to one another and form an aliphatic or aromatic ring; and
k is equal to 2, 3, 4, 5 or 6.

9. An oligomer, polymer or dendrimer comprising one or more compounds according to claim 8, where the bond(s) to the polymer, oligomer or dendrimer may be localised at any position substituted by R or R$^1$ in formula (Ic) or (IIIc).

10. A formulation comprising at least one compound according to claim 8, and at least one solvent.

11. A formulation comprising at least one polymer, oligomer or dendrimer according to claim 9 and at least one solvent.

12. A process for the preparation of the compound of the formula (Ic) or (IIIc) according to the invention according to claim 8, which comprises at least one of the two steps a) and b) indicated below is carried out:
a) deprotonation at the 5- or 6-N atom of the benzimidazoquinazoline skeleton and subsequent reaction with an electrophilic compound, so that a bond is formed between the 5- or 6-N atom and the electrophilic compound;
b) organometallic coupling under Hartwig-Buchwald or Ullmann conditions between the 5- or 6-N atom of the benzimidazoquinazoline skeleton and an aryl group Ar, which is employed as starting material Ar-Hal, where Hal is any suitable leaving group.

13. An electronic device which comprises the compound according to claim 8.

14. An organic electroluminescent device which comprises the compound according to claim 8.

15. An electronic device which comprises the at least one polymer, oligomer dendrimer according to claim 9.

16. An organic electroluminescent device which comprises the compound according to claim at least one polymer, oligomer or dendrimer according to claim 9.

17. An organic electroluminescent device which comprises the compound according to claim 8 as hole-transport material, as matrix material, as emitter material, as electron-blocking material, as hole-injection material, as hole-blocking material and/or as electron-transport material.

18. An organic electroluminescent device which comprises said at least one polymer, oligomer or dendrimer as claimed in claim 9 as a hole-transport material, as matrix material, as emitter material, as electron-blocking material, as hole-injection material, as hole-blocking material and/or as electron-transport material.

* * * * *